United States Patent
Wilkinson et al.

(10) Patent No.: US 10,987,171 B2
(45) Date of Patent: Apr. 27, 2021

(54) ORTHOPEDIC SYSTEMS, COMPONENTS, AND METHODS

(71) Applicant: Smith & Nephew, Inc., Memphis, TN (US)

(72) Inventors: Zachary Christopher Wilkinson, Germantown, TN (US); Bilal Imad Ismail, Cordova, TN (US); Ryan Lloyd Landon, Olive Branch, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/762,028

(22) PCT Filed: Nov. 13, 2018

(86) PCT No.: PCT/US2018/060587
§ 371 (c)(1),
(2) Date: May 6, 2020

(87) PCT Pub. No.: WO2019/094874
PCT Pub. Date: May 16, 2019

(65) Prior Publication Data
US 2020/0375610 A1    Dec. 3, 2020

Related U.S. Application Data

(60) Provisional application No. 62/584,440, filed on Nov. 10, 2017, provisional application No. 62/584,457, (Continued)

(51) Int. Cl.
*A61B 17/15* (2006.01)
*A61B 17/17* (2006.01)
(Continued)

(52) U.S. Cl.
CPC ............ *A61B 34/10* (2016.02); *A61B 17/154* (2013.01); *A61B 17/155* (2013.01);
(Continued)

(58) Field of Classification Search
CPC ..... A61B 17/157; A61B 34/10; A61B 17/155; A61B 17/154
See application file for complete search history.

(56) References Cited

U.S. PATENT DOCUMENTS

| 2007/0288030 A1* | 12/2007 | Metzger | ............... A61B 17/157 606/87 |
| 2012/0209275 A1* | 8/2012 | Fox | ...................... A61B 17/157 606/88 |

(Continued)

FOREIGN PATENT DOCUMENTS

WO     2011/106400 A1     9/2011

OTHER PUBLICATIONS

International Search Report and Written Opinion for International Patent Application No. PCT/US2018/060587, dated Apr. 26, 2019.
(Continued)

*Primary Examiner* — Christian A Sevilla
(74) *Attorney, Agent, or Firm* — Kacvinsky Daisak Bluni PLLC

(57) ABSTRACT

Embodiments of the present application provide technologies related to adaptive surgeon-specific instrumentation, unique preparatory tools and procedures for bone resection and implant devices, and systems for selection of implantation preparatory tools for implantation procedures. The embodiments described herein may, for example, be utilized in connection with knee arthroplasty procedures.

14 Claims, 28 Drawing Sheets

Related U.S. Application Data filed on Nov. 10, 2017, provisional application No. 62/584,476, filed on Nov. 10, 2017.

(51) Int. Cl.
  *A61B 17/56* (2006.01)
  *A61B 34/10* (2016.01)
  *A61B 17/00* (2006.01)

(52) U.S. Cl.
  CPC ........ *A61B 17/157* (2013.01); *A61B 17/1764* (2013.01); *A61B 17/56* (2013.01); *A61B 2017/00526* (2013.01); *A61B 2017/568* (2013.01); *A61B 2034/108* (2016.02)

(56) References Cited

U.S. PATENT DOCUMENTS

| | | | | |
|---|---|---|---|---|
| 2012/0209394 | A1* | 8/2012 | Bojarski | A61B 17/157 623/20.32 |
| 2013/0211531 | A1* | 8/2013 | Steines | A61F 2/3859 623/20.35 |
| 2014/0257309 | A1* | 9/2014 | Aram | A61B 17/1721 606/88 |
| 2017/0100132 | A1* | 4/2017 | Collazo | A61B 17/155 |
| 2017/0112576 | A1* | 4/2017 | Coste-Maniere | A61B 34/25 |
| 2017/0164957 | A1* | 6/2017 | Bojarski | A61B 34/20 |
| 2017/0273718 | A1* | 9/2017 | Metzger | A61B 17/58 |
| 2017/0304007 | A1* | 10/2017 | Piron | A61B 34/20 |
| 2017/0333207 | A1* | 11/2017 | Tsukayama | A61B 17/1631 |
| 2018/0049622 | A1* | 2/2018 | Ryan | A61B 1/00048 |
| 2018/0271577 | A1* | 9/2018 | Bharat | A61B 34/10 |
| 2018/0271602 | A1* | 9/2018 | Frey | G09B 23/30 |
| 2019/0015119 | A1* | 1/2019 | Athwal | A61B 17/1735 |
| 2019/0223886 | A1* | 7/2019 | Fritzinger | A61B 34/10 |
| 2020/0197023 | A1* | 6/2020 | Chafez | A61F 2/30942 |

OTHER PUBLICATIONS

Medacta, "Myknee", medacta.com, Apr. 30, 2015 (Apr. 30, 2015), Retrieved from the Internet: URL:https://media.medacta.com/media/99my2611rev03.pdf, [retrieved on Feb. 5, 2019], pp. 1,2.

MedactaInternational, "MyKnee—Patient Matched Technology", Apr. 17, 2017 (Apr. 17, 2017), p. 1-2, Retrieved from the Internet: URL:https://www.youtube.com/watch?v=ODE3QnZOYVg, [retrieved on Feb. 5, 2019].

Surgi Novi, "SurgiNovi Patient Specific Instruments for Total Knee Replacement", Jul. 13, 2016 (Jul. 13, 2016), p. 1-2, Retrieved from the Internet: URL:https://www.youtube.com/watch?v=1gARoXR4YV4, [retrieved on Feb. 5, 2019].

International Preliminary Report on Patentability for International Patent Application No. PCT/US2018/060587, dated May 12, 2020.

\* cited by examiner

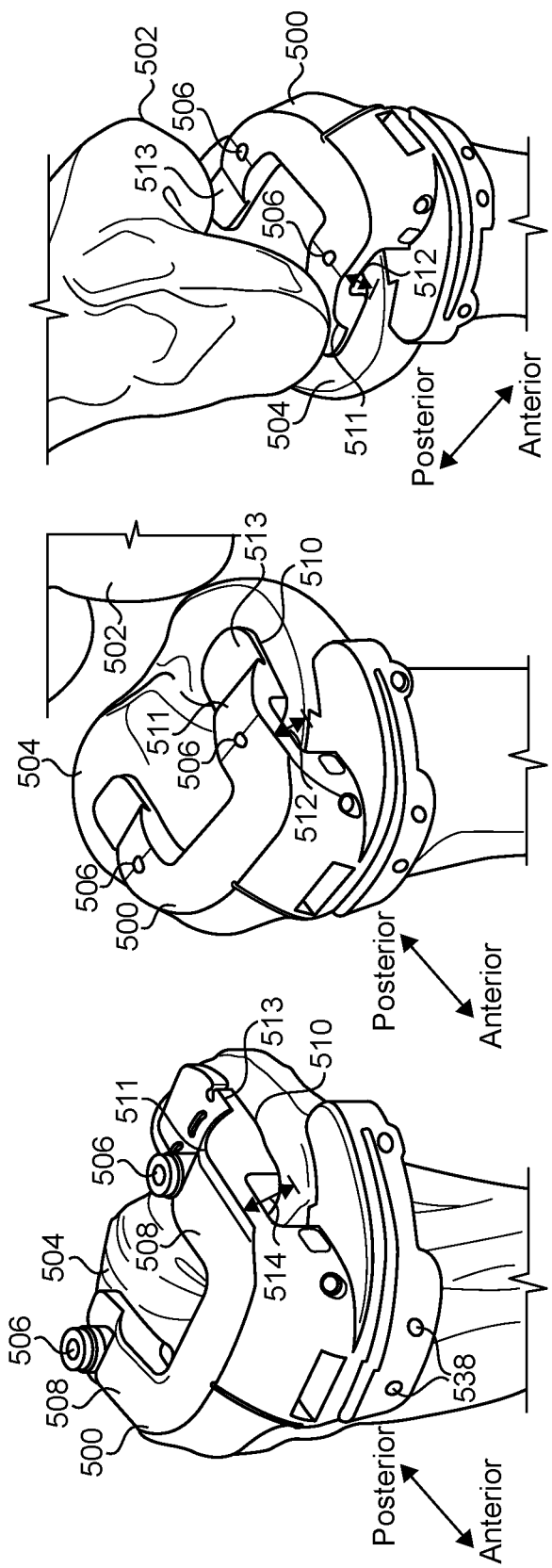

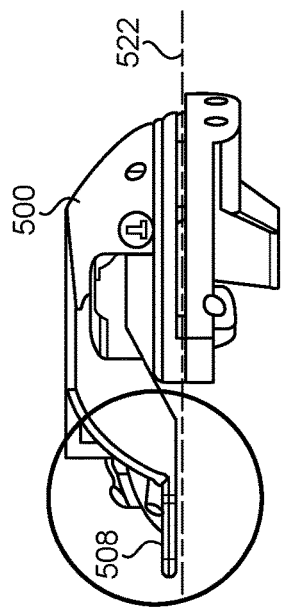
FIG. 15
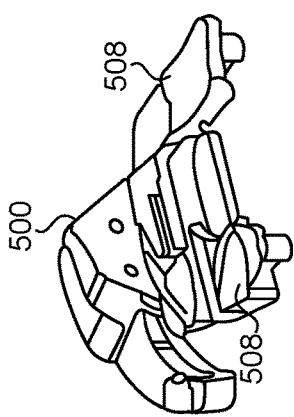
FIG. 14
FIG. 13
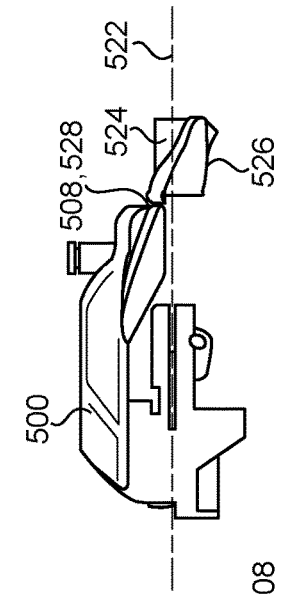
FIG. 18
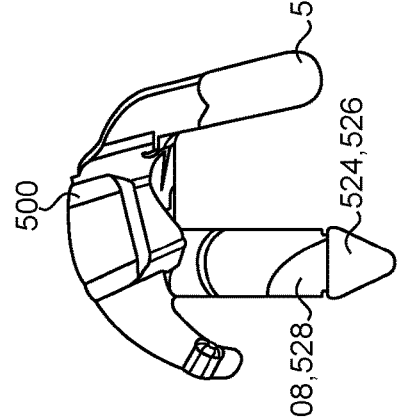
FIG. 17
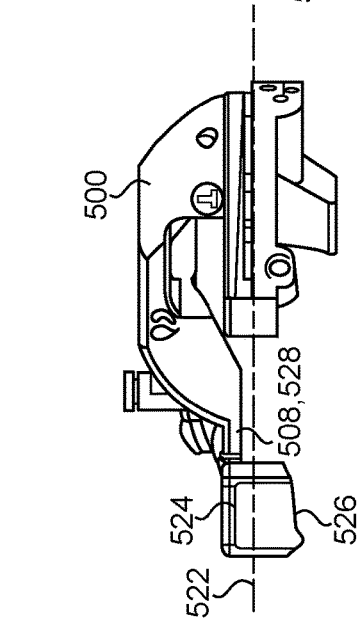
FIG. 16

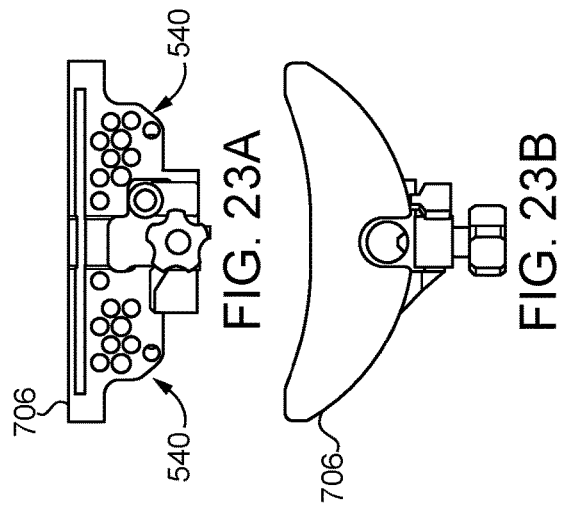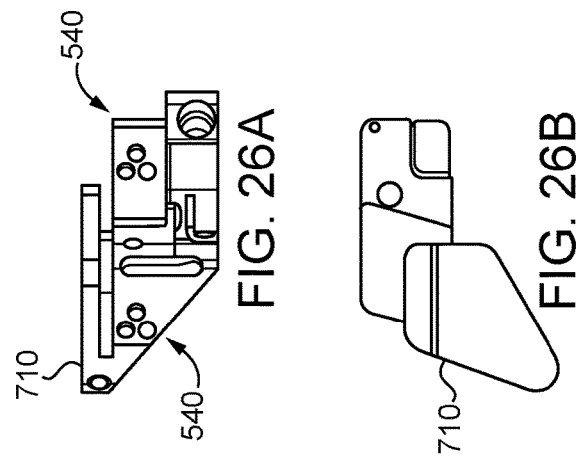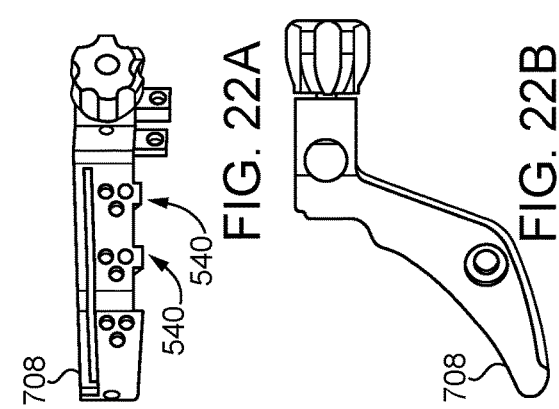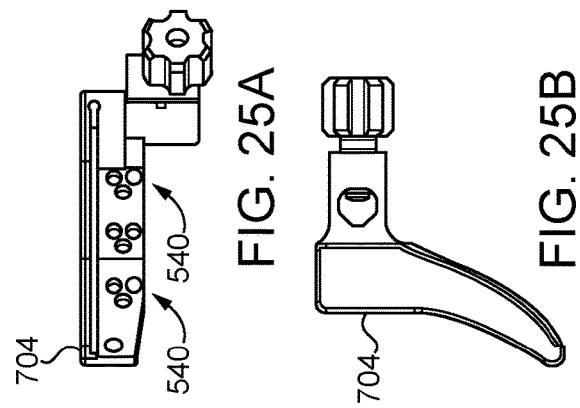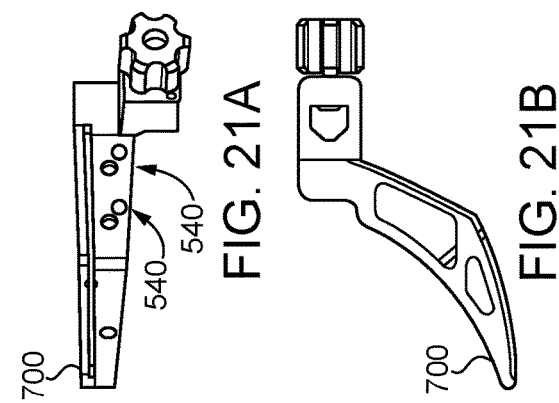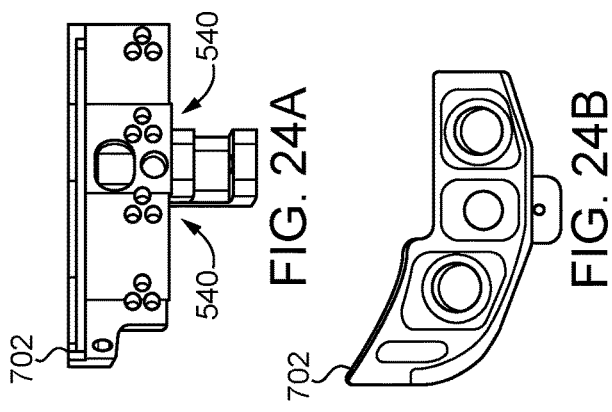

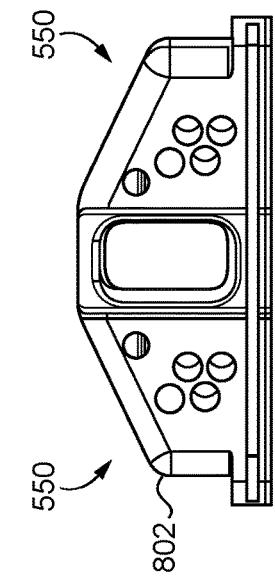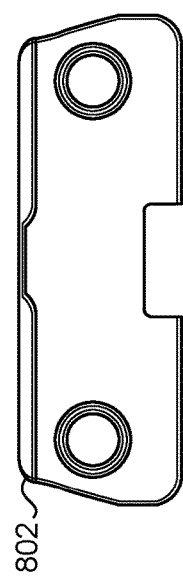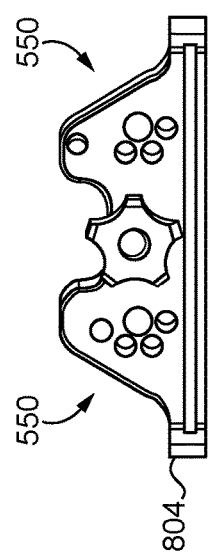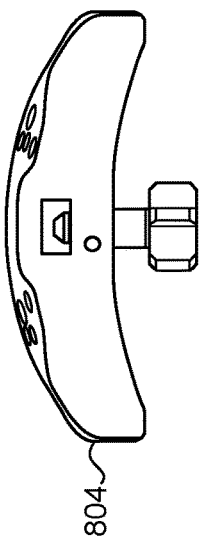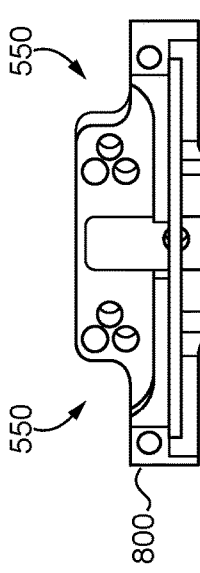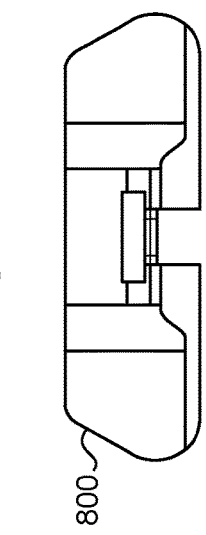

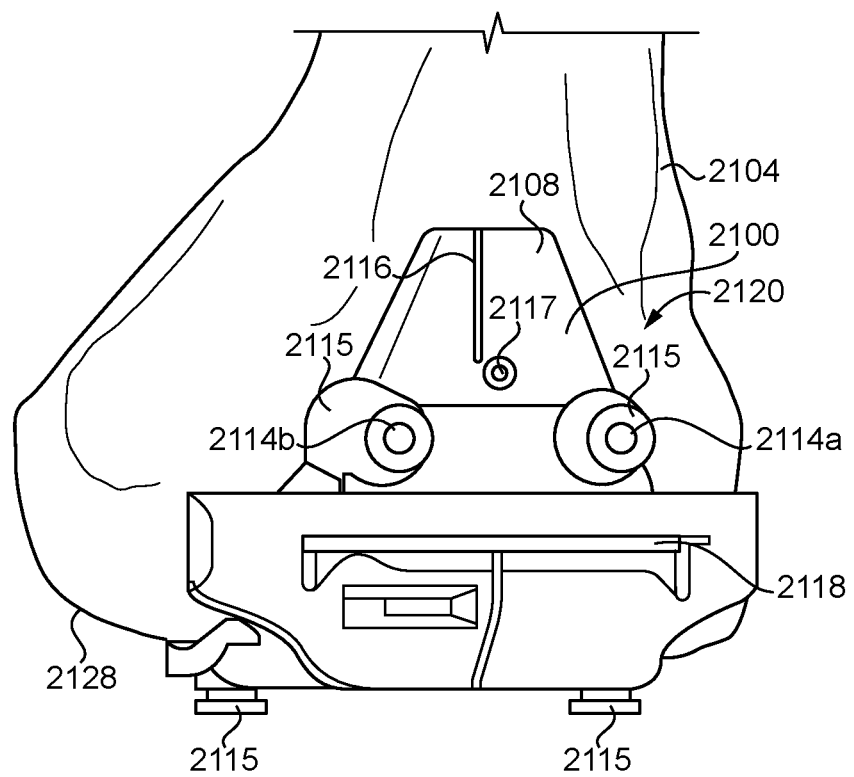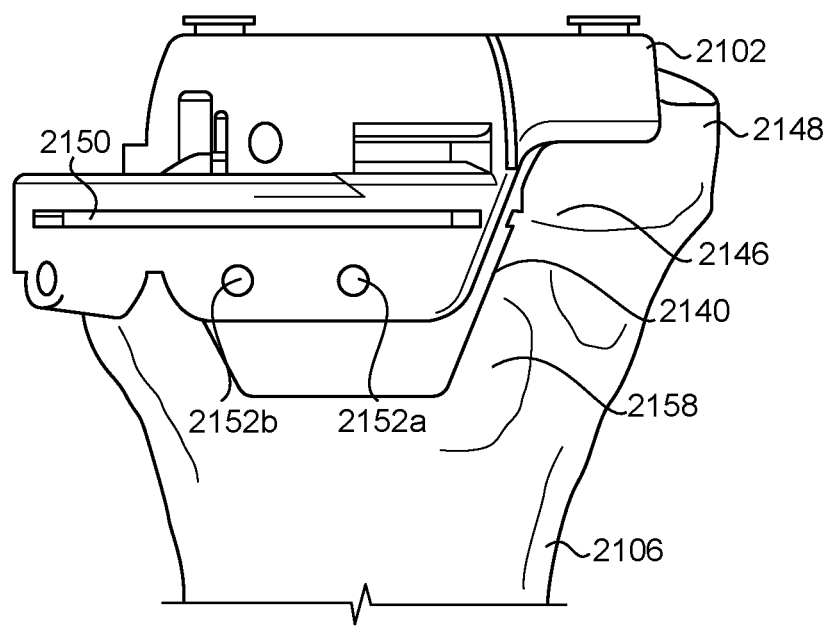
FIG. 51

ORTHOPEDIC SYSTEMS, COMPONENTS, AND METHODS

CROSS-REFERENCE TO RELATED APPLICATIONS

The present application is a United States National Phase filing of International Application No. PCT/US2018/060587, filed 13 Nov. 2018, which claims the benefit of U.S. Provisional Patent Application No. 62/584,440, filed on 10 Nov. 2017, U.S. Provisional Patent Application No. 62/584,457, filed on 10 Nov. 2017, and U.S. Provisional Patent Application No. 62/584,476, filed on 10 Nov. 2017, the contents of each of which are incorporated by reference in their entirety.

BACKGROUND

The training and experiences encountered by an orthopedic surgeon generally results in that surgeon developing specific surgical techniques and preferences, which often require the use of surgical instrumentation for a given surgical procedure that is different from the instrumentation that would be employed by another orthopedic surgeon. For example, some surgeons prefer to use a cutting instrument having a thick cutting blade, whereas other surgeons prefer having a thinner cutting blade. However, maintaining such a wide array of surgical instrumentation as to satisfy every surgeon operating in a particular facility can become unwieldy in terms of inventory management, storage, sanitization, and other factors.

Accommodating patient-specific factors that influence a particular surgeon's decision to use one technique and instrument set for one patient and a different instrument set for a different patient exacerbates these issues. As such, the surgeon's technique and preferences may not align with the available surgical tray configurations. This mismatch may lead to inefficiencies and concerns during surgery including, for example, increased tourniquet time, potential vascular damage, increased wear debris, one or more required bone recuts, increased surgical difficulty, and/or other issues.

Additionally, certain surgical procedures, including, for example, implantation of joint replacement systems and/or joint replacement components, can include procedures to prepare one or more bones of the patient to accommodate implantation of the implant system or implant component(s). As anatomical configurations of patients can, to at least some extent, vary in certain respects, the manner in which different patient's bones are prepared for such implant systems or components can vary.

For example, the particular shape, size, and/or configuration of bones at one or more locations along the bone can differ among patients. Such differences can contribute, at least in some instances, to patients' bones being prepared in different manners, such as, for example, being cut or resected at different locations and/or depths. Other considerations may also influence the manner in which a bone(s) may be prepared in connection with the implantation of an implant system or component(s). For example, ligament insertion locations along at least a portion of the bone can also influence the location and/or depth of a cut into that bone. The size of an implant component can also influence the manner and/or location in which the bone(s) may be prepared. For example, the surgeon may attempt to cut the bone at a location that prevents over-hang or under-hang of a tray or plate that can be implanted at the location at which the bone was resected.

Thus, the manner in which preparatory procedures are performed on a bone may involve a number of considerations. Accordingly, in at least certain situations, such as with respect to patients that have relatively challenging anatomies, certain compromises are often made, such as, for example tradeoffs that can seek, to the extent possible, balance between addressing issues relating to irregularities in bone shape with at least attempts to retain and/or not compromise ligament insertion locations. Yet, despite possible attempts to minimize such compromises prior to proceeding with the actual preparatory procedure(s), often such issues are not known or discovered until after the preparatory procedure has begun and/is completed. For example, with respect to bone preparatory procedures, the final shape and/or size of the bone that will receive the implant may be unknown until the bone has been cut, which typically is too late to reorient the associated bone cut(s).

Furthermore, orthopedic implant systems, including, for example, knee implant systems, often use certain types of preparatory tools, including, for example, cutting blocks, among other preparatory tools, that are system specific. Moreover, at least certain types of preparatory tools can be configured so that the certain features of the preparatory tools, such as, for example, pin holes, and/or the associated pins that may be positioned therein, can be used with securing the preparatory tool(s) to the bone of a patient, while other pin holes and/or the associated pin positioned therein can also be used at least to assist with generally aligning a component of the implant system that will be implanted in the patient.

As a surgeon becomes familiar with a particular knee implant system, including becoming accustomed with the associated preparatory tools, the surgeon can develop a preference for using that system and/or the associated preparatory tools. For example, a surgeon may be trained in orthopedic implant procedures using a particular implant system from a particular manufacturer, and accordingly develop a preference for using that system and/or the associated preparatory tools. However, preparatory tools, including custom preparatory tools, are often system and/or manufacturer specific, and thus are not necessarily designed for use with other implant systems, such as the implant systems of other manufacturers. For example, the preparatory tools of different implant systems may have pinning holes and/or alignment features at different locations, among other differences.

As a result, during an implantation procedure, the surgeon can be limited to either using system-specific preparatory tools for which the surgeon may lack familiarity, and which thus may not be the tool(s) of choice for the surgeon. Alternatively, in at least certain situations, the surgeon may potentially make certain compromises so as to use a preparatory tool(s) of the surgeon's preference, despite that preparatory tool(s) not being intended, or designed, for use with the particular system that the surgeon is implanting.

As is evident from the foregoing, present approaches to the planning and performance of surgeries suffer from a variety of drawbacks and limitations. Accordingly, there remains a need for further developments in this technological field.

SUMMARY

Embodiments of the present application provide technologies related to adaptive surgeon-specific instrumentation, unique preparatory tools and procedures for bone resection and implant devices, and systems for selection of implantation preparatory tools for implantation procedures. The embodiments described herein may, for example, be utilized in connection with knee arthroplasty procedures.

Certain embodiments of the present application relate to systems and methods for providing surgeon-specific customized components that are tuned to the preferences of a particular surgeon and/or optimized for use with the surgeon's preferred set of instruments. Such embodiments may allow the surgery to go faster, with less possibility of infection, vascular damage, wear debris, and/or the need to recut. The customized components may additionally or alternatively maximize the chance of preserving host bone and/or making potential revision surgeries easier.

One particular problem certain embodiments of the present application may solve is a mismatch of instruments. If the cutting guide is not optimized for use in a particular situation, the surgeon may be left with no choice but to use a cutting guide that can harm the patient. As one example, blunt cutting guides are typically preferred for large bones, whereas curved guides are typically preferred for small bones. If the surgeon were forced to use a blunt guide with a small bone, harm may come to the patient.

Another particular problem that may be solved by certain embodiments is harmonizing the thickness of the cutting slot to the thickness of the surgeon's preferred sawblade. Using a thick blade in thin slot can create wear harmful wear debris, while using a thin blade in a thick slot can reduce the accuracy of the cut. By facilitating harmonization of the slot thickness and the blade thickness, these drawbacks can be reduced or eliminated.

A further problem that may be solved by certain embodiments involves over-driven pins. Typically, a pin that is over-driven needs to be carved out with a rongeur. This process can increase surgical time, which could lead to vascular damage and infection. Certain embodiments of the present application obviate these difficulties by facilitating the removal of such over-driven pins.

Certain embodiments of the present application relate to systems and methods that enable a surgeon to utilize a particular style of cutting guide with another style of implant that is not necessarily designed for use with that particular style of cutting guide. Such embodiments increase the number of styles of cutting guides that the surgeon is capable of using with a given implant style, thereby allowing the surgeon to make better use of the cutting guide inventory. In addition to increasing efficiency, these embodiments may improve results for the patient, for example when the surgeon is accustomed to using a particular style of cutting guide. These embodiments may also allow for non-standard guides such as those better matched to the transverse bone cross-section associated with a particular size or pathology.

Certain embodiments of the present application enable the surgeon to visualize the location of a particular cut before that cut is made on the patient. Such embodiments may simplify the surgical procedure by providing simple alignment for the more critical aspects of the implant at an early stage of the procedure without requiring the surgeon to manipulate dials, slides, or knobs. Such simplification may reduce the likelihood of error during the surgical procedure.

Further features and advantages of at least some of the embodiments of the present invention, as well as the operation of various embodiments of the present invention, are described in detail below with reference to the accompanying drawings.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

FIG. 5 is a perspective view of a surgeon-specific tibial cutting guide for use with a distal cut first surgical technique.

FIGS. 6-7 are perspective views of a surgeon-specific tibial cutting guide for use with a tibial cut first surgical technique.

FIG. 13 is an example of a patient's bone having a proximal tibia that is badly damaged.

FIG. 14 is a bottom perspective view of a surgeon-specific tibial cutting guide for which no portion of the tibial paddles passes below the cut plane.

FIG. 15 is a side view of the surgeon-specific tibial guide of FIG. 14.

FIG. 16 is a side view of a surgeon-specific tibial cutting guide having a tibial paddle that extends through the cut plane.

FIG. 17 is a bottom view of the surgeon-specific tibial cutting guide of FIG. 16.

FIG. 18 is an opposite side view of the surgeon-specific tibial cutting guide of FIG. 16.

FIGS. 21A, 22A, 23A, 24A, 25A, and 26A are anterior views of various tibial recut guides.

FIGS. 21B, 22B, 23B, 24B, 25B, and 26B are anterior views of the tibial recut guides of FIGS. 21A, 22A, 23A, 24A, 25A, and 26A, respectively.

FIGS. 27A, 28A, and 29A are anterior views of various femoral recut guides.

FIGS. 27B, 28B, and 29B are distal views of the femoral recut guides of FIGS. 27A, 28A, and 29A, respectively.

FIG. 51 illustrates an anterior view of a general knee joint in which an exemplary femoral cutting block and an exemplary tibial cutting block are coupled to the associated femur and tibia bones, respectively.

DETAILED DESCRIPTION OF THE DRAWINGS

Figure 1:
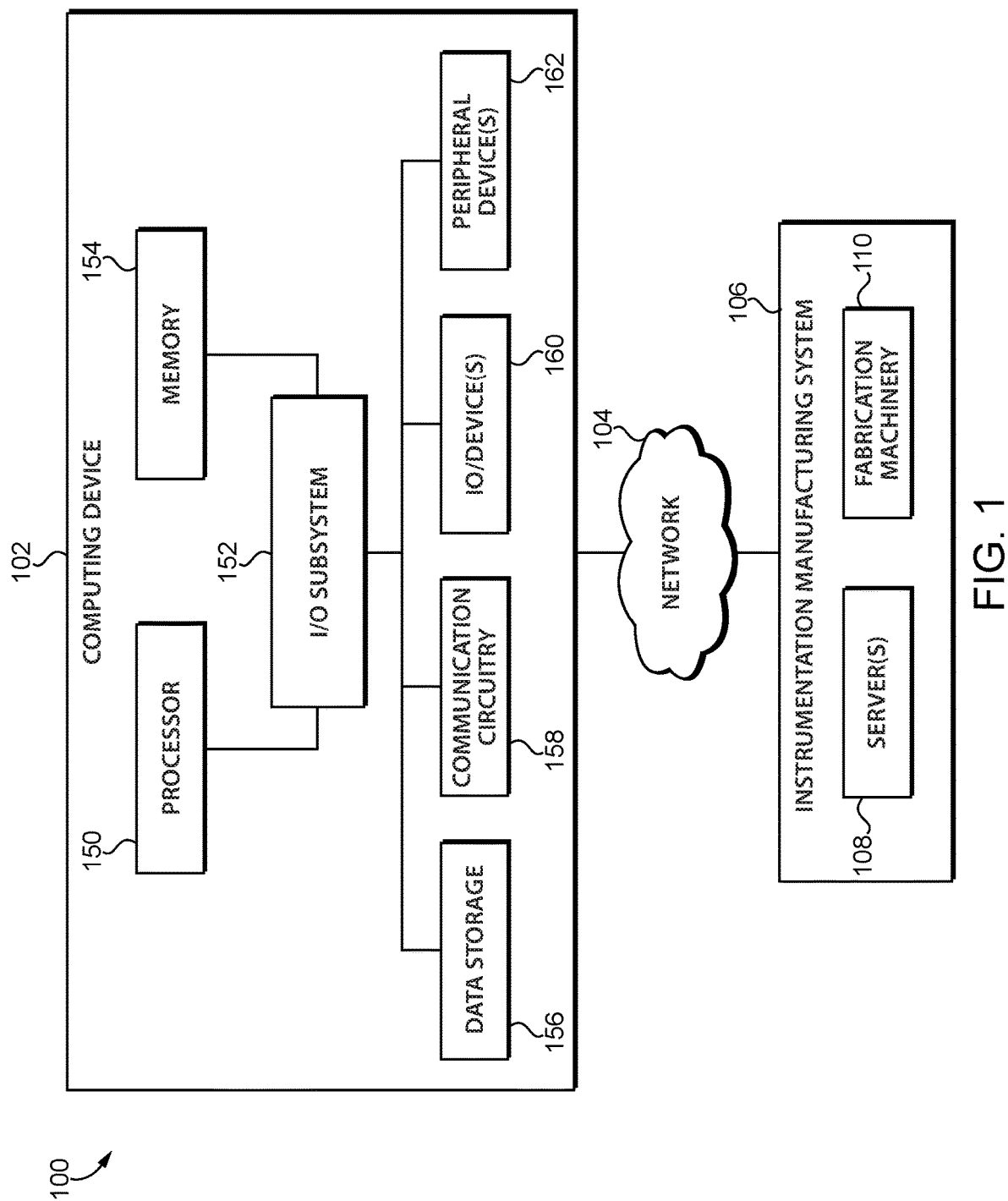
FIG. 1 is a simplified block diagram of a system for adaptive surgeon-specific surgical instrumentation.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in the illustrative embodiment, a system 100 for adaptive surgeon-specific surgical instrumentation includes a computing device 102, a network 104, and an instrumentation manufacturing system 106. Further, as shown, the illustrative instrumentation manufacturing system 106 includes one or more servers 108 and fabrication machinery 110.

As described in detail below, the system 100 allows the surgeon to design various features of the surgical instrumentation (e.g., tibial and femoral cutting guides) such that the resultant surgical instrumentation is tailored to the surgeon based, for example, on the surgeon's specific techniques and/or preferences. As such, the system 100 may provide the surgeon direct control (e.g., by virtue of surgeon input provided through a graphical user interface) over how the surgical instrumentation will function and interact with the surgeon. For example, in some embodiments, the surgeon may indicate whether one or more of the tibial paddles of a surgeon-specific tibial cutting guide will have a contact extension, which can affect how the surgeon interacts with the guide. As such, the surgeon's design choice may impute both a physical and functional change to the surgical instrumentation and/or procedure. Similarly, the surgeon may provide input regarding the profile/shape of a tibial cutting guide such as, for example, whether the cutting guide should have a streamlined profile (e.g., for a tibial cut first surgical technique) or a more traditional/bulky profile (e.g., for a distal cut first surgical technique).

It should be appreciated that the surgeon-specific surgical instrumentation designed by the surgeon using the system 100 enables greater flexibility without the added inventory or complexity. The system 100 may permit the surgeon to select the necessary surgical instruments in a "to-order" or "just-in-time" approach based on the surgeon's technique and preferences, patient data, and/or other relevant parameters. Further, the surgeon-specific surgical instrumentation may allow the surgical procedure to proceed more quickly with a reduced probability of infection, vascular damage, wear debris, and/or the need to recut. The surgeon-specific surgical instrumentation may reduce the likelihood of suboptimal implant placement, which can reduce implant life and increase the risk of revision. Additionally, the surgeon-specific surgical instrumentation may also maximize the chances of preserving host bone and/or ensure that revision surgeries are performed more easily.

The computing device 102 may be embodied as any type of computing device capable of performing the functions described herein. For example, the computing device 102 may be embodied as a desktop computer, laptop computer, tablet computer, notebook, netbook, Ultrabook™, cellular phone, smartphone, wearable computing device, personal digital assistant, mobile Internet device, Internet of Things (IoT) device, server, router, switch, and/or any other computing/communication device capable of performing the functions described herein. As shown in FIG. 1, the illustrative computing device 102 includes a processor 150, an input/output ("I/O") subsystem 152, a memory 154, a data storage 156, a communication circuitry 158, one or more I/O devices 160, and one or more peripheral devices 162. Of course, the computing device 102 may include other or additional components, such as those commonly found in a typical computing device (e.g., various input/output devices and/or other components), in other embodiments. Additionally, in some embodiments, one or more of the illustrative components may be incorporated in the processor 150 in some embodiments. Although a single computing device 102 is illustratively shown, it should be appreciated that one or more of the components of the computing device 102 described herein may be distributed across multiple computing devices. In other words, the techniques described herein may be employed by a computing system that includes one or more computing devices.

The processor 150 may be embodied as any type of processor capable of performing the functions described herein. For example, the processor 150 may be embodied as a single or multi-core processor(s), digital signal processor, microcontroller, or other processor or processing/controlling circuit. Similarly, the memory 154 may be embodied as any type of volatile or non-volatile memory or data storage capable of performing the functions described herein. In operation, the memory 154 may store various data and software used during operation of the computing device 102, such as operating systems, applications, programs, libraries, and drivers. The memory 154 is communicatively coupled to the processor 150 via the I/O subsystem 152, which may be embodied as circuitry and/or components to facilitate input/output operations with the processor 150, the memory 154, and other components of the computing device 102. For example, the I/O subsystem 152 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 152 may form a portion of a system-on-a-chip (SoC) and be incorporated, along with the processor 150, the memory 154, and other components of the computing device 102, on a single integrated circuit chip.

The data storage 156 may be embodied as any type of device or devices configured for short-term or long-term storage of data such as, for example, memory devices and circuits, memory cards, hard disk drives, solid-state drives, or other data storage devices. The data storage 156 and/or the memory 154 may store various data during operation of the computing device 102 useful for performing the functions described herein.

The communication circuitry 158 may be embodied as any communication circuit, device, or collection thereof, capable of enabling communications between the computing device 102 and other remote devices (e.g., the instrumentation manufacturing system 106, the server 108, etc.) over a network (e.g., the network 104). The communication circuitry 158 may be configured to use any one or more communication technologies (e.g., wireless or wired communications) and associated protocols (e.g., Ethernet, Bluetooth®, WiMAX, etc.) to effect such communication.

The I/O devices 160 may include any number of devices configured to receive input data from a surgeon and/or other user (i.e., input devices) and any number of devices configured to output data to the surgeon and/or other user (i.e., output devices). The particular devices included in the I/O devices 160 may depend on, for example, the type and/or intended use of the computing device 102. For example, in some embodiments, the I/O devices 160 may include a display device on which a graphical user interface (see, e.g., the graphical user interface 300 of FIGS. 3-4) can be displayed for the surgeon. Further, the I/O devices 160 may include an input device that allows the surgeon to select various options presented on the graphical user interface. For example, in some embodiments, the input device may be embodied as a keyboard, mouse, touchscreen display, and/or microphone. In particular, in some embodiments, it should be appreciated that the computing device 102 may be embodied as a tablet computer, smartphone, or other computing device having a touchscreen display that serves to both receive input from the surgeon/user and provide output to the surgeon/user.

The peripheral devices 162 may include any number of additional peripheral or interface devices, such as speakers, microphones, additional storage devices, and so forth. The particular devices included in the peripheral devices 162 may depend on, for example, the type and/or intended use of the computing device 102. For example, in some embodiments, the peripheral devices 162 may include a keyboard, mouse, display, touchscreen display, printer, alarm, status indicator, handheld device, diagnostic tool, and/or one or more other suitable peripheral devices.

It should be appreciated that one or more software applications may be executed by the processor 150 to display the graphical user interface (e.g., the graphical user interface 300 of FIGS. 3-4) on the I/O device(s) 160 and receive the relevant surgeon input regarding the desired parameters of the surgeon-specific surgical instrumentation. The application(s) may be embodied as any suitable application(s) for performing the functions described herein. For example, depending on the particular embodiment, the application may be embodied as a mobile application (e.g., a smartphone application), a cloud-based application, a web application, a thin-client application, and/or another suitable type of application. In some embodiments, the application may serve as a client-side user interface (e.g., via a web browser) for a web-based application or service (e.g., of the server(s) 108).

The network 104 may be embodied as any type of communication network capable of facilitating communication between the computing device 102 and remote devices (e.g., the instrumentation manufacturing system 106, the server(s) 108, etc.). As such, the network 104 may include one or more networks, routers, switches, computers, and/or other intervening devices. For example, the network 104 may be embodied as or otherwise include one or more cellular networks, telephone networks, local or wide area networks, publicly available global networks (e.g., the Internet), ad hoc networks, short-range communication links, or a combination thereof.

The instrumentation manufacturing system 106 may be embodied as any collection of one or more devices, components, and/or systems configured to perform the functions described herein. As shown, the illustrative instrumentation manufacturing system 106 includes one or more servers 108 and fabrication machinery 110. However, it should be appreciated that the instrumentation manufacturing system 106 may include additional and/or alternative devices, components, and/or systems in other embodiments. Similarly, one or more of the devices, components, and/or systems of the instrumentation manufacturing system 106 described herein may be omitted in other embodiments. Depending on the particular embodiment, the various devices, components, and/or systems of the instrumentation manufacturing system 106 may be co-located, or may be distributed across various locations.

Each of the one or more servers 108 may be embodied as any type of computing device capable of performing the functions described herein. For example, each server 108 may be embodied as a server, desktop computer, laptop computer, tablet computer, notebook, netbook, Ultrabook™, cellular phone, smartphone, wearable computing device, personal digital assistant, mobile Internet device, Internet of Things (IoT) device, router, switch, and/or any other computing/communication device capable of performing the functions described herein. In some embodiments, one or more of the servers 108 may be similar to the computing device 102 described above. As such, the components of the server(s) 108 may be similar to the components of the computing device 102 described above and, therefore, the descriptions have not been repeated herein for clarity of the description. Further, it should be appreciated that the server(s) 108 may include other components, sub-components, and/or devices commonly found in a computing device, which are not discussed herein for clarity of the description. Additionally, in some embodiments, one or more of the components of the computing device 102 may be omitted from one or more of the servers 108 (e.g., the peripheral devices 162). It should be appreciated that, although the server(s) 108 are described herein as one or more computing devices outside of a cloud computing environment, in other embodiments, the server(s) 108 may be embodied as a cloud-based device or collection of devices.

The fabrication machinery 110 may be embodied as any type of machinery capable of manufacturing/fabricating the surgeon-specific surgical instrumentation and otherwise performing the functions described herein. In some embodiments, it should be appreciated that the surgeon-specific surgical instruments may be fabricated on an "as requested" and/or "just-in-time" basis based on the surgeon input. Further, in some embodiments, the surgeon-specific surgical instruments may also be patient-specific (e.g., having contours adapted to match the contours of the patient's bony anatomy). However, in some embodiments, there may be a finite number of possible surgeon-specific surgical instruments based on a finite number of possible combinations of surgeon input data via the graphical user interface. In such embodiments, every possible adaptive surgeon-specific surgical instrument may be manufactured and stored (e.g., by the manufacturer and/or at a remote inventory facility). For example, the surgeon-specific tibial cutting guides corresponding with every possible combination of adaptive tibial guide parameters and/or the surgeon-specific femoral cutting guides corresponding with every possible combination of adaptive femoral guide parameters may be manufactured and stored. In yet another embodiment, the more common surgical instruments may be stored and the less common surgeon-specific surgical instruments may be manufactured on an "as requested" basis.

Although only one computing device 102, one network 104, and one instrumentation manufacturing system 106 are shown in the illustrative embodiment of FIG. 1, the system 100 may include multiple computing device 102, multiple networks 104, and/or multiple instrumentation manufacturing systems 106 in other embodiments.

Figure 2:
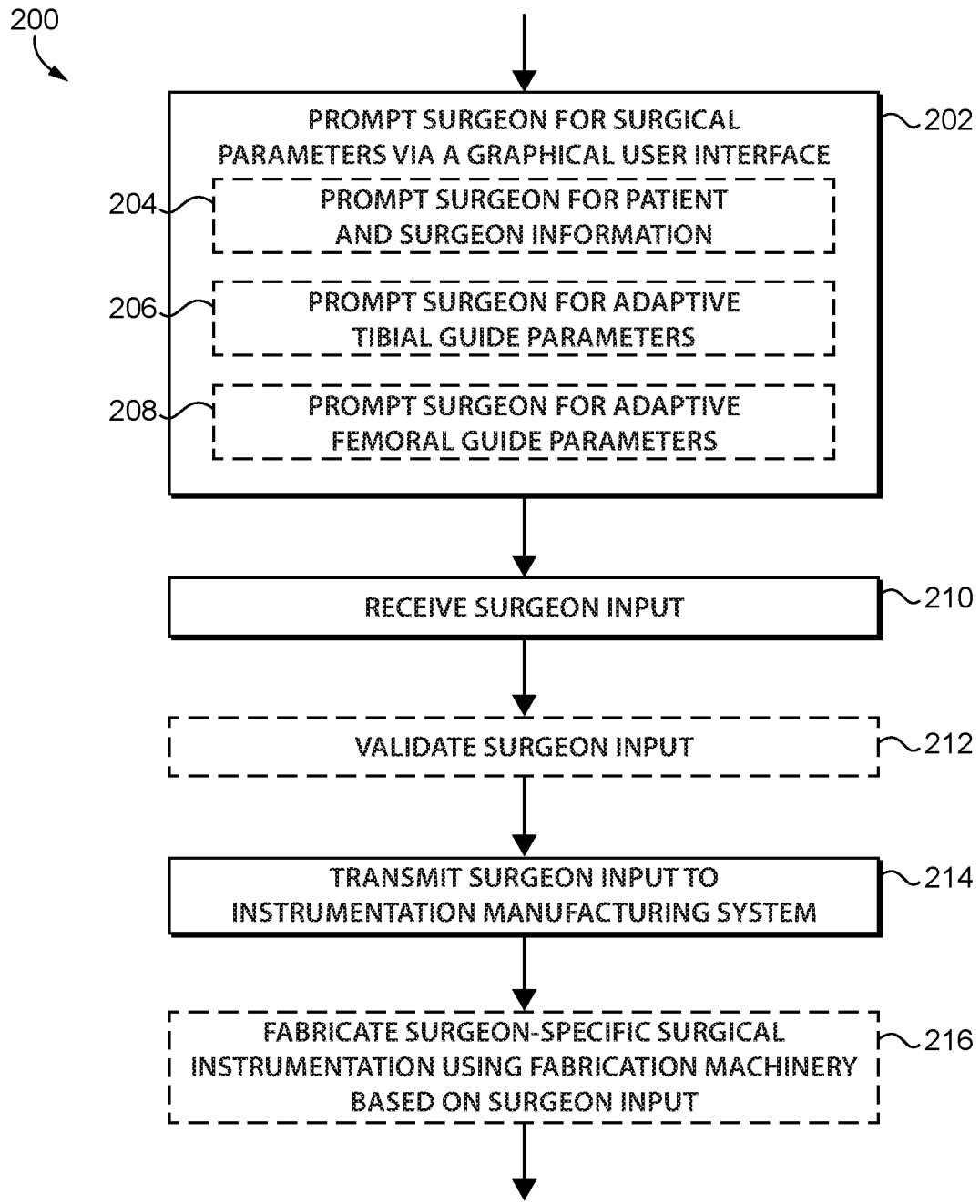
FIG. 2 is a simplified flow diagram of at least one embodiment of a method for identifying surgeon-specific surgical instrumentation based on surgeon input.

Referring now to FIG. 2, in use, the system 100 may execute a method 200 for identifying surgeon-specific surgical instrumentation based on surgeon input. It should be appreciated that the particular blocks of the method 200 are illustrated by way of example, and such blocks may be combined or divided, added or removed, and/or reordered in whole or in part depending on the particular embodiment, unless stated to the contrary. The illustrative method 200 begins with block 202 in which the computing device 102 prompts the surgeon/user for patient and surgical parameters via a graphical user interface (e.g., presented on a display device). In particular, in block 204, the computing device 102 may prompt the surgeon/user for patient information and surgeon information (e.g., surgeon-identifying information). For example, the patient information may include patient-identifying information (e.g., name, unique identifier, birthdate, etc.), relevant patient/surgical parameters (e.g., prospective implant type, manufacturer, model, etc.), anthropometric data, image data (e.g., x-ray images, Mill images, CT images, ultrasound images, and/or other suitable bone images), and/or other relevant patient information. In some embodiments, instead of prompting the surgeon/user for such data, a portion (or the entirety) of the patient information and surgeon information may be received from another computing device or retrieved from the memory 154 or data storage 156 of the computing device 102.

Figure 3:
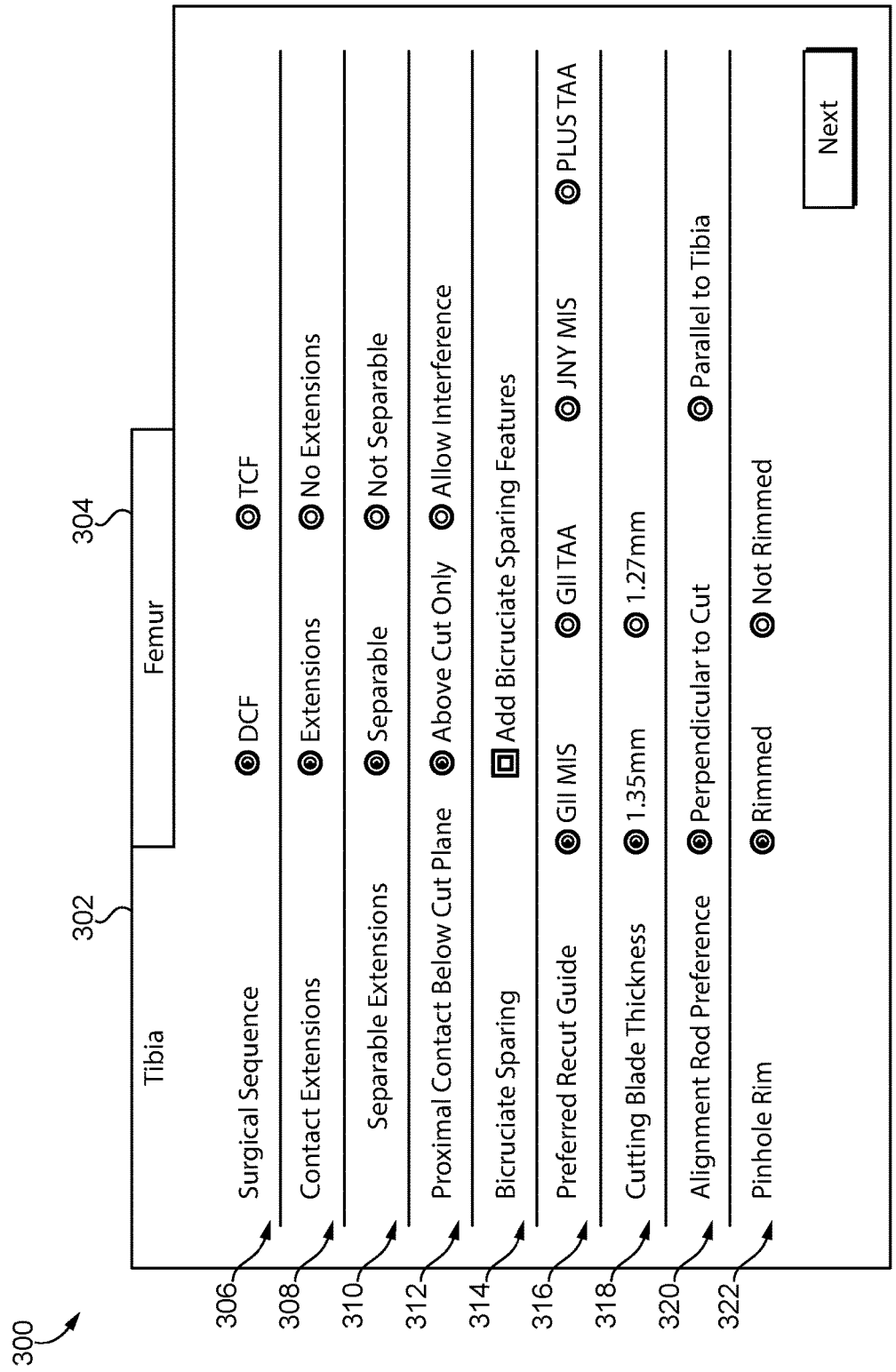
FIGS. 3-4 are simplified diagrams of a graphical user interface that may be displayed by the computing device of FIG. 1.
Figure 4:
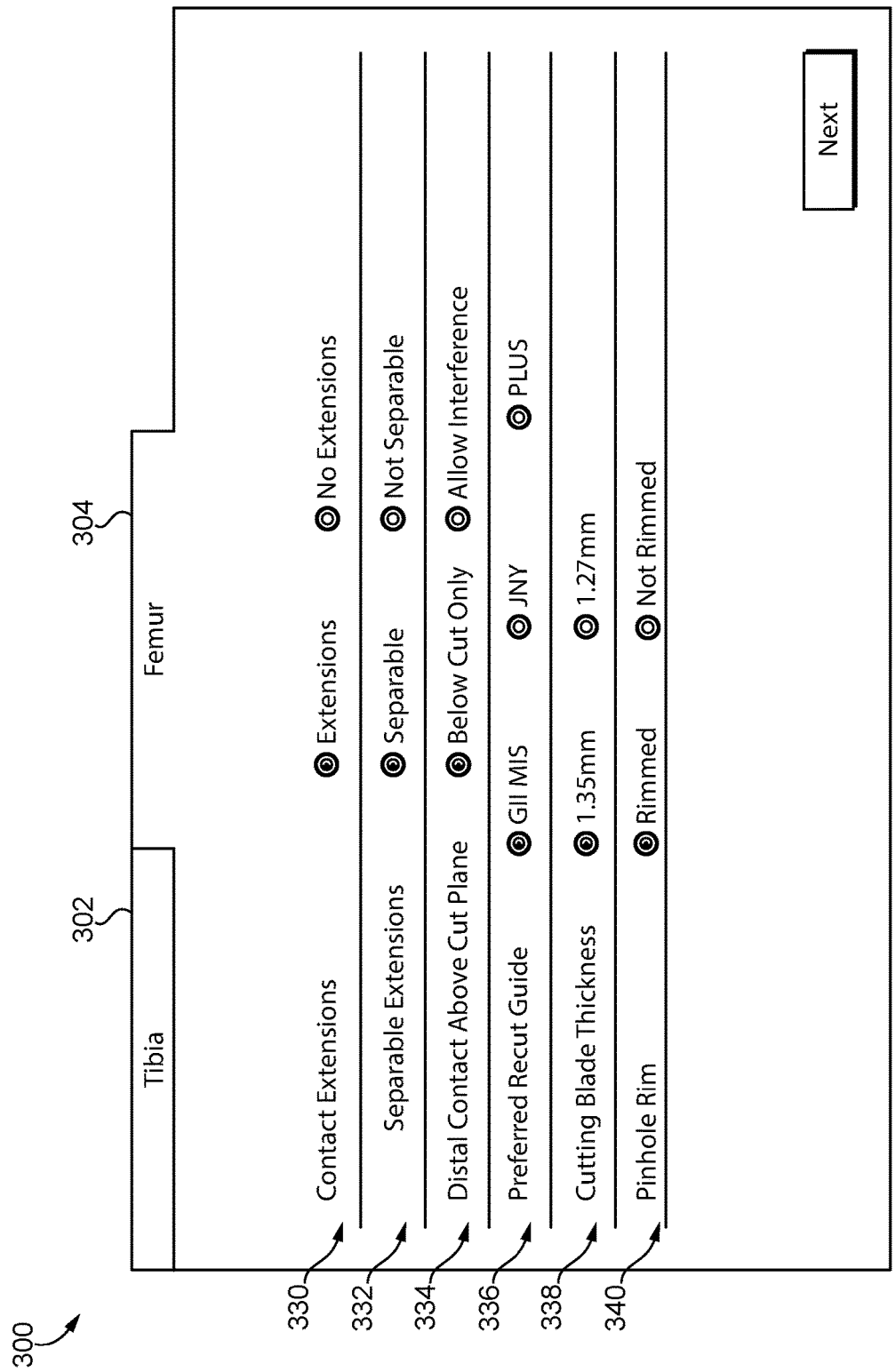

As indicated above, it should be appreciated that the surgeon may provide input regarding the surgeon's technique and/or preferences with respect to a prospective surgery (e.g., a total knee replacement surgery). In particular, the surgeon may provide various design parameters associated with the physical structure of the relevant surgical instruments. As such, in block 206, the computing device 102 may prompt the surgeon for adaptive tibial guide parameters, which may be collectively indicative of the physical structure of the surgeon-specific tibial cutting guide to be used by the surgeon (see, for example, the graphical user interface 300 as depicted in FIG. 3). Further, in block 208, the computing device 102 may prompt the surgeon for adaptive femoral guide parameters, which may be collectively indicative of the physical structure of the surgeon-specific femoral cutting guide to be used by the surgeon (see, for example, the graphical user interface 300 as depicted in FIG. 4). Although the surgeon-specific surgical instrumentation is described herein in reference to the surgeon-specific tibial cutting guide and the surgeon-specific femoral cutting guide, it should be appreciated that the techniques may be applied to other surgical instruments in other embodiments.

In block 210, the computing device 102 receives the surgeon input (e.g., via the graphical user interface and/or the I/O device 160) associated with the relevant design parameters for the surgical instrumentation. In particular, in the illustrative embodiment, the computing device 102 receives the surgeon input associated with the adaptive tibial guide parameters and the adaptive femoral guide parameters.

In some embodiments, in block 212, the computing device 102 may validate the surgeon input. For example, in some embodiments, the computing device 102 may confirm that the surgeon input for a particular design parameter is acceptable (e.g., a value selected from a predefined set of options, a value within acceptable design thresholds, etc.) depending on the particular circumstances. Further, in some embodiments, the computing device 102 may confirm that the surgeon input (e.g., the adaptive tibial/femoral guide parameters) is consistent with the anatomy of the patient. For example, in some embodiments, the computing device 102 may only allow a tibial paddle to interfere with the cut plane if the patient's proximal tibia is significantly damaged.

In block 214, the computing device 102 transmits the received (and, in some embodiments, validated) surgeon input to the instrumentation manufacturing system 106. In particular, in some embodiments, the surgeon input may be transmitted to one or more of the servers 108.

In block 216, the surgeon-specific surgical instrumentation is fabricated using the fabrication machinery 110 of the instrumentation manufacturing system 106 based on the surgeon input. In particular, in the illustrative embodiment, the fabrication machinery 110 may be used to fabricate a surgeon-specific tibial cutting guide based on the adaptive tibial guide parameters provided by the surgeon and/or a surgeon-specific femoral cutting guide based on the adaptive femoral guide parameters provided by the surgeon. As described above, in some embodiments, the surgeon-specific surgical instrumentation may be fabricated according to a "to order" or "just-in-time" approach, whereas in other embodiments, the surgeon-specific surgical instrumentation may be prefabricated and selected to correspond with the parameters provided in the surgeon input.

Although the blocks 202-216 are described in a relatively serial manner, it should be appreciated that various blocks of the method 200 may be performed in parallel in some embodiments.

Referring now to FIGS. 3 and 4, as indicated above, the computing device 102 may utilize a graphical user interface 300 to convey information to the surgeon, prompt the surgeon for input, and/or to receive surgeon input. As shown, the graphical user interface 300 identifies numerous categories of design parameters associated with a surgeon-specific tibial cutting guide and a surgeon-specific femoral cutting guide and prompts the surgeon for the associated inputs and selections. In particular, in the illustrative embodiment, the graphical user interface 300 includes a tibia tab 302 that, when selected/activated as shown in FIG. 3, prompts the surgeon for associated inputs for various adaptive tibial guide parameters. The graphical user interface 300 also includes a femur tab 304 that, when selected/activated as shown in FIG. 4, prompts the surgeon for associated inputs for various adaptive femoral guide parameters. Although each of the adaptive tibial and femoral guide parameters is shown as a selection of discrete options in the illustrative graphical user interface 300, in other embodiments, a graphical user interface may otherwise prompt the surgeon for parameter inputs (e.g., via an alphanumeric input field). For example, in an embodiment, the graphical user interface may permit the surgeon to enter a blade thickness (or length) in millimeters, micrometers, and/or other suitable unit of measure, which may be validated as described above.

As described herein, it should be appreciated that the various adaptive tibial and femoral guide parameters selected by the surgeon may affect the physical structure and function of the corresponding surgeon-specific cutting guides. Although specific adaptive tibial and femoral guide parameters (and options thereof) are described in reference to the graphical user interface 300, it should be appreciated that the graphical user interface 300 may include other adaptive tibial guide parameters, other adaptive femoral guide parameters, other options for the adaptive tibial guide parameters, and/or other options for the adaptive femoral guide parameters in addition to or in the alternative to the parameters and options described herein by way of example. For example, in some embodiments, the graphical user interface 300 may prompt the surgeon for an indication of the size of the pinholes, the length of the pins, and/or the depth at which the pins can be driven.

As shown in FIG. 3, when the tibia tab 302 is active, the illustrative graphical user interface 300 prompts the surgeon to select a surgical sequence 306 (viz., distal cut first (DCF) or tibial cut first (TCF)), whether the surgeon-specific tibial cutting guide includes contact extensions 308 and whether the contact extensions are separable 310, whether the surgeon-specific tibial cutting guide has proximal contact below the cut plane 312, whether the surgeon-specific tibial cutting guide has a bicruciate sparing feature 314, a preferred tibial recut guide 316 (viz., GENESIS™ II MIS, GENESIS™ II TAA, JOURNEY™ II MIS, or TC-PLUS™ TAA), a cutting blade thickness 318 (viz., 1.35 mm or 1.27 mm), an alignment rod preference 320 (viz., perpendicular to cut or parallel to tibia), and whether the surgeon-specific tibial cutting guide has rimmed pinholes 322. As shown in FIG. 4, when the femur tab 304 is active, the graphical user interface 300 prompts the surgeon to select whether the surgeon-specific femoral cutting guide includes contact extensions 330 and whether the contact extensions are separable 332, whether the surgeon-specific femoral cutting guide has distal contact above the cut plane 334, a preferred femoral recut guide 336 (viz., GENESIS™ II, JOURNEY™, or TC-PLUS™), a cutting blade thickness 338 (viz., 1.35 mm or 1.27 mm), and whether the surgeon-specific femoral cutting guide has rimmed pinholes 340. Although the illustrative graphical user interface 300 specifically identifies various GENESIS™, JOURNEY™, and TC-PLUS™ recut guides, it should be appreciated that, in other embodiments, recut guides having similar features to those guides may be identified (e.g., by name or by prevalent feature(s)) as options. Further, in other embodiments, the graphical user interface 300 may identify for selection one or more other recut guides suitable for performing the functions described herein (e.g., recut guides manufactured by Smith & Nephew®, Zimmer Biomet, Stryker, DePuy Orthopaedics, and/or another manufacturer). Various structural and/or functional implications of the graphical user interface 300 selections indicated above are described in further detail below.

Referring now to FIGS. 5-7, the surgeon may select a distal cut first (DCF) surgical technique or a tibial cut first (TCF) surgical technique. FIG. 5 depicts various features of a surgeon-specific tibial cutting guide 500 used with a DCF technique, whereas FIGS. 6-7 depict various features of the guide 500 used with a TCF technique. FIG. 6 shows the guide 500 with the knee joint in flexion, and FIG. 7 shows the guide 500 with the knee joint in extension. It should be appreciated that DCF is a surgical technique in which the distal femur 502 is cut first to open the joint space for more visibility and maneuverability, whereas TCF is a surgical technique in which the proximal tibia 504 is cut first to provide a foundation for subsequent cuts and measurements and/or to simplify balancing of the amount of bone removed from the femur, which is nontrivial due, for example, to kinematics and soft tissue factors.

As shown in FIG. 5, if the DCF technique is used, the pinholes 506 on the tibial paddles 508 of the surgeon-specific tibial cutting guide 500 may be angled vertically (e.g., perpendicular to a proximal surfaces 510 of the paddles 508), because the pinholes 506 will not interfere with the already-resected femur. However, with the TCF technique, there is limited joint space within which to operate. Accordingly, as shown in FIGS. 6-7, if the TCF technique is used, the profile of the surgeon-specific tibial cutting guide 500 is lower/thinner. In particular, the transition 511 of the tibial paddles 508 to the thinner tibial contact portion 513 may occur more anteriorly with the TCF technique than with the DCF technique, which may result in a higher proportion of the thinner tibial contact portion 513 length relative to the overall anterior-posterior dimension of the guide 500. As such, in some embodiments, the TCF-designed guide may have less posterior thickness than a DCF-designed guide. Further, in some embodiments, selecting the TCF technique may cause the pinholes 506 to be shifted anteriorly and/or angled anteriorly relative to the proximal surfaces 510 of the paddles 508. In some embodiments, a thickness 512 of the tibial paddles 508 used with the TCF technique may be less than a standard thickness 514 as used with the DCF technique. In other embodiments, it should be appreciated that the surgeon may include design parameters such that the guide 500 is a low profile (thin) guide and/or has angled/shifted pinholes 506 even when a DCF technique is employed.

Referring now to FIGS. 8-11, the surgeon may indicate that one or both of the tibial paddles 508 of the surgeon-specific tibial cutting guide 500 is to include a contact extension 516 and/or that one or both of the femoral paddles 602 of the surgeon-specific femoral cutting guide 600 is to include a contact extension 604. It should be appreciated that the surgeon may select to include the contact extension(s) 516 and/or the contact extension(s) 604 if the surgeon prefers more contact area with the proximal tibia 504 or the distal femur 502, respectively, whereas the surgeon may omit the contact extension(s) 516 and/or the contact extension(s) 604 if the surgeon prefers more visibility in the joint space.

Figure 12:
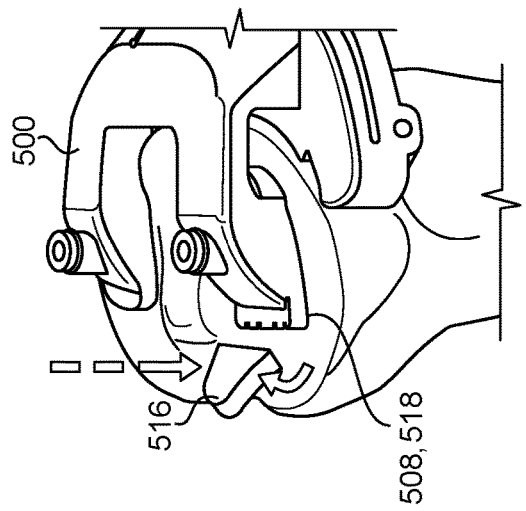
FIG. 12 is a side view of a surgeon-specific tibial cutting guide with a separable tibial paddle contact extension that illustrates the contact extension being separated from the remainder of the tibial paddle.
Figure 9:
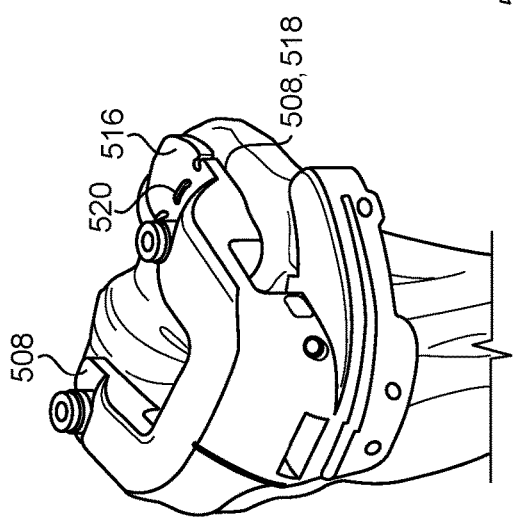
FIG. 9 is a perspective view of a surgeon-specific tibial cutting guide with a tibial paddle contact extension.
Figure 11:
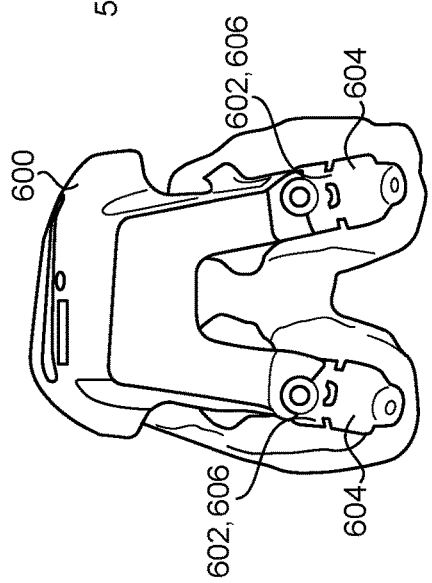
FIG. 11 is a perspective view of a surgeon-specific femoral cutting guide with a femoral paddle contact extension.
Figure 8:
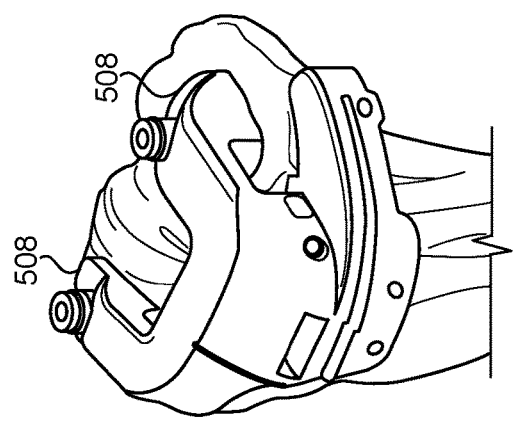
FIG. 8 is a perspective view of a surgeon-specific tibial cutting guide without a tibial paddle contact extension.
Figure 10:
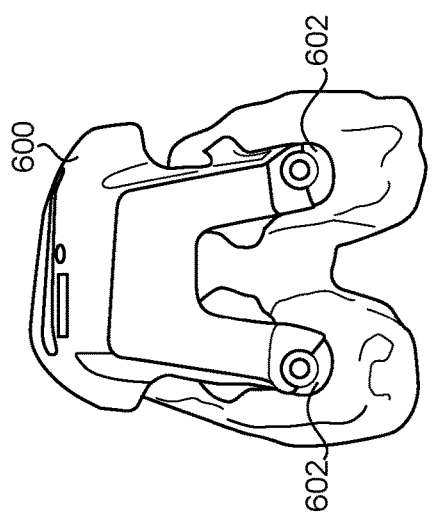
FIG. 10 is a perspective view of a surgeon-specific femoral cutting guide without a femoral paddle contact extension.

FIG. 8 depicts the surgeon-specific tibial cutting guide 500 without contact extensions 516, whereas FIG. 9 depicts the guide 500 with one contact extension 516. FIG. 10 depicts the surgeon-specific femoral cutting guide 600 without contact extensions 604, whereas FIG. 11 depicts the guide 600 with both contact extensions 604. Further, as described above and illustrated in FIG. 12, the surgeon may select whether each of the contact extension(s) 516 and/or the contact extension(s) 604 is separable from a remainder 518, 606 of the corresponding paddle 508, 602. It should be appreciated that each of the contact extensions 516 may be structured to be separable from the remainder 518 of the corresponding tibial paddle 508 according to any suitable technique. For example, in some embodiments, the contact extension 516 may have a perforation 520 or area of weakened volume/density to allow the surgeon to separate the contact extension 516 from the remainder 518 of the tibial paddle 508 with less force than would otherwise be required. Similarly, it should be appreciated that each of the contact extensions 604 may be structured to be separable from the remainder 606 of the corresponding femoral paddle 602 according to any suitable technique.

Referring now to FIGS. 13-18, in the illustrative graphical user interface 300, the surgeon may provide input regarding whether the tibial paddle(s) 508 should extend below the cut plane 522 of a cutting blade of a cutting instrument, which may result in at least temporary interference with the blade. As shown in FIG. 13, the surgeon may encounter a patient whose proximal tibia 504 is severely damaged or deformed. For example, one of the tibial articular surfaces may be worn down so much that the cutting blade could cut through one of the tibial paddles 508. As such, it may be advantageous to have a surgeon-specific tibial cutting guide 500 designed to extend below (i.e., distal to) the cut plane 522 to contact the proximal tibia 504 for support prior to pinning the guide 500. Accordingly, as shown in FIGS. 16-18, the surgeon-specific tibial cutting guide 500 may include a contact extension 524 that extends distally from the corresponding tibial paddle 508 and having a distal surface 526 that contacts the proximal tibia 504 for support thereon. Similar to the contact extensions 516, 604 described above, in some embodiments, the contact extension 524 may be separable from a remainder 528 of the tibial paddle 508 according to any suitable technique (e.g., perforations, weakened volume/density, etc.). For example, in some embodiments, the surgeon may utilize a surgeon-specific tibial cutting guide 500 having one or more contact extensions 524 to support the guide 500 while it is being stabilized and pinned to the tibia, and subsequently separate/remove the contact extension(s) 524 from the guide 500 prior to using the cutting blade. As shown in FIGS. 14 and 15, in other embodiments, neither of the tibial paddles 508 of the surgeon-specific tibial cutting guide 500 extends below (distal to) the cutting plane 522. As indicated above, it should be appreciated that the surgeon-specific cutting guides 500, 600 may also be patient-specific in some embodiments. As shown in FIG. 4, the surgeon may similarly provide input regarding whether the femoral paddle(s) 602 should extend above the corresponding cut plane to contact, for example, a severely damaged distal femur 502.

Figure 20:
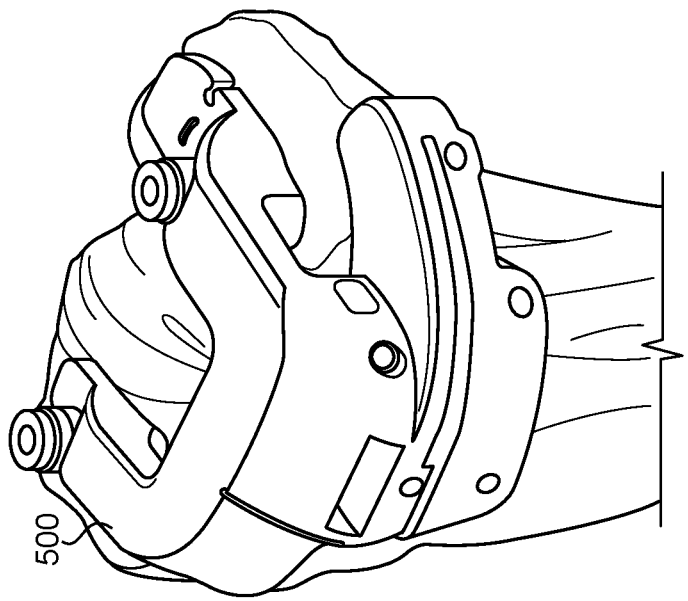
FIG. 20 is a perspective view of a surgeon-specific tibial cutting guide without a bicruciate ligament sparing feature.
Figure 19:
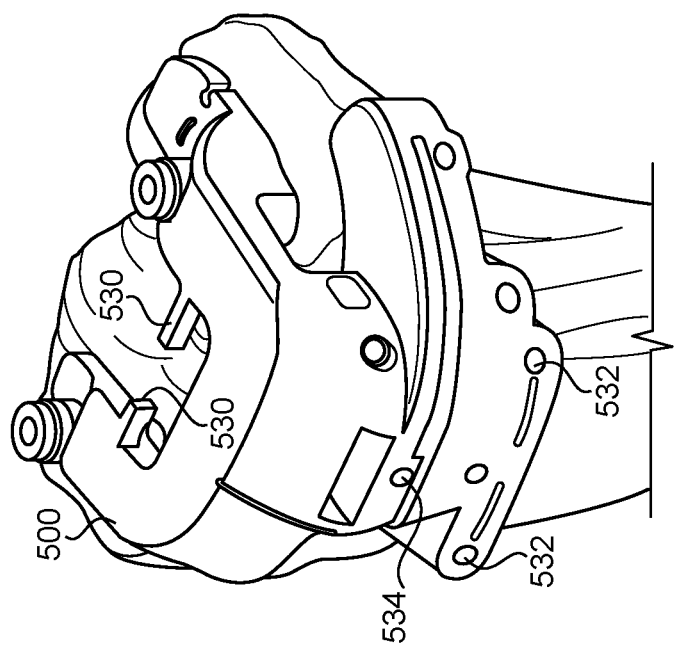
FIG. 19 is a perspective view of a surgeon-specific tibial cutting guide having a bicruciate ligament sparing feature.

Referring now to FIGS. 19 and 20, the surgeon may provide input regarding whether the surgeon-specific tibial cutting guide 500 should include one or more bicruciate ligament sparing features. For example, when the surgeon views the patient's bone images (e.g., x-ray images, MRI images, CT images, ultrasound images, and/or other suitable bone images), the surgeon may recognize that the cruciate ligaments are viable and may opt to design the surgeon-specific tibial cutting guide 500 to be more "anatomically friendly." Further, in some embodiments, one or more of those features may include the ability to place additional pins and/or marks on the patient's bone based on, for example, pre-operative imaging of the bone. In some embodiments, rotation, varus-valgus, depth, or all six degrees of freedom can be set using the designed guide 500. As shown in FIG. 19, the surgeon-specific tibial cutting guide 500 may include visual indicators 530 that assist in positioning the guide 500, additional anterior pinholes 532 that may be used as locators for a subsequent surgical cutting guide, and/or additional anterior pinhole 534 that may provide a hard stop for a proposed cut and/or serve as an alignment feature for subsequent surgical cutting guides. In some embodiments, based on the surgeon input, the surgeon-specific tibial cutting guide 500 may include one or more features of the guide 1200 described below with reference to FIGS. 45-50. FIG. 20 depicts the surgeon-specific tibial cutting guide 500 without the bicruciate ligament sparing features described herein.

Figure 39:
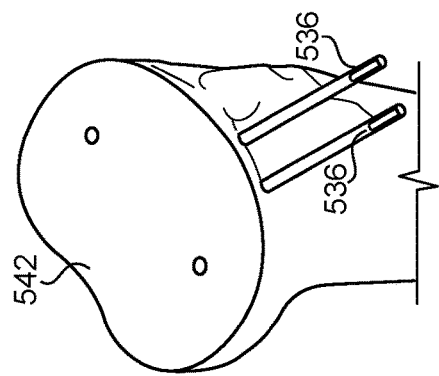
FIGS. 38-39 are perspective views of a patient's tibia before and after resection of the proximal tibia, respectively.
Figure 41:
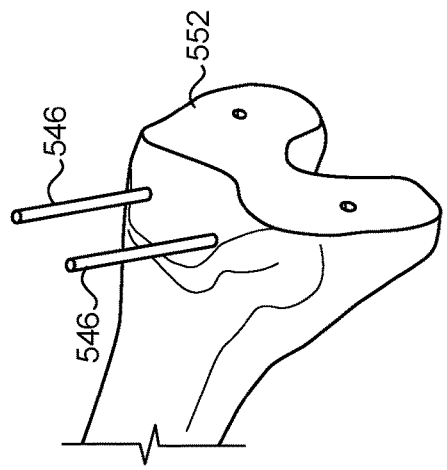
FIGS. 40-41 are perspective views of a patient's femur before and after resection of the distal femur, respectively.
Figure 38:
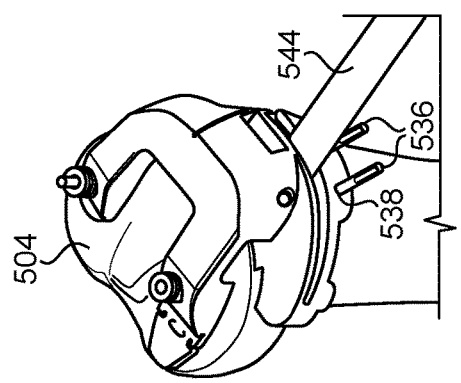
Figure 40:
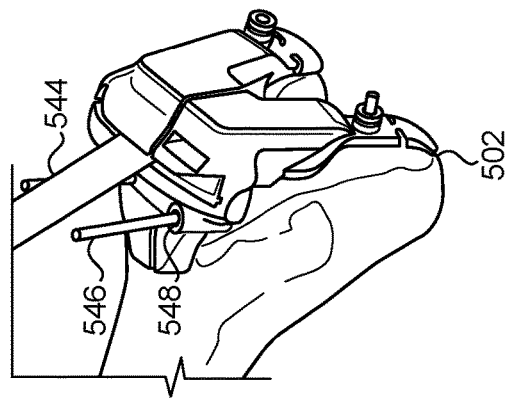

It should be appreciated that the surgeon-specific tibial cutting guide 500 and the surgeon-specific femoral cutting guide 600 may be designed based on the surgeon input to be used in conjunction with whichever surgical support instrumentation the surgeon prefers (e.g., standard surgical recut guides). In particular, the guides 500, 600 may be designed to cooperate with whichever tibial recut guide and/or femoral recut guide the surgeon prefers. As shown in FIGS. 38 and 39, in operation, the surgeon-specific tibial cutting guide 500 may be secured to the patient's tibia by two anterior pins 536 driven into anterior pinholes 538 (see also FIG. 5) of the guide 500 and, after resection of the proximal tibia 504 using the cutting blade 544 and removal of the guide 500, the pins 536 remain inserted into the tibia. Accordingly, in the illustrative embodiment, the surgeon-specific tibial cutting guide 500 may be designed such that the anterior pinholes 538 position the pins 536 in the proper locations such that the pins 536 can be inserted into corresponding recut guide pinholes 540 to secure the recut guide to the patient's already-resected tibia. Similarly, as shown in FIGS. 40 and 41, in operation, the surgeon-specific femoral cutting guide 600 may be secured to the patient's femur by two anterior pins 546 driven into anterior pinholes 548 of the guide 600 and, after resection of the distal femur 502 using the cutting blade 544 and removal of the guide 600, the pins 546 remain inserted into the femur. Accordingly, in the illustrative embodiment, the surgeon-specific femoral cutting guide 600 may be designed such that the anterior pinholes 548 position the pins 546 in the proper locations such that the pins 546 can be inserted into corresponding recut guide pinholes 550 to secure the recut guide to the patient's already-resected femur.

As indicated above, the illustrative graphical user interface 300 provides the surgeon with the GENESIS™ II MIS tibial recut guide 700 (see FIGS. 21A and 21B), GENESIS™ II TAA tibial recut guide 702 (see FIGS. 24A and 24B), JOURNEY™ II MIS tibial recut guide 704 (see FIGS. 25A and 25B), and TC-PLUS™ TAA tibial recut guide 706 (see FIGS. 23A and 23B) as options for the surgeon's preferred tibial recut guide. However, as described above, it should be appreciated that the graphical user interface 300 may present additional and/or alternative tibial recut guides in other embodiments. For example, the surgeon may further select from the JOURNEY™ MIS tibial recut guide 708 (see FIGS. 22A and 22B), the JOURNEY II XR™ tibial recut guide 710 (see FIGS. 26A and 26B), and/or other suitable tibial recut guides. It should be appreciated that each of the tibial recut guides 700-710 includes multiple sets of recut guide pinholes 540, which may be used to adjust the height and/or offset of the corresponding tibial recut guide relative to the resected tibial surface 542.

The illustrative graphical user interface 300 further provides the surgeon with the GENESIS™ II femoral recut guide 800 (see FIGS. 27A and 27B), JOURNEY™ femoral recut guide 802 (see FIGS. 28A and 28B), and the TC-PLUS™ femoral recut guide 804 as options for the surgeon's preferred femoral recut guide. However, as described above, it should be appreciated that the graphical user interface 300 may present additional and/or alternative femoral recut guides in other embodiments. It should be appreciated that each of the tibial recut guides 800-804 includes multiple sets of recut guide pinholes 550, which may be used to adjust the height and/or offset of the corresponding femoral recut guide relative to the resected femoral surface 552.

In some embodiments, it should be appreciated that the surgeon-specific tibial cutting guide 500 and/or the surgeon-specific femoral cutting guide 600 may have recut pinning modularity similar to the blocks 2100, 2102 described below with reference to FIGS. 51-59.

As described above, the surgeon input may include a thickness of the cutting blade 544 of a cutting instrument that the surgeon prefers or intends to use for the surgical procedure. For example, it should be appreciated that there is a tradeoff between the amount of vibration of the cutting blade 544 and its ease of use. That is, thicker cutting blades 544 tend to vibrate less but require more effort to use, whereas thinner cutting blades 544 vibrate more but require less effort to use. In the illustrative embodiment, the cutting slot of the surgeon-specific tibial guide 500, 600 is designed to harmonize with the surgeon's preferred cutting blade thickness. For example, using a thick blade in a thin slot can generate debris that is harmful to the patient. In some embodiments, it should be appreciated that the surgeon may select a cutting blade 544 for use with the surgeon-specific tibial cutting guide 500 with a different thickness than that selected for use with the surgeon-specific femoral cutting guide 600.

Figure 31:
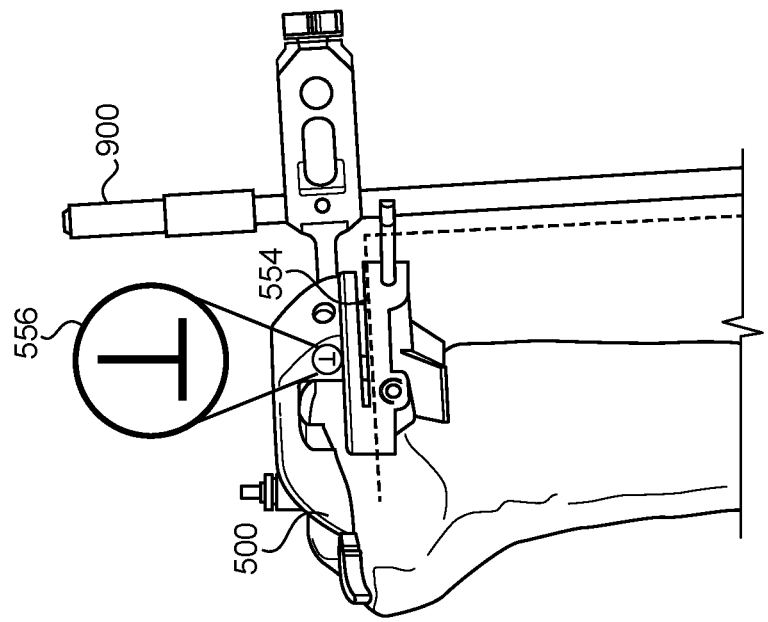
FIG. 31 illustrates a surgical technique in which the alignment rod is aligned perpendicular to the cutting slot of the surgeon-specific tibial cutting guide.
Figure 30:
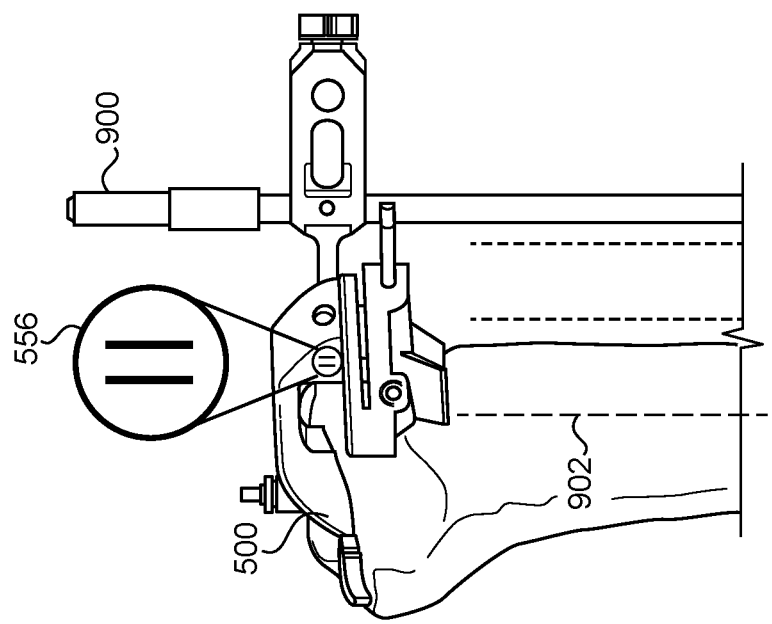
FIG. 30 illustrates a surgical technique in which the alignment rod is aligned parallel to the patient's mechanical axis.

Referring now to FIGS. 30 and 31, the surgeon may indicate (via the graphical user interface 300) an alignment rod preference for the surgical procedure. In particular, the surgeon may indicate whether the surgeon-specific tibial cutting guide 500 should be designed for use with the surgical technique illustrated in FIG. 30 in which an alignment rod 900 is aligned parallel to a mechanical axis 902 of the patient's tibia to gauge alignment, or the surgeon-specific tibial cutting guide 500 should be designed for use with the surgical technique illustrated in FIG. 31, in which the alignment rod 900 is aligned perpendicular to the cutting slot 554 of the guide 500. It should be appreciated that standard surgical instrumentation for many knee systems includes a built-in 3° to 10° posterior slope. As such, the parallel alignment technique described in reference to FIG. 30 allows the surgeon to perform the identical technique (i.e., ensure parallelism) regardless of the specific built-in posterior slope of the guide 500. However, if the surgeon desires more control over the posterior slope of the guide 500, the surgeon may opt for the perpendicular alignment technique described in reference to FIG. 31, which provides a reliable benchmark for the surgeon. In some embodiments, the surgeon-specific tibial cutting guide 500 may include a visual indicator 556 (e.g., marking, engraving, etc.) of the alignment technique for which the guide 500 is designed.

Figure 33:
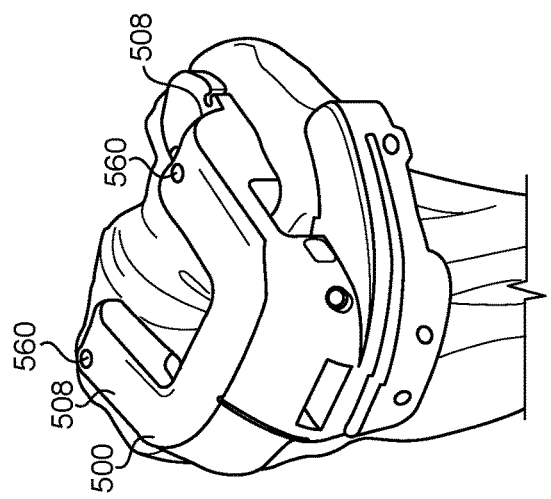
FIG. 33 is a perspective view of a surgeon-specific tibial cutting guide without rimmed proximal pinholes.
Figure 32:
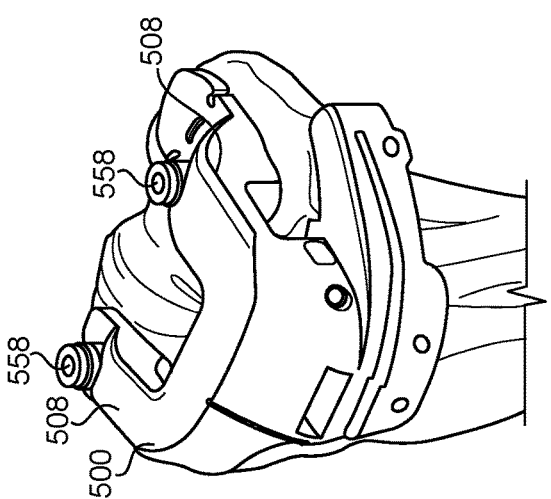
FIG. 32 is a perspective view of a surgeon-specific tibial cutting guide having rimmed proximal pinholes.

Referring now to FIGS. 32 and 33, the surgeon may indicate whether the tibial paddles 508 of the surgeon-specific tibial cutting guide 500 are to include rimmed pinholes 558. It should be appreciated that headed pins, for example, may be overdriven below the surface of the paddle 508 such that it is difficult to retrieve the pin. Carving out or otherwise extracting a deeply seated pin increases surgical time and may cause vascular damage and/or infection to the patient. As such, the surgeon may opt for a guide 500 with rimmed pinholes 558 to facilitate removal of overdriven pins as described below. However, the surgeon may not necessarily use headed pins and/or may find rimmed pinholes 558 uncomfortable to grip, in which case the surgeon may opt for a guide 500 with non-rimmed pinholes 560 (i.e., without rimmed pinholes). FIG. 32 depicts the surgeon-specific tibial cutting guide 500 with rimmed pinholes 558. FIG. 33 depicts the surgeon-specific tibial cutting guide 500 with non-rimmed pinholes 560.

Figure 35:
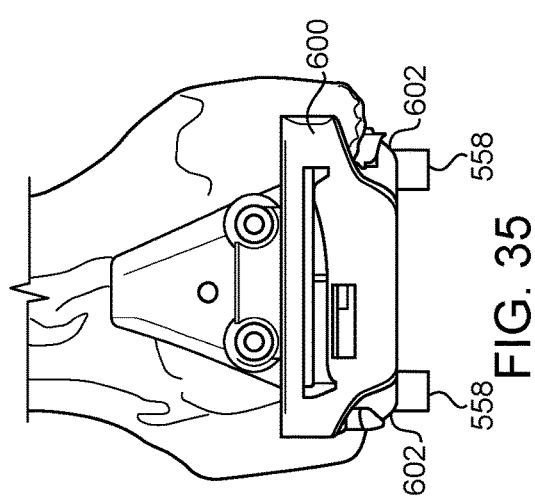
FIG. 35 is a perspective view of a surgeon-specific tibial femoral guide without rimmed distal pinholes.
Figure 34:
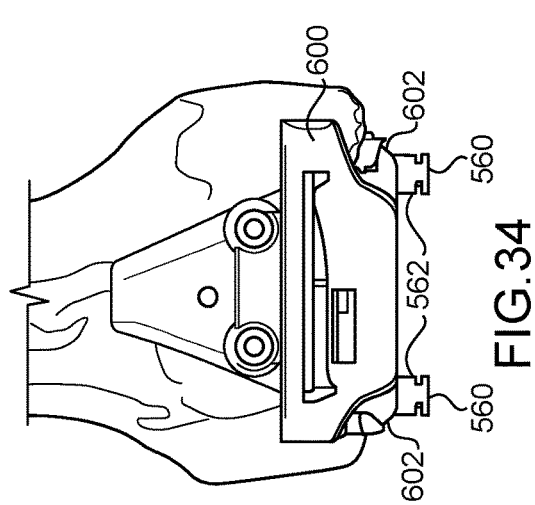
FIG. 34 is a perspective view of a surgeon-specific femoral cutting guide having rimmed distal pinholes.

Referring now to FIGS. 34 and 35, the surgeon may further indicate whether the femoral paddles 602 of the surgeon-specific femoral cutting guide 600 are to include rimmed pinholes 558 or non-rimmed pinholes 560. FIG. 34 depicts the surgeon-specific femoral cutting guide 600 with rimmed pinholes 558. FIG. 35 depicts the surgeon-specific femoral cutting guide 600 with non-rimmed pinholes 560. Although the non-rimmed pin-holes 560 of the surgeon-specific femoral cutting guide 600 are illustrated as having bosses 562 extending from the femoral paddles 602, it should be appreciated that the bosses 562 may be omitted such that the non-rimmed pinholes 560 terminate at the distal surface of the femoral paddles 602 in other embodiments (i.e., such that the non-rimmed pinholes 560 are flush with the femoral paddles 602). Likewise, in some embodiments, the non-rimmed pinholes 560 of the surgeon-specific tibial cutting guide 500 may include bosses similar to the bosses 562 in some embodiments.

Figure 36:
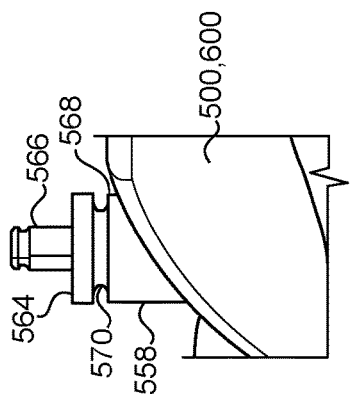
FIGS. 36-37 illustrate a rim portion of a rimmed pinhole being removed from the remainder of a guide boss.
Figure 37:
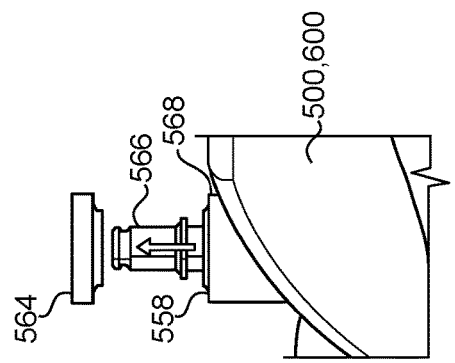

FIGS. 36 and 37 illustrate a rimmed portion 564 (e.g., a capture portion) of a rimmed pinhole 558 being removed to allow a surgeon to gain access to an overdriven pin 566. In particular, the rimmed pinhole 558 may generally include a boss portion 568 and the rimmed portion 564. Further, the rimmed portion 564 may be coupled to the boss portion 568 by a neck portion 570 that is sized to provide an undercut between the boss portion 568 and the rimmed portion 564. As depicted in FIG. 37, the recess or undercut provided by the neck portion 570 may be sized to receive a tool such as, for example, a rongeur to extract the rimmed portion 564. For example, the tool may be used to apply a force (e.g., a pulling or twisting force) to the rimmed portion 564 to separate the rimmed portion 564 from the boss portion 568, thereby gaining access to the overdriven pin 566 for removal thereof.

Figure 42:
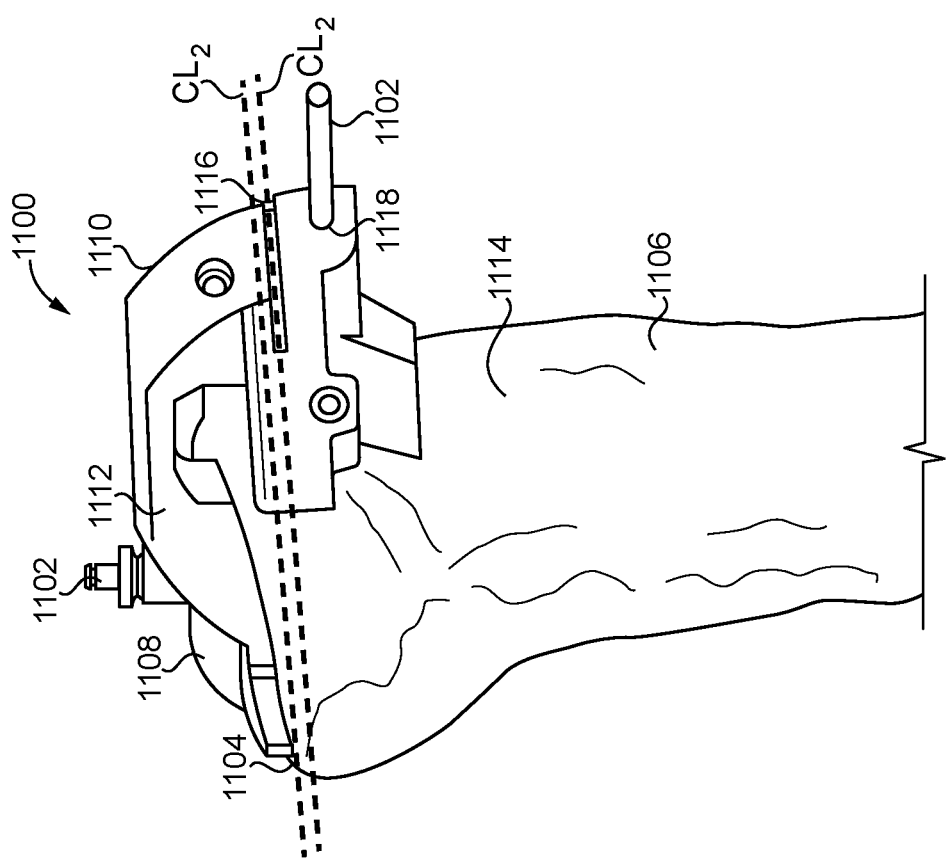
FIG. 42 illustrates a medial side view of an exemplary tibial cutting block operably secured via pins to a proximal end of a tibia.

FIG. 42 illustrates a medial side view of an exemplary tibial cutting block 1100 operably secured via one or more pins 1102 to a proximal end 1104 of a tibia 1106. FIG. 42 also depicts a portion of a tibial eminence 1108 at the proximal end 1104 of the tibia 1106. For at least some patients that undergo a knee implant procedure, the anterior and posterior cruciate ligaments may still be attached to the tibial eminence 1108. Thus, for at least some knee implant procedures, such as procedures in which the attachments of the anterior and posterior cruciate ligaments to the tibial eminence 1108 are intact, the exemplary tibial cutting block 1100 can be configured to at least assist in attempts to retain the tibial eminence 1108 and the associated attachments, while other generally adjacent portions of bone at the proximal end 1104 of the tibia 1106 is resected. Conversely, according to other procedures, including, for example, procedures in which the anterior and posterior cruciate ligaments are damage, the tibial cutting block 1100 can be configured the remove tibial eminence 1108, as well as the attached ligaments and adjacent bone, via resection of at least a portion of the proximal end 1104 of the tibia 1106.

The exemplary tibial cutting block 1100 depicted in FIG. 42 can include an anterior tibial portion 1110, a medial tibial paddle 1112, and a lateral tibial paddle (not shown). The anterior tibial portion 1110 can be configured to overly a portion of the anterior face 1114 of the tibia 1106. The medial tibial paddle 1112 can be configured to overly at least a portion of the medial plateau, while the lateral tibial paddle, which can have a configuration that is generally similar to that of the medial tibial paddle 1112, can be configured to overly at least portions of the lateral plateau of the tibia 1106. Further, although not illustrated, the anterior tibial portion 1110, medial tibial paddle 1112 and lateral tibial paddle of the tibial cutting block 1100 can include bone interfacing surfaces that are configured to interact with opposing portions of the proximal end 1104 of the tibia 1106, and/or interact with or otherwise accommodate associated cartilage at or around the tibia 1106.

The tibial cutting block 1100 can also include a cutting slot 1116 that is that is sized to receive insertion of a cutting blade that can cut or resect the tibia 1106. According to the illustrated embodiment, the cutting slot 1116 is oriented on the medial half of the anterior side of the tibial cutting block 1100. The cutting slot 1116 can be formed through the bone interfacing portions of the tibial cutting block 1100, or may be recessed from the bone interfacing surfaces. The thickness of the cutting slot 1116 can help direct the orientation of the cutting tool, such as, for example, a saw blade, as the cutting tool advances through the cutting slot 1116. Further, the translation of the cutting slot 1116 relative to the tibial cutting block 1100, can, according to at least certain cutting blocks, at least assist in setting a resection depth.

The tibial cutting block 1100 can include a plurality of pin holes 1118 that can each be configured to receive pins 1102 that are inserted and/or driven into a portion of the tibia 1106. At least some of the pin holes 1120 can receive pins 1118 that can be used to at least secure the tibial cutting block 1100 to the tibia 1106, while other pins 1120 that extend through the tibial cutting block 1100 can also, or alternatively, be used in connection with aligning a component of the implant system that will be implanted in the patient.

According to at least certain types of implant procedures, preparation of the bone for an implant component may involve cutting a portion of the bone. For example, as discussed above, the exemplary tibial cutting block 1100 can be positioned such that at least a portion of the bone is removed via operation of the cutting instrument in the cutting slot 1116. Further, the cutting slot 1116 may be positioned so that the cutting instrument is anticipated to cut the bone along a selected first cutting line (as indicated by "$CL_1$," in FIG. 42). Thus, when the cut bone is removed, a resected bone surface at of the tibia 1106 generally adjacent to, or directly beneath the first cut line, may be provide at, and/or across, the proximal end 1104 of the tibia 1106.

The shape and/or size of the tibia 1106, among other bones, is generally not uniform.

Further, with respect to the tibia 1106 for example, the size and/or shape of the tibia 1106 can vary in a non-uniform manner along at least the mechanical axis of the tibia 1106 in the distal-proximal direction. For at least certain patients and/or for at least certain bones, such lack of uniformity and associated variance in the size and/or shape of the tibia 1106 can, traditionally, result in a degree of unpredictability in at least the size and/or shape of the bone that remains at a cut or resected surface of the tibia 1106. Thus, for example, FIG. 42 illustrates a second cutting line (as indicated by "$CL_2$" in FIG. 42) that is linearly offset from the first cutting line $CL_1$ such that the second cutting line $CL_2$ is at a different cutting depth relative to the linear location of the first cutting line $CL_1$ about the proximal end 1104 of the tibia 1106.

In view of the non-uniformity in the shape and/or size of the tibia 1106, setting the cutting slot 1116 of the tibial cutting block 1100 at the second cutting line $CL_2$ could result in at least the resulting resected bone surface of the tibia 1106, and/or the remaining portion of the tibia 1106 around the cut or resected bone surface, having a different shape and/or size than the cut or resected bone surface that can result from cutting or resecting the tibia along the first cutting line $CL_1$. Further, the nature of the non-uniform variations in the shape and/or size of the bone, in this example the tibia 1106, can result in a degree of unpredictability as to the extent of the differences in the size and/or shape of the bone surface that will result from cutting or resecting the tibia 1106 along the first or second cut lines $CL_1$, $CL_2$, among other possible bone cut locations.

Figure 43:
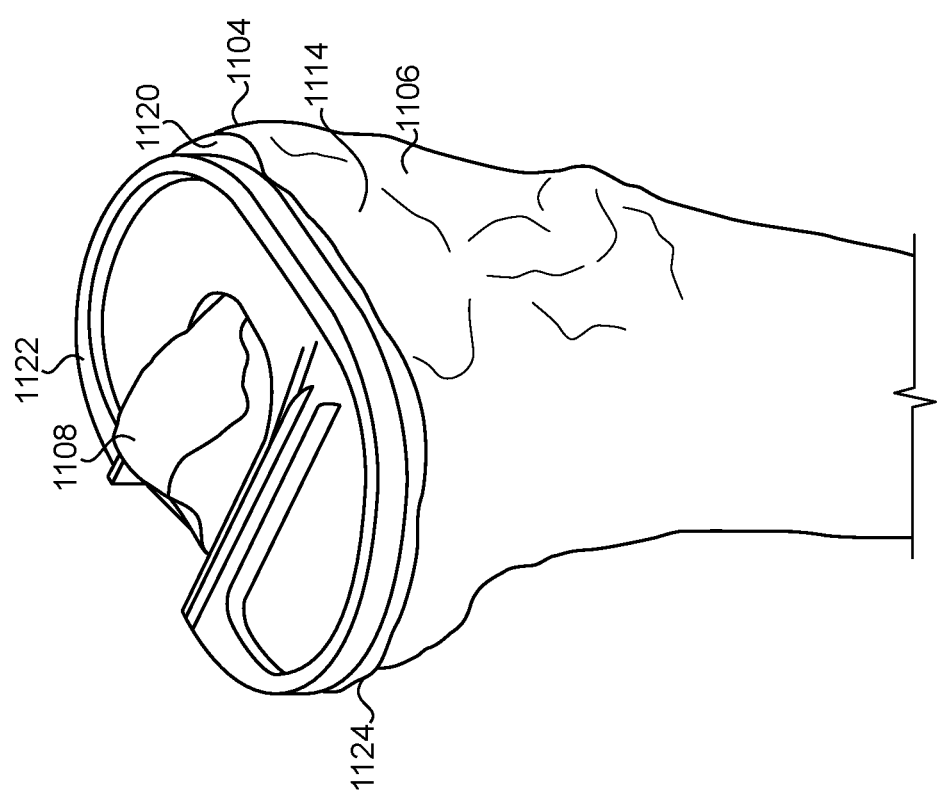
FIG. 43 illustrates a medial side perspective view of an exemplary bi-cruciate retaining tibial tray positioned on a resected bone surface at a proximal end of a tibia.

Such potential differences in the resulting size and/or shape of the tibia 1106 after the tibia 1106 is cut or resected can, in at least certain circumstances, not be realized or otherwise known until after such cutting of the tibia 1106 has commenced or concluded. Additionally, such discovery of an unanticipated size and/or shape of the resulting cut or resected bone surface also can, in at least some instances, coincide with the unanticipated variation in the actual location of the tibial eminence 1108. For example, FIG. 43 illustrates a medial side perspective view of an exemplary bi-cruciate retaining tibial tray 1122 positioned on a resected bone surface 1120 at a proximal end 1104 of the tibia 1106. As shown in the depicted example, the anticipated size and/or shape of the resected bone surface 1120, such as, for example, the size and/or shape of the resected bone surface 1120 around the proximal tibia periphery 1124, can be different from the actual shape and/or size that remains after bony resection. However, again, those differences may remain unknown until after the bony resection has commenced or concluded. Thus, in the example depicted in FIG. 43, an unexpected difference in the size and/or shape of the resected bone surface 1120 can result in compromised tray coverage. For example, such an unexpected variance in the size and/or shape of the tibia 1106 at the resected bone surface 1120 can result in the under-hanging of the bi-cruciate retaining tibial tray 1122 at least about a portion of the proximal tibia periphery 1124, which can result in the absence of contact between the tibial tray 1122 and the cortical rim along at least a portion of the cortical rim.

Figure 44:
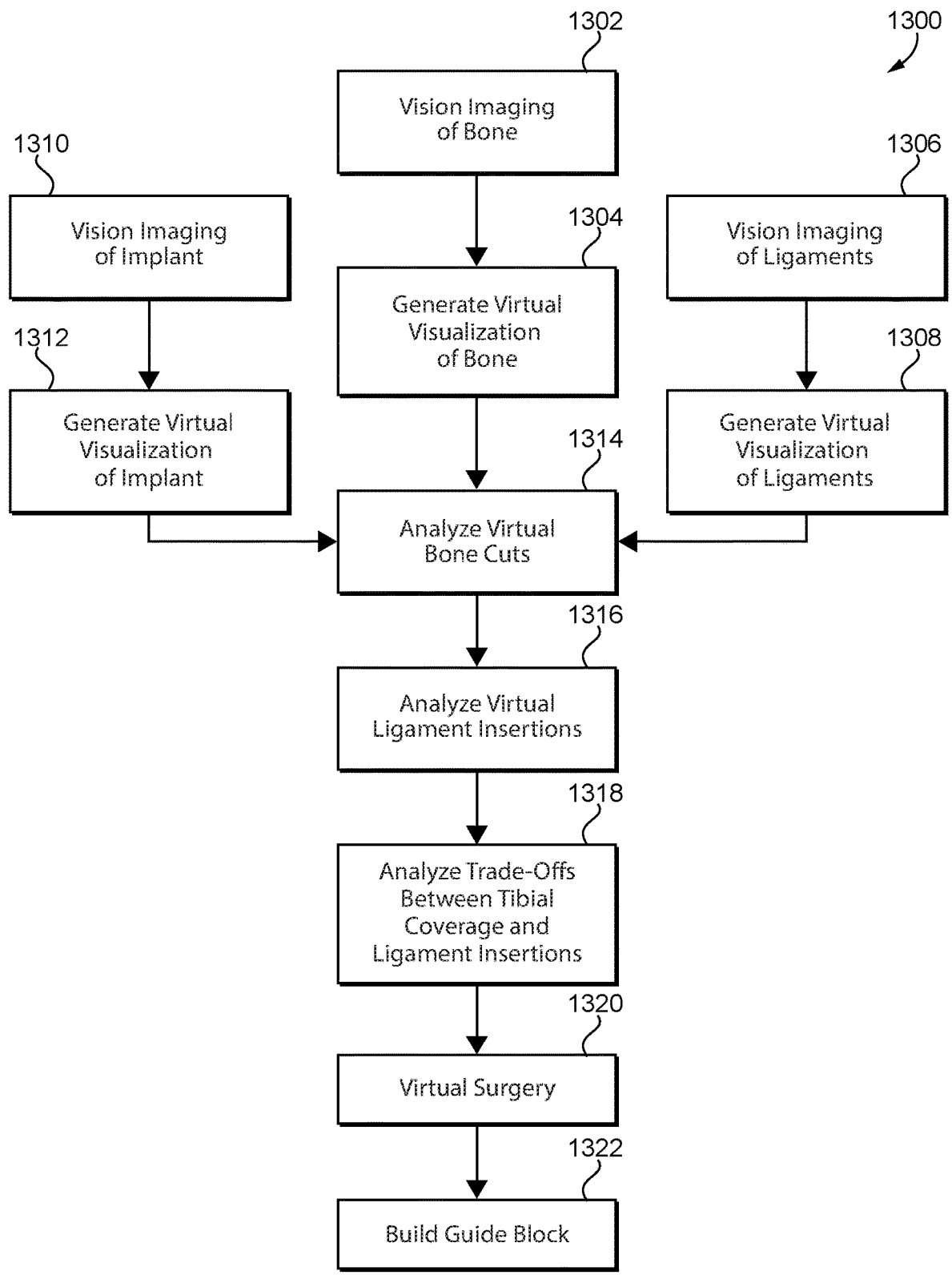
FIG. 44 illustrates a schematic flow diagram of an exemplary process for preoperative planning that includes virtual visualization and analysis for bone preparation and orthopedic implant design and positioning.

FIG. 44 illustrates a schematic flow diagram of an exemplary process 1300 for preoperative planning that includes virtual visualization and analysis for bone preparation and orthopedic implant design and positioning. As noted above, the blocks illustrated for the processes in the present application are understood to be examples only, and blocks can be combined or divided, and added or removed, as well as re-ordered in whole or in part, unless explicitly stated to the contrary. Further, while the below exemplary process is discussed with respect to preparation of a tibia and associated ligaments, the below discussed process is also applicable to a variety of other bones, ligaments, and/or implant procedures, including, but not limited to implant procedures, and any associated bone resection, involving hips, shoulders, and ankles, among other joints and associated bones. Further, the bone referred to herein may be a bone of a human or of an animal.

At block 1302, one or more images of at least the bone(s) that is/are to be resected are obtained. Such images can be obtained using a variety of different imaging sources or technology, including, for example, magnetic resonance imaging (MM), X-ray(s), computerized tomography (CT) scans, ultrasounds, two and/or three-dimensional cameras, among other imaging sources, systems, or technology that can take images or otherwise provide information regarding the size and/or shape of the bone. For example, one or more images obtained at block 1302 can, according to certain embodiments, be of at least the proximal end 1104 of the tibia 1106 of a particular patient who will be undergoing a knee implant procedure. Additionally, while block 1302 is discussed with reference to obtaining images, the information obtained at block 1302 may also, or alternatively, include information from anthropometrics of the patient prior to surgery using, for example, motion capture, force plate data, stair climb data, stair descend data, and/or chair rise data, among other types of data. Further, the imaging can also include obtaining at least certain measurements of the bone and/or patient, including, for example, anatomic measurements and/or biomechanic measurements.

At block 1304, the images obtained at block 1302 can be used to generate a two-dimensional and/or three-dimensional computer model(s) of the bone(s), such as, for example, a two-dimensional and/or three-dimensional image of at least the proximal end 1104 of the tibia 1106. The virtual model of the bone, along with other models discussed herein, can be computer generated in a variety of manners, as discussed, for example, in U.S. patent application Ser. No. 14/232,958, filed on Mar. 21, 2014, the contents of which are incorporated herein in their entirety. For example, according to certain embodiments, using appropriate software, two and/or three-dimensional more images taken at block 1302, as well as possible associated extrapolation, can be used to generate a three-dimensional model of the bone(s). Alternatively, or optionally, the one or more images, as well as an associated template or model based on the particular type of bone that was the subject of the imaging at block 1302, can be used to generate two-dimensional and/or three-dimensional virtual model(s) of the bone(s).

Alternatively, according to certain embodiments, a model of the patient's bone may not necessarily be generated. Instead, for example, measurements from the patient, and/or an application, such as, for example, a web based application can be used that can allow the user to be provided with virtual implant preparation information visualization. Further, such implant visualizing can be achieved in a variety of different manners, including, for example, via use of a medical image viewer, which may provide visualization of at least both patient imaging and implant geometry, which can provide information that can be used to design instrument(s) for the patient for use during the implantation procedure.

Optionally, similar to block 1302, the process 1300 can also include, at block 1306, obtaining one or more images of at least some of the ligaments that may be directly affected by, or otherwise involved in, the planned surgical procedure. For example, with respect to a preparatory procedure involving the tibia 1106 for an knee implant procedure, one or more images can be attained at block 1306 using a variety of different imaging sources or technology that provide at least visual information pertaining to characteristics of at least some ligaments at or around the bone, are moreover, in this example, the tibia 1106. Such images can provide a variety of information, including, for example, information that detects, or which may be used to determine, the location at which the ligament(s) attach to the bone. For example, with respect to the tibia 1106, such information may indicate and/or provide information that can be used to determine or approximate insertion locations of the anterior cruciate ligament (ACL) and/or the posterior cruciate ligament (PCL) relative to the tibial eminence 1108. While attaining such information may be useful with certain knee implant procedures, such as, for example, uni-compartmental knee replacement (UKA) and bi-cruciate knee replacement (XR), for at least other types of knee implant procedures in which the ACL and PCL (if present) may be removed, such as, for example, total knee replacement (TKA), such information may be unnecessary.

At block 1308, the images obtained at block 1306 can be used to generate a two-dimensional and/or three-dimensional model or representation of the ligaments. Similar to block 1304, the model generated at block 1308 can, using the appropriate software, be generated using at least some two-dimensional and/or three-dimensional images and/or information, as well as via possible associated extrapolation and/or models or templates associated with those ligaments and/or the corresponding joint. Further, while blocks 1302, 1304, are discussed separately from the blocks 1306, 1308 associated with the imaging and virtual model generation for the ligament(s), according to certain embodiments, the images obtained at either block 1302 or 1306 can be used in connection with generating a two and/or three-dimensional virtual model(s). For example, blocks 1302 and 1304 can be used at either block 1304 or 1308 that includes both the bone(s) and the associated ligament(s). Alternatively, to the extent that separate virtual models of the bone(s) and ligament(s) are each generated at blocks 1304, 1308, according to certain embodiments, those separate models may be combined or incorporated so that a single model is provided that depicts both the bone(s) and the ligament(s).

Optionally, according to certain embodiments, the process 1300 can include, at block 1310, obtaining two-dimensional and/or three-dimensional images of the implant system and/or associated component or preparatory tool that will be implanted or otherwise used in preparing the bone and/or joint for the implantation. According to such an embodiment, the process 1300 can also include at block 1312, and similar to blocks 1304 and 1308, use of at least some of the images obtained at block 1310 to generate, using appropriate software, a two-dimensional and/or three-dimensional virtual model of the implant system and/or associated component or preparatory tool. Alternatively, rather than generating a three-dimensional model via such images, the two-dimensional and/or three dimensional model may be provided via a computer-added design or other computer design or image file(s) that corresponds to the particular implant system and/or associated component or preparatory tool. For example, such models can be files that are provided by the manufacturer of the implant system and/or of the associated component or preparatory tool and which are imported and/or uploaded to the computer system being used for the evaluation of the system. Further, the implant system and/or associated implant components can also be imported without specifying component sizes so that, during process 1300, optimum components sizes can be determined or selected by the based on the below-discussed analyses and/or associated information or data.

At block 1314, the models generated at blocks 1304, 1308, 1312, or otherwise provided, can be analyzed. According to certain embodiments, such analysis can include displaying, on a display or monitor, the corresponding size and/or shape of the bone at particular potential bone cut locations. Such analysis may provide at least a virtual representation, on the display, and before actual cutting of the bone, of the resulting size and shape of the resected bone surface following the bone cut at that particular location(s), including depth, of the bone. Moreover, such an analysis can include attaining visual representations of the resulting size and/or shape of the resected bone surface at a plurality of different cut locations. Thus, based on such virtual information, including a comparison of the differences in the resulting size and/or shape of the resected bone at different bone cut locations, a preoperative decision can be made as to a particular location, or depth, at which the cut in the bone is to be made. Such preference, could, for example, be based on the extent to which the resulting size and/or shape of the resulting resected bone surface conforms to the size and/or shape of the implant system and/or component that may be positioned at that location. For example, with respect to the tibia 1106, such analysis can include the extent to which there will be cortical rim contact and/or bone coverage by a tibial plate that may be secured to, or positioned adjacent to, the resected bone surface. Such analysis can also include investigating potential resulting weaknesses in the cut bone and surrounding portions of the bone, including, for example, potential resulting weakening of the tibial eminence 1108, that could be created or enhanced by resecting the bone at a particular location and/or depth.

Other factors or considerations, in addition to the size and/or shape of the resected bone surface formed by cutting into the bone at a particular bone cut location can also be considered when determining the location for bony resection. For example, at block 1316 according to certain embodiments and/or surgical procedures, the impact that bony resection may have on any associated ligament(s) may also be virtually analyzed, such as, for example, by a virtual representation on the screen that may, or may not, be the same as the displayed virtual representation of the bone. Such analysis can include detecting the insertion location of ligaments into the bone, such as, for example, the ACL and/or PCL into the tibia 1106.

According to certain embodiments, the process 1300 can also include, at block 1318, evaluating the trade-offs or compromises that may made to one or more considerations for bony resections at different locations along the bone. For example, with respect to at least the discussed tibia 1106 example, there may not necessarily be a fixed relationship between obtaining tibial tray 1122 coverage of the resected bone surface and maintaining the integrity of the corresponding or adjacent ligament(s). Thus, while cutting the bone at a certain depth may be beneficial in terms of the resulting size and/or shape of the bone providing a surface for optimal tibial tray coverage, cutting to such a depth can adversely impact the connection, or strength thereof, between the tibia 1106 and the ACL and/or PCL. Conversely, resecting a bone at a location that may be optimal in terms of the connection of the ACL and/or PCL to the tibia 1106 may be less then optimal for tibial tray 1122 coverage. Further considerations may be given more weight and importance, including, for example, based on the relative importance to the safety and/or needs of the patient and/or the functionality of the implant system, among other bases.

Thus, at block 1318, preoperative decisions, and/or options, as to the location at which bony resection may occur, and the associated tradeoffs or compromises with respect to certain considerations, including tibial coverage and ligament insertion locations, among other considerations, can be evaluated. According to certain embodiments, such trade-offs or compromises can be evaluated in connection with generating virtual visualization information pertaining to bone cuts for a plurality of bone cut locations and/or virtual visualization of information pertaining to the associated ligaments, among other information. As previously discussed, such visualization information can include, for bone cuts at a plurality of locations along the bone, one or more virtual versions, images, and/or representations of the resulting resected bone surface for each particular bone cut location. According to certain embodiments, such virtual information can also include relevant measurements or sizes, as well as representations of other features of the patient's anatomy or the associated implant system or component. Further, according to certain embodiments, such information can be provided for approval or modification such as, for example, approval and/or modification by one or more members of a surgical team. However, again, such evaluation can be preoperative, and thus may assist in reducing the above-discussed surprises that can traditionally occur when the size and/or shape of the bone is realized during and/or after the resection of the bone.

At block 1320, one or more virtual procedures or operations using one or more of the above-discussed virtual bone cut locations can be performed. For example, a surgeon or engineer may first virtually size and virtually implant the above-discussed modeled implant onto the above-discussed modeled bone, which, in the illustrated example, is a virtual knee implant component on a virtual representation of the patient's tibia. Such virtual implantation can include attempting to obtain the best bone fit and mechanical axis alignment as is typically conventionally done, but without the pressure and associated risks of an actual surgery. This initial virtual sizing and virtual placement can be based on a variety of surgical techniques, including, for example, techniques used to determine internal-external (IE) rotation of the tibia.

According to certain embodiments, such virtual procedures or operations can be performed in connection with analyzing the trade-offs or compromises discussed above with respect to block 1318. Alternatively, according to other embodiments, the virtual surgery can be performed after the selection of one or more bone cut locations from block 1318. The virtual surgery provides a further opportunity to evaluate the selected location for bony resection, as well as any associated trade-offs or compromises. Such evaluation can, in at least certain circumstances, result in modifications, adjustments, and/or an identification of discrepancies in at least the planned bone cut location, among other potential modifications. For example, the virtual surgery at block 1320 can provide information indicating the stresses in associated bone, ligaments, muscle, and or tissue. The virtual surgery can also include, at block 1320, evaluating and/or modifying the sizing and/or configuration of components of the implant system and/or associated preparatory tools based on the size and/or shape of the bone at the selected bone cut.

According to certain embodiments, the virtual surgery can also include evaluating, or determining, the positioning of one or more pin holes in the bone. With respect to the tibia 1106, such pin holes can include distal holes that are used to line-up a datum block of a guide, which, as discussed below, can provide a platform that can establish a plane parallel to the bone cut of the tibia 1106 that will be made via use of a cutting slot of a cutting block or guide. Additionally, or optionally, the pin holes can also include an eminence pin hole, which can be used to set the medial-lateral (ML) position and internal-external (IE) rotation, of a tibial eminence for a vertical eminence cut. The virtual surgery can also, according to certain embodiments, include marking, in the virtual visualization of the bone and associated surgery, the location of the anterior eminence cut.

Thus, based on information obtained during the virtual surgery, consideration may be given as to whether to modify the preoperative plan. For example, such modifications could include modifying the bone cut location, the orientation of the bone cut, the orientation and/or size of any components of the implant system, and/or a ligament release location, among other possible modifications. Accordingly, the virtual surgery, among other steps in the process 1300 can be an iterative process in which the impact of certain adjustments, modifications and/or options can be evaluated in connection with determining the operative plan, and including the associated implant components, that will eventually be selected for use during surgery.

According to certain embodiments, upon completion of the virtual surgery or surgeries and the compiling of the associated data, one or more suggested locations of the bone cut and/or suggested sizes or features of the associated implant component can be presented for one or more members of the surgical team. For example, the data obtained from the virtual surgery can provide sizes and/or relative spatial orientations the bone and/or implant component(s), along with one or more expected performance characteristics, such as, for example, ligament tension, range of motion, efficiency, stress environment(s), fixation strength, ligament balance, anatomic fit (e.g., bone fit), fixation force(s), and/or implant longevity, associated with said suggested sizes and relative spatial orientations. The surgeon may then decide to re-orient the components of the prosthesis and/or the bone cut location based on expected performance characteristics calculated by the software in order to optimize anatomic fit and biomechanic performance.

Additionally, various portions or steps of the process 1300 discussed herein, including, but not limited to, the virtual surgery at block 1320, can utilize a medical image viewer. Further, for example, the various models discussed herein can be viewed in such a medical image viewer and used for a variety of purposes, including, but not limited to, reporting the proper pose of implant cuts as well as generating information that can be used in instrument guide design.

At block 1322, a cutting block or guide can be created that has features that generally correspond to, at least in part, the guide that was approved and/or modified from at least the virtual surgery. According to certain embodiments, such a guide can also be built with pin holes, including the above-discussed pin holes for the datum block and eminence pin hole, that correspond with the features of the guide block that were deemed suitable, or otherwise modified based on, at least the virtual surgery from block 1320. Alternatively, according to certain embodiments, the location and/or orientation of the pin holes for the datum block and eminence pin hole, as well as other pin holes, can be, at least in part, based on other features of the guide, such as, for example, the location and/or orientation of the cutting slot. According to certain embodiments, such a cutting slot and pin holes in the guide can be oriented to the same articular surfaces that guide the block on the bone during surgery.

Additionally, the virtual surgery, and associated determination of features of the corresponding custom-built cutting guide, can allow for the building of a single cutting guide that can handle a variety of different types of procedures. For example, according to the illustrated embodiment and use with knee implant procedures, a single guide can be built at block 1322 that can accommodate use for total knee replacement (TKA), uni-compartmental knee replacement (UKA), and bi-cruciate knee replacement (XR) procedures. Thus, for example, if during surgery the bone is discovered to have certain damage, such as, for example, arthritis, osteoporosis, and/or the bone is too hard, among other potential issues relating to the bone, the type of implant surgery, such as, for example, uni-compartmental knee replacement or bi-cruciate knee replacement that was to be performed, may be changed, such as, for example, changed to a total knee replacement procedure. Similarly, the type of implant procedure may also be changed, such as, for example, changed to a total knee replacement, if during the operation one or more ligaments is/are discovered to have certain damage or injury. According to the illustrated embodiment, the guide built at block 1322 can accommodate such intraoperative adjustments, as, as discussed above, in the illustrated example, as a single guide can be built to accommodate such different types of surgical and/or implant procedures.

Figure 45:
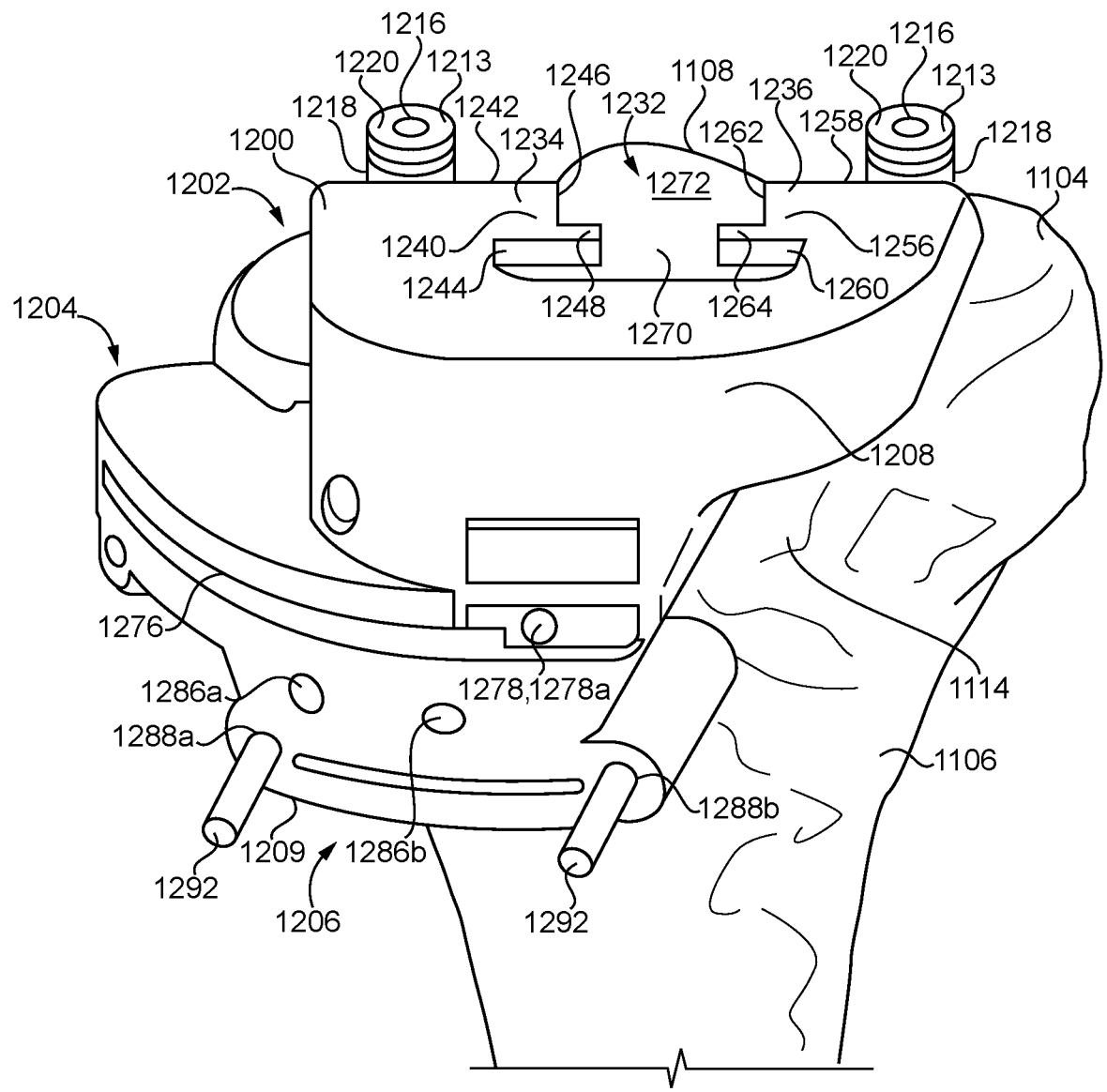
FIG. 45 illustrates an anterior side perspective view of an exemplary adaptive guide operably secured via pins to a proximal end of a tibia.
Figure 46:
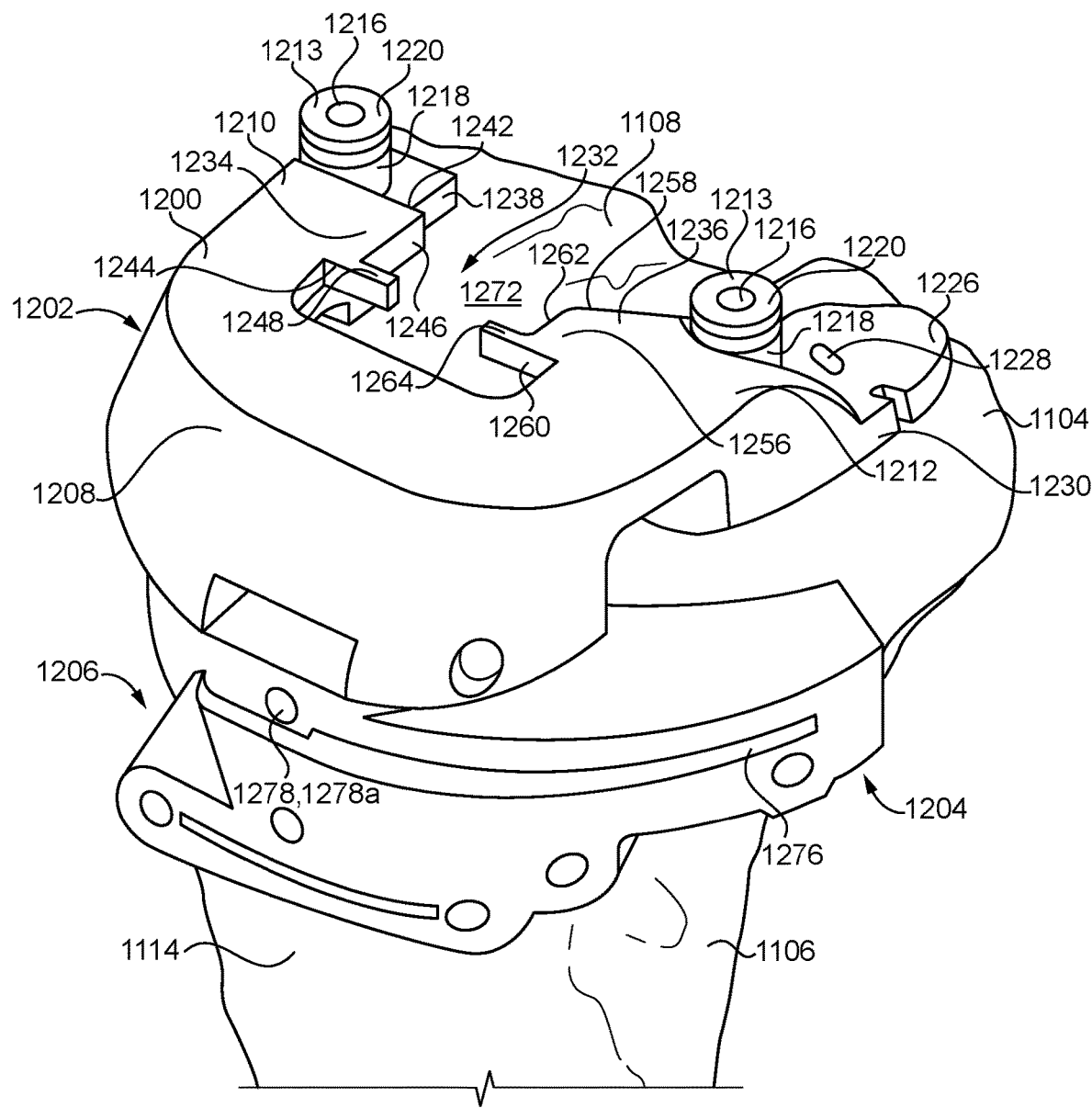
FIG. 46 is a lateral side perspective view of the exemplary adaptive guide and the proximal end of the tibia shown in FIG. 45.
Figure 47:
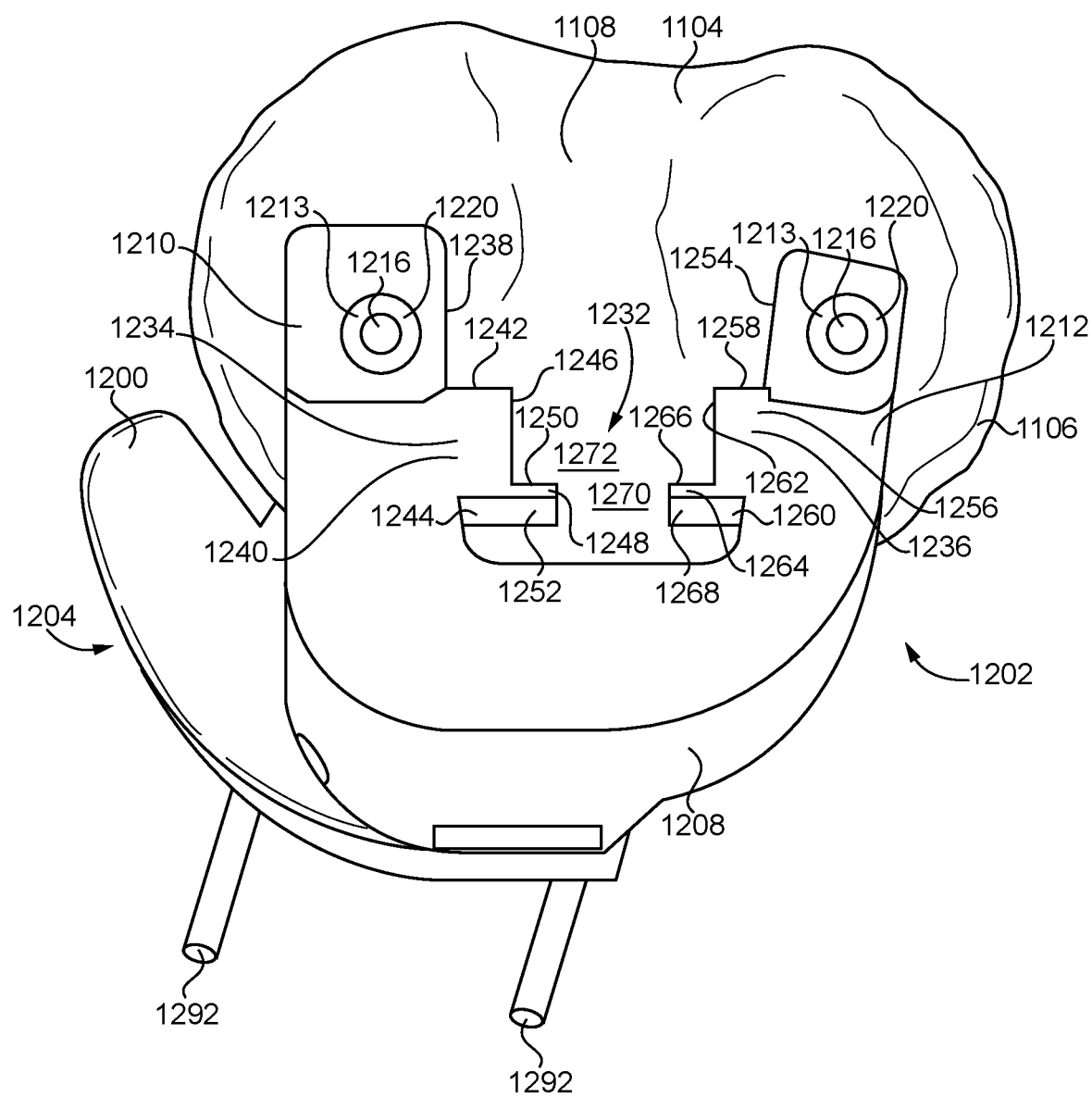
FIG. 47 is a superior view of the exemplary adaptive guide and the proximal end of the tibia shown in FIG. 45.
Figure 48B:
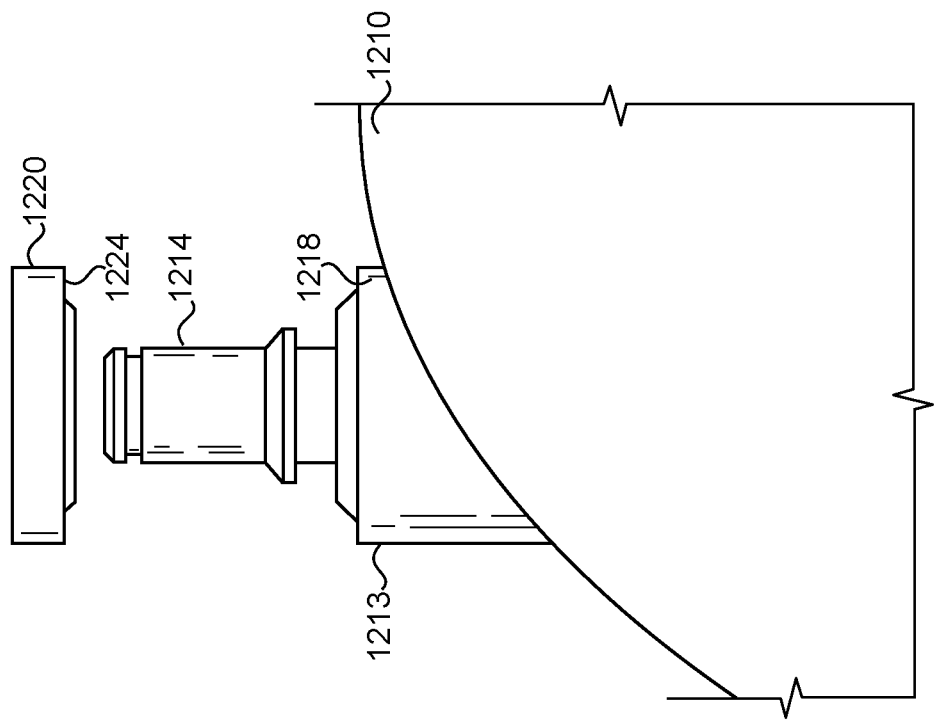
FIGS. 48A and 48B illustrate side views of a pin positioned in a guide boss that has a removable capture portion.
Figure 48A:
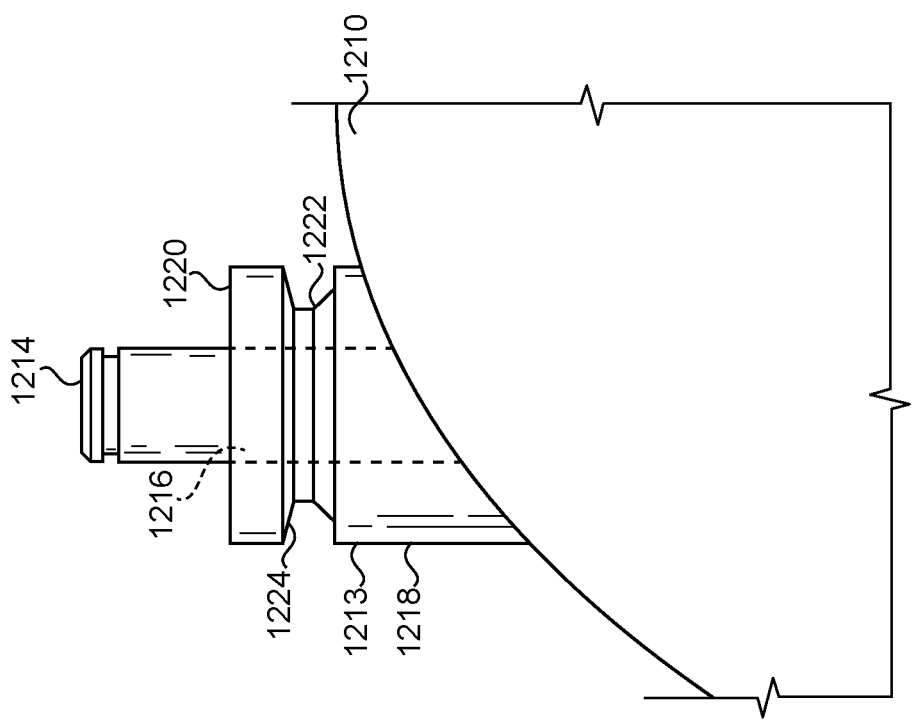

FIGS. 45-47 illustrate an exemplary adaptive guide 1200 that can be built at block 1322.

As illustrated, the adaptive guide 1200 can include a paddle section 1202, a cutting and alignment section 1204, and an anterior pinning section 1206. Similar to the exemplary tibial cutting block 1100 depicted in FIG. 42, the paddle section 1202 can include an anterior tibial portion 1208, a medial tibial paddle 1210, and a lateral tibial paddle 1212. The anterior tibial portion 1208 can be configured to overly a portion of the of the anterior face 1114 of the tibia 1106, while the medial and lateral tibial paddles 1210, 1212 can be configured to overly at least portions of the medial and lateral plateaus, respectively, of the tibia 1106. Further, although not illustrated, the anterior tibial portion 1208, medial tibial paddle 1210, and lateral tibial paddle 1212 of the adaptive guide 1200 can include bone-interfacing surfaces that are configured to interact with opposing portions of the proximal end 1104 of the tibia 1106 and/or associated cartilage at or around the tibia 1106.

According to the illustrated embodiment, the medial and lateral tibial paddles 1210, 1212 of the adaptive guide 1200 can each include one of the one or more paddle pin holes. The paddle pin holes can be positioned such that, when the adaptive guide 1200 is operably positioned on the proximal end 1104 of the tibia 1106, pins that extend through the paddle pin holes in medial and lateral tibial paddles 1210, 1212 can enter into the proximal end 1104 of the tibia 1106.

Guide bosses 1213 can extend around one or more of the paddle pin holes that can assist in directing the pins 1214 (FIGS. 48A and 48B) into/through the paddle pin holes and into the adjacent proximal end 1104 of the tibia 1106. The guide bosses 1213 can have an outwardly extending size that can guide the displacement of pins through at least the corresponding paddle pin holes, and thus through the adaptive guide 1200, as the pins are impacted, drilled, or otherwise inserted into an adjacent portion of the tibia 1106. Each guide boss 1213 includes a guide orifice 1216 that is in fluid communication with the paddle pin holes, and which is sized to accommodate passage of a pin through the guide boss 1213. The guide bosses 1213 can be configured to direct the pins away from the edges of the tibia 1106 and/or generally limit the angular directions at which the pin can extend through the associated adaptive guide 1200. Additionally, the relative placement of the guide bosses 1213, as well as the relative location of the associated adaptive guide 1200, can allow for pins to be placed into the tibia 1106 at locations that can accommodate further, or other, distal cuts of the tibia 1106, including, but not limited to, one or more recuts of the tibia 1106, that can be used to prepare the bone interfacing surface(s) of the tibia 1106 for implantation of a corresponding portion of the knee implant system.

According to certain embodiments, one or more of the guide bosses 1213 includes a boss body 1218 and a removable capture portion 1220 that generally define at least a portion of the guide orifice 1216. As shown by at least FIG. 48A, the capture portion 1220 is coupled to the boss body 1218 by a neck portion 1222 that is sized to provide an undercut between the boss body 1218 and the capture portion 1220. Moreover, the neck portion 1222 provides a recess or undercut around at least a portion of the guide boss 1213. Thus, a cross-sectional wall thickness between an inner wall of the guide boss at the guide orifice 1216 and an outer wall of the guide boss 1213 at the neck portion 1222 can be thinner than a corresponding cross-sectional wall thickness between the inner wall at the guide orifice 1216 and the outer wall of the guide boss 1213 at the boss body 1218 and/or the capture portion 1220. Further, a recess or undercut provided by the neck portion 1222 can be sized to receive a tool, such as, for example a rongeur, that can be positioned in the recess or undercut provided by the neck portion 1222 and beneath the capture portion 1220. According to such an embodiment, as indicated by at least FIG. 48B, a pulling and/or twisting force can be provided, via the tool, against the neck portion 1222 and/or the capture portion 1220, such as, for example, a bottom wall 1224 of the capture portion 1220, that can break the guide boss 1213, such as at the neck portion 1222, in a manner that allows the capture portion 1220 to be detached from the boss body 1218. Thus, in the event a pin 1214 received in the guide orifice 1216 of the guide boss 1213 is over driven into the guide boss 1213, the capture portion 1220 can be selectively removed so as to expose a portion of the over-driven pin 1214 that can be subsequently coupled to a driver and backed out of the guide boss 1213 and/or out of the associated bone.

Referencing FIG. 46, according to certain embodiments, one or both of the medial and lateral tibial paddles 1210, 1212 of the adaptive guide 1200 can also include a selectively removable paddle extension 1226. As shown, the paddle extension 1226 can be sized to extend a length at which the associated medial tibial paddle 1210 and/or lateral tibial paddle 1212 extends across the proximal end 1104 of the tibia 1106 at least in the direction of the posterior side of the tibia 1106. According to the illustrated embodiment, the paddle extension 1226 can be, at certain locations, separated from the adjacent portion of the medial or lateral tibial paddle 1210, 1212 by one or more perforations 1228. For example, in the illustrated example, a first perforation 1228 can extend through a portion of a sidewall 1230 of the lateral tibial paddle 1212, while a second perforation 1228 can extend through a portion of a generally central area between the paddle extension 1226 and the remainder of the lateral tibial paddle 1212. The perforations 1228 can provide weakened areas and/or a bending location in the medial and/or lateral tibial paddle 1210, 1212 that can facilitate the selective detachment of the paddle extension 1226 from the associated medial and/or lateral tibial paddle 1210, 1212.

Referencing FIGS. 45-47, the paddle section 1202 can also include an eminence indicator 1232 that can be generally positioned in, or otherwise extend into, an area between the medial and lateral tibial paddles 1210, 1212 of the adaptive guide 1200. The eminence indicator 1232 can be configured to provide a visual indicator as to a location of at least a portion of bone that is to remain generally intact during, and after, bony resection. For example, according to the illustrated embodiment, the eminence indicator 1232 can be positioned to at least indicate a width and an end location of at least a portion of the tibial eminence 1108 that, at least according to the decisions made in preoperative planning, is not to be removed during bony resection. Further, according to the illustrated embodiment, at least a portion of the eminence indicator 1232 can provide a guide for a marking instrument to transfer the information or locations provided by the eminence indicator 1232 to the bone. For example, a marking instrument, such as, for example, a surgical pen, among other marking instruments, can use at least a portion of the eminence indicator 1232 as a guide as the marking instrument transfers information, such as particular locations, provided by the eminence indicator 1232 to the generally adjacent bone surface of the patient's bone.

According to the illustrated embodiment, the eminence indicator 1232 comprises opposing first and second segments 1234, 1236. According to certain embodiments, the first segment 1234 can comprise a portion of the medial tibial paddle 1210, such as, for example, at least a portion of an inner sidewall 1238 of the medial tibial paddle 1210. Alternatively, according to other embodiments, the first segment 1234 can include a first body portion 1240 that inwardly extends from at least a portion of medial tibial paddle 1210, such as the inner sidewall 1238 of the medial tibial paddle 1210, and generally extends at least in the direction of the opposing lateral tibial paddle 1212. According to the illustrated embodiment, the first body portion 1240 of the first segment 1234 can be generally defined by opposing posterior and anterior walls 1242, 1244, as well as a medial wall 1246 that is generally positioned opposite of the medial tibial paddle 1210.

Additionally, according to the illustrated embodiment, the first segment 1234 can also include a first arm 1248 that inwardly extends from the medial wall 1246, and generally extends in at least the direction of the second segment 1236. The first arm 1248 can include opposing first and second walls 1248, 1250. As shown by at least FIG. 47, according to at least certain embodiments, the first wall 1250 of the first arm 1248 can be generally parallel to the second wall 1252. Additionally, according to the illustrated embodiment, the second wall 1252 can extend from the anterior wall 1244 of the first body portion 1240 of the first segment 1234. Further, as shown in at least FIG. 47, although the first wall 1250 can be oriented in a variety of manners with respect to the medial wall 1246 of the first body portion 1240 of the first segment 1234, according to the illustrated embodiment, the first wall 1250 can be generally perpendicular to the medial wall 1246.

With respect to the second segment 1236, according to certain embodiments, the second segment 1236 can comprise a portion of the lateral tibial paddle 1212, such as, for example, at least a portion of an inner sidewall 1254 of the lateral tibial paddle 1212. Alternatively, according to other embodiments, the second segment 1236 can include a second body portion 1256 that inwardly extends from at least a portion of the lateral tibial paddle 1212 and generally in the direction of the medial tibial paddle 1210. According to the illustrated embodiment, the second body portion 1256 of the second segment 1236 can be generally defined by opposing posterior and anterior walls 1258, 1260 as well as a lateral wall 1262 that is generally positioned on an opposite side of the lateral tibial paddle 1212.

Additionally, according to the illustrated embodiment, the second segment 1236 can also include a second arm 1264 that inwardly extends from the lateral wall 1262 generally in the direction of the second segment 1236, and moreover, in the direction of the first arm 1248. The second arm 1264 can include opposing first and second walls 1266, 1268. As shown by at least FIG. 47, according to at least certain embodiments, the first wall 1266 of the second arm 1264 can be generally parallel to the second wall 1268. Additionally, according to the illustrated embodiment, the second wall 1268 can extend from the anterior wall 1260 of the second body portion 1256 of the second segment 1236. Further, as shown in at least FIG. 47, although the first wall 1266 can be oriented in a variety of manners with respect to the lateral wall 1262 of the second body portion 1256 of the second segment 1236, according to the illustrated embodiment, the first wall 1266 can be generally perpendicular to the lateral wall 1262.

Additionally, according to the illustrated embodiment, the medial wall 1246 of the first segment 1234 can be generally parallel to the lateral wall 1262 of the second segment 1236. Further, the first walls 1250, 1266 of the first and second arms 1248, 1264 can be generally parallel and aligned with each other such that, absent a gap 1270 therebetween, the first wall 1250 of the first arm 1248 could be a continuation of the first wall 1266 of the second arm 1264. Similarly, according to certain embodiments, the second walls 1252, 1268 of the first and second arms 1248, 1264 can be generally parallel and aligned with each other such that, absent the gap 1270 therebetween, second wall 1252 of the first arm 1248 could be a continuation of the second wall 1268 of the second arm 1264.

According to the illustrated embodiment, at least the medial and lateral walls 1246, 1262 of the first and second body portions 1240, 1256, and the first walls 1250, 1266 of the first and second arms 1248, 1264 can generally define an eminence gap 1272 that is sized to generally correspond to a size of at least a portion of the tibial eminence 1108 that is not to be removed during resection of the tibia 1106. For example, the medial and lateral walls 1246, 1262 of the first and second body portions 1240, 1256 can be separated by a distance that can generally correspond to a width of the tibial eminence 1108 that is to be retained. Further, the first walls 1250, 1266 of the first and second arms 1248, 1264 can generally define an ending location of the tibial eminence 1108. Thus, according to certain embodiments, the combination of the medial wall 1246 and the first wall 1250 of the first arm 1248 and the combination of the lateral wall 1262 and the first wall 1266 of the second arm 1264 can provide an indication of the anterior corners of the tibial eminence 1108. Further, according to certain embodiments, the particular sizing and orientation of the eminence indicator 1232, including, for example, the relative positions and/or orientations of at least the medial wall 1246, lateral wall 1262, first wall 1250 of the first arm 1248, and/or the first wall 1266 of the second arm 1264 can be determined using the images and/or models from the process 1300 discussed above, among other information.

Figure 49:
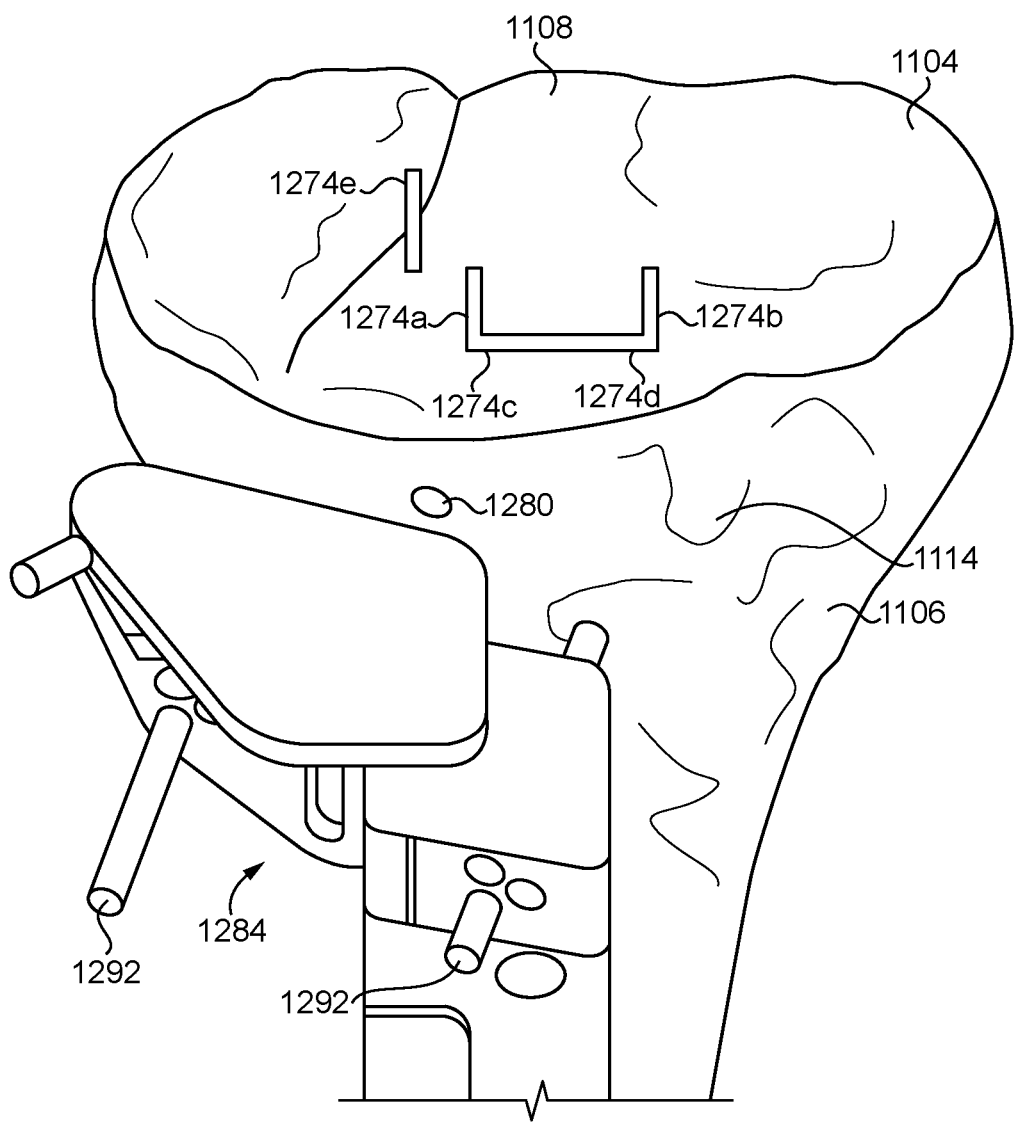
FIG. 49 illustrates an anterior side perspective view of a portion of an exemplary orientation stylus secured to a tibial bone that has been marked using the exemplary adaptive guide shown in FIGS. 45-47 to indicate medial-lateral (MP) and anterior-posterior (AP) portions, as well as internal-external (IE) rotation, of a tibial eminence that is to be preserved.

As previously discussed, in the illustrated embodiment, the location information provided by the eminence indicator 1232 can be transferred to the tibia 1106 to provide visual markers or borders that can correspond to the location of the anterior corners of an eminence cut. Moreover, such location and marking of the anterior corners of an eminence cut can provide an indication of which portions of the bone and/or tibial eminence 1108 are to be cut, and/or what portion(s) or region of the tibial eminence 1108 is/are not to be cut. For example, with the eminence indicator 1232 operably positioned via the operable coupling of the adaptive guide 1200 to the proximal end 1104 of the tibia 1106, such as, for example, the adaptive guide 1200 pinned to the tibia 1106 at a selected or predetermined orientation and/or position, the edges of at least a portion of the eminence indicator 1232 can be traced or otherwise provide a guide for a marking instrument, such as, for example, a surgical pen, among other types of marking instruments. Thus, for example, the medial wall 1246 and lateral wall 1262 of the first and second segments 1234, 1236 of the eminence indicator 1232 can be used as a guide for the marking instrument to place first and second markings 1274a, 1274b, respectively, (FIG. 49) on the tibia 1106 that can indicate a location, or width, of the tibial eminence 1108 that is to be retained. Similarly, the first walls 1250, 1266 of the first and second arms 1248, 1264 can be used as guides for placing third and fourth markings 1274c, 1274d (FIG. 49), respectively, that can indicate the ending location of the tibial eminence 1108. Further, as shown by FIG. 49, rather than being separate markings 1274c, 1274d, the marking location provided by the first walls 1250, 1266 of the first and second arms 1248, 1264 can form a continuous marking that extends between the first and second markings 1274a, 1274b, and thereby form at least the visual markings for the anterior corners of an eminence cut.

Additionally, according to certain embodiments, the medial tibial paddle 1210 can also be configured to provide an indication of a location of the internal-external (IE) rotation of the tibial eminence 1108 that is to be preserved. For example, according to the illustrated embodiment, at least a portion of the inner sidewall 1238 of the medial tibial paddle 1210 can be configured such that, when the adaptive guide 1200 is operably secured to the tibia 1106, the inner sidewall 1238 is positioned at a location that corresponds to at least a portion of the IE rotation of the tibial eminence 1108 that is to be preserved. Moreover, at least a portion of the inner sidewall 1238 of the medial tibial paddle 1210 can be configured to provide an edge that can, similar to the eminence indicator 1232, provide a location that can be traced, or otherwise guide, a marking instrument that can transfer the location of the inner sidewall 1238, and thus the indicated location of the IE rotation, to the proximal end 1104 of the tibia 1106. For example, FIG. 49 illustrates a marking 1274e that has been transferred to the proximal end 1104 of the tibia using the inner sidewall 1238 of the medial tibial paddle 1210 as a guide, and which can provide an indication of the IE rotation that is to be preserved.

As shown in at least FIGS. 45 and 46, the cutting and alignment section 1204 of the adaptive guide 1200 can include a cutting slot 1276 and one or more pin holes 1278. Similar to the cutting block 1116 discussed above with respect to the exemplary tibial cutting block 1100 depicted in FIG. 42, the cutting slot 1276 of the adaptive guide 1200 can be sized to receive insertion of a cutting blade that can cut or resect the tibia 1106. According to the illustrated embodiment, the cutting slot 1276 is oriented on the medial half of the anterior side of the adaptive guide 1200, and can be formed through the bone interfacing portions of the adaptive guide 1200, or may be recessed from the bone interfacing surfaces. The thickness of the cutting slot 1276 can help direct the orientation of the cutting tool, such as, for example, saw blade, as the cutting tool advances through the cutting slot 1276. Further, the translation of the cutting slot 1276 relative to the adaptive guide 1200, can, according to at least certain adaptive guides, assist in setting a resection depth.

Figure 50:
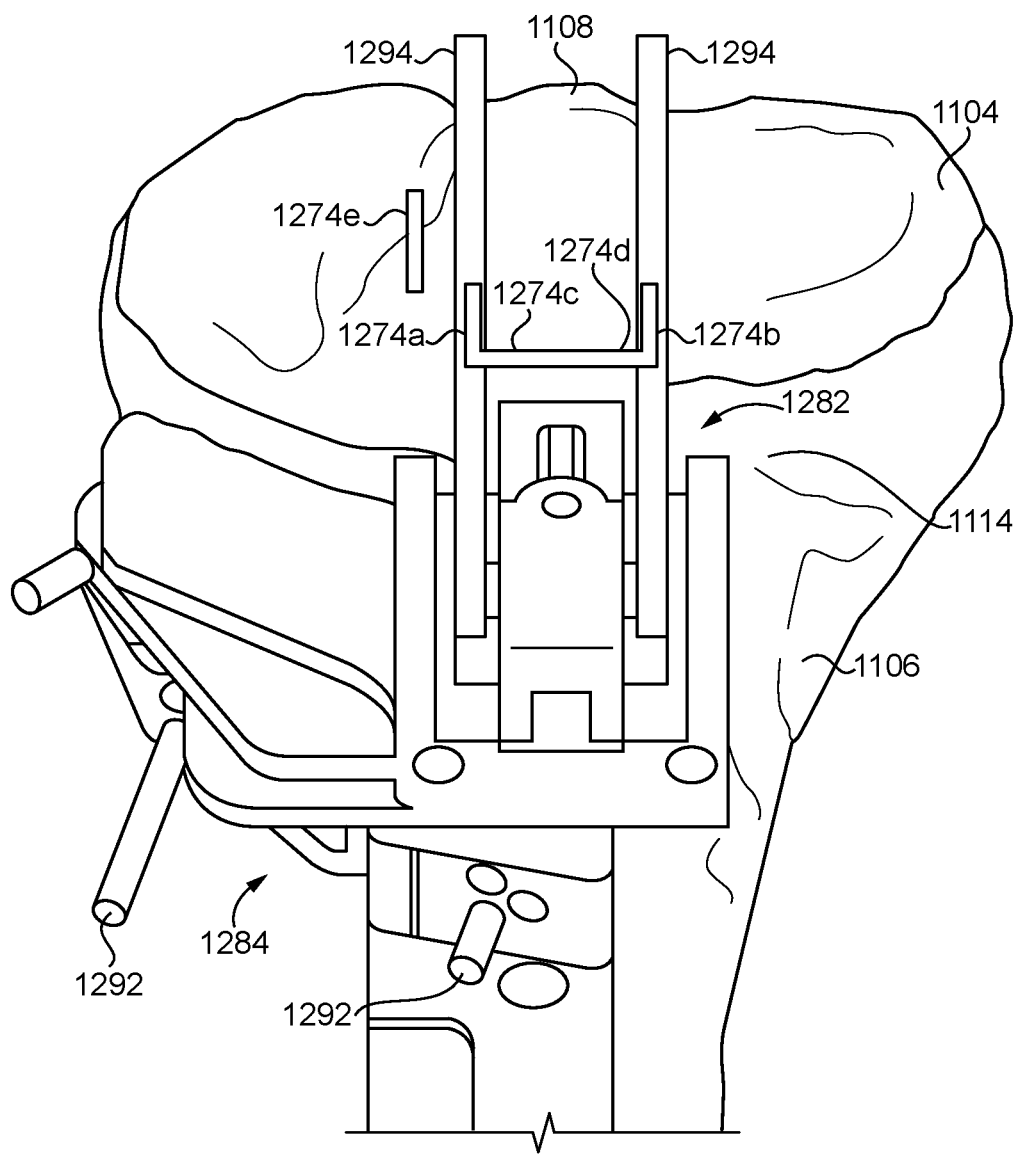
FIG. 50 illustrates a partial phantom, anterior side perspective view of a further portion of the exemplary orientation stylus shown in FIG. 48 attached to the tibia.

Similar to other pin holes in the adaptive guide 1200, the one or more pin holes 1278 of the cutting and alignment section 1204 can be configured to accommodate passage of at least a portion of a pin through each of the pin holes 1278 and into the tibia 1106. According to the illustrated embodiment, at least a plurality of the pin holes 1278 can be positioned about the cutting and alignment section 1204 of the adaptive guide 1200 so that a pin inserted therein can extend into the tibia 1106 at, or in the general vicinity of, an anterior face 1114 of the tibia 1106. Further, according to the illustrated embodiment, at least one pin hole 1278a, also referred to as an orientation stylus pin hole, of the cutting and alignment section 1204 can be positioned to receive a pin that extends into a hole 1280 (FIG. 49) in the tibia 1106 that can be used in connection with the later mounting of an armed portion 1282 of an orientation stylus 1284, as shown in FIG. 50, to the tibia 1106.

The anterior pinning section 1206 of the adaptive guide 1200 can include pin holes 1286a, 1286b that extend through the adaptive guide 1200 and into corresponding holes in, or around, at least the anterior face 1114 of the tibia 1106. According to the illustrated embodiment, the pin holes 1286a, 1286b of the anterior pinning section 1206 can include at least some pin holes 1286a, 1286b that can correspond to, or are otherwise be generally in alignment with, recut holes in the tibia 1106. Such recut holes could, if used, correspond to the relatively secure placement of a recut cutting block using pins that extent into those recut holes in the tibia, and could be used in the event a subsequent re-cut of the tibia is to be performed. Alternatively, or optionally, the pin holes 1286a, 1286b could be used at least in connection with pin holes in the tibia 1106, and/or the associated pins received therein, for other preparatory tools that can be secured to the tibia 1106.

The adaptive guide 1200 can also include a datum block 1290 that can provide a platform that can establish a plane that is parallel to a cut in the tibia 1106 that is formed via using of cutting slot 1276 of the adaptive guide 1200. As shown in at least FIGS. 45 and 46, the datum block 1290 can be positioned beneath the above-discussed pin holes 1286a, 1286b of the anterior pinning section 1206. Further, according to the illustrated embodiment, the datum block 1290 can generally provide a distal end or side of the adaptive guide 1200 along at least a portion of the anterior side of the adaptive guide 1200.

The datum block 1290 can also include one or more datum pin holes 1288a, 1288b that, similar to the pin holes 1286a, 1286b, are configured to accommodate passage of at least a portion of a pin 1292 through the datum pin holes 1288a, 1288b and into the tibia 1106. According to certain embodiments, the datum pin holes 1288a, 1288b can be configured to guide pins 1292 (FIG. 47) to a location(s), and/or provide pins at a relative orientation, that can correspond to the pin hole arrangement(s) of other preparatory tools. For example, according to the illustrated embodiment, the datum pin holes 1288a, 1288b comprises two datum pin holes 1288a, 1288b that are configured to receive pins 1292 that are generally parallel to each other, and which extend into the anterior face 1114 of the tibia 1106.

When the adaptive guide 1200 is removed from the tibia 1106, a portion of an orientation stylus 1284 (FIG. 49) having pin holes having a relative orientation similar to the anterior parallel pins 1292 can be secured to the tibia 1106 via at least the anterior parallel pins 1292, as shown in FIG. 49. As previously mentioned, the orientation stylus 1284 can include an armed portion 1282 that can, according to at least certain embodiments, be positioned relative to at least the tibia 1106 using a pin hole 1280 in the tibia 1106 that was generally aligned with the orientation stylus pin hole 1278a of the adaptive guide 1200. Further, such a process can also include aligning or centering arms 1294 of the armed portion 1282 of the orientation stylus 1284 with the above-discussed markings 1274a-d that were transferred to the tibia 1106 through use of the eminence indicator 1232, as well as orienting the arms 1294 to be generally parallel to the marking 1274e corresponding to the IE rotation of the tibia 1106, as discussed above.

FIG. 51 illustrates an anterior view of a general knee joint in which an exemplary femoral cutting block 2100 and an exemplary tibial cutting block 2102 are coupled to the associated femoral and tibial bones 2104, 2106, respectively. According to the depicted embodiment, the femoral and tibial cutting blocks 2100, 2102 are configured to engage portions of bone and cartilage on the femur 2104 and tibia 2106, respectively, in at least an attempt to align cutting surfaces within the cutting blocks 2100, 2102. More specifically, according to the depicted embodiment, the femoral cutting block 2100 is configured to facilitate a distal cut on the femur 2104, and the tibial cutting block 2102 is configured to facilitate a proximal cut on the tibia 2106, that can be made in connection with the installation of a knee replacement system.

Moreover, according to the illustrated embodiment, the femoral and tibial cutting blocks 2100, 2102 can be configured to provide guidance with respect to the resection of bone 2104, 2106 for an implant procedure(s) and without the use of either intramedullary or extramedullary guides.

While, for at least purposes of illustration, FIG. 51 illustrates a pair of exemplary femoral and tibial cutting blocks 2100, 2102, embodiments of the subject application are applicable to a variety of cutting blocks and/or cutting blocks used for a variety of different types of procedures and/or implantations, as well as other preparatory implant tools. For example, according to certain embodiments, the femoral and tibial cutting blocks 2100, 2102 can be configured for use in total knee replacement, uni-compartmental knee replacement, and/or bi-cruciate knee replacement. Additionally, as will be readily apparent herein, embodiments of the subject application are applicable to conventional slotted cutting blocks or guides, as well as patient-specific or customized cutting blocks. Further, the femoral and tibial cutting blocks 2100, 2102 can be constructed from a variety of different materials, including, for example, metal, plastic, and/or nylon cutting blocks, as well as cutting blocks constructed from a variety of other materials. Additionally, while embodiments discussed herein are illustrated with respect to knee implant systems and the associated cutting blocks, the subject application is also applicable to implant systems and tools, including, for example, implant systems relating to shoulders and hips, among other implant systems.

The exemplary femoral cutting block 2100 includes an anterior femoral portion 2108, a medial femoral paddle 2110, and a lateral femoral paddle 2112. According to the illustrated embodiment, these portions 2108, 2110, 2112 of the femoral cutting block 2100 can be configured to, when the femoral cutting block 2100 is operably positioned and/or secured to the distal end 2128 of the femur 2104, overlie portions of the anterior face, medial condyle and lateral condyle of the femur 2104, respectively.

As shown in the illustrated embodiment, at least the exterior surface of the femoral cutting block 2100 can include one or more pin holes 2114a-d, guide bosses 2115, a mechanical axis index 2116, and a cutting slot 2118. According to certain embodiments, the mechanical axis index 2116 can provide a visual reference point(s) at which the surgeon can, in connection with operably positioning and securing the femoral cutting block 2100 to the femur 2104, generally align the femoral cutting block 2100 with the mechanical axis of the femur 2104. According to at least certain procedures, imaging of the patient, including, for example, magnetic resonance imaging (MRI), X-ray(s), and/or computerized tomography (CT) scans, among other imaging techniques, of at least the femur 2104 can be used to assist with at least attempting to aligning the mechanical axis index 2116 of the femoral cutting block 2100 to the mechanical axis of the femur 2104.

The femoral cutting block 2100 can further include a cutting slot 2118 that is sized to receive insertion of a cutting blade that can cut or resect the femur 2104. Further, the cutting slot 2118 can be configured to at least assist in guiding the location, including depth, at which the blade that is inserted into the cutting slot 2118, and reciprocated or otherwise operated therein, is to cut into the femur 2104. Thus, the cutting slot 2118 can be oriented, via the orientation of the femoral cutting block 2100 relative to the femur 2104, to direct the distal cut on the femur 2104 for preparation of implantation of the associated implant device or system. When positioning and/or orienting the femoral cutting block 2100 onto and/or relative to the femur 2104, one or more imaging techniques and/or surgeon preference may be used to determine a location of the cutting slot 2118 of the femoral cutting block 2100 relative to the femur 2104, for example as described above.

As discussed below, one or more pin holes 2114a-d of the femoral cutting block 2100 can be configured and/or oriented to receive pins that extend through the pin holes 2114a-d and into an adjacent portion of the femur 2104. At least some of the pins can assist with generally operably securing, coupling, and/or pinning the femoral cutting block 2100 at a selected position and/or orientation to the femur 2104, while other pins, and/or the associated pin holes in the patient's bone can assist in at least aligning at least a portion of the implant system that will be implanted in the patient.

Guide bosses 2115 can extend around one or more of the pin holes 2114a-d that can assist in directing the pins into/through the pin holes 2114a-d and into the adjacent bone. The guide bosses 2115 can have an outwardly extending size that can guide the displacement of pins through at least the corresponding pin hole 2114a-d, and thus through the femoral cutting block 2100, as the pins are impacted, drilled, or otherwise inserted into an adjacent portion of the femur 2104. For example, the bosses 2115 can be configured to at least direct the pins away from the edges of the bone and/or generally limit the angular directions at which the pin can extend through the associated pin hole 2114a-d. Additionally, the relative placement of the bosses 2115, as well as the relative location of the associated pin holes 2114a-d, can allow for pins to be placed into the femur 2104 at locations that can accommodate further, or other, distal cuts of the femur 2104, including, but not limited to, one or more recuts of the femur 2104, that may be used to prepare the bone interfacing surface(s) of the femur 2104 for implantation of a corresponding portion of the knee implant system.

Figure 54:
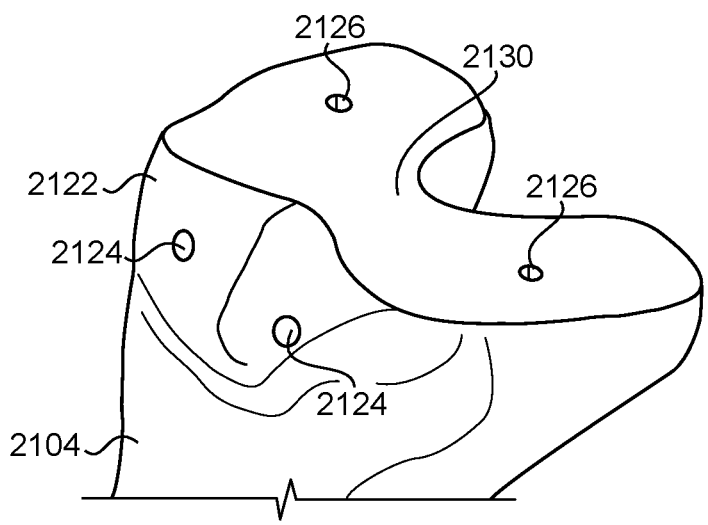
FIG. 54 illustrates a distal anterior perspective view of a portion of a resected femur having both distal pin holes and recut pin holes.

A first set of one or more of the pin holes 2114a, 2114b, referred to herein as recut holes 2114a, 2114b, can be oriented on an anterior face portion 2120 of the femoral cutting block 2100, including, for example, generally at or in relative proximity to the anterior femoral portion 2108. Thus, according to the illustrated embodiment, the recut holes 2114a, 2114b can each be oriented to receive passage of a pin that enters, and is inserted into, the anterior face 2122 of the femur 2104. FIG. 54 provides an example location in the femur 2104 at which pins that were driven through recut pin holes 2114a, 2114b of the exemplary femoral cutting block 2100 can form recut holes 2124 through the anterior face 2122, and into a portion, of the femur 2104. Additionally, according to certain embodiments, one or more of the recut holes 2114a, 2114b can have guide bosses 2115. Alternatively, or optionally, one or more recut holes 2114a, 2114b of the femoral cutting block 2100 can, similar to the auxiliary pin hole 2117 in FIG. 51, be generally flush with the adjacent surface of the anterior face 2122 of the femoral cutting block 2100.

According to the illustrated embodiment, the medial and lateral femoral paddles 2110, 2112 can include a second set of one or more pin holes 2114c, 2114d, referred to collectively as paddle holes 2114c, 2114d. As shown for example by at least FIGS. 52 and 53, according to the illustrated embodiment, the medial and lateral femoral paddles 2110, 2112 can each include one or more paddle holes 2114c, 2114d. Further, according to at least certain embodiments, as shown in at least FIG. 52, the paddle holes 2114c, 2114d can be located in relatively thin posterior portions of the medial and lateral femoral paddles 2110, 2112. According to the illustrated embodiment, the paddle holes 2114c, 2114d can be positioned such that, when the femoral cutting block 2100 is operably positioned on the femur 2104, pins that extend through the paddle holes 2114c, 2114d in medial and lateral femoral paddles 2110, 2112 enter into a distal end 2128 of the femur 2104, such as, for example, into at least the medial and lateral condyles, respectively, of the femur 2104. FIG. 54 provides an example illustration of the location of the distal holes 2126 formed in the distal end 2128 (FIG. 51) of the femur 2104 via pins that were inserted into the paddle holes 2114c, 2114d in medial and lateral femoral paddles 2110, 2112 of the femoral cutting block 2100. As is apparent, FIG. 54 depicts a portion of the distal holes 2126 that extend through a cut surface 2130 of the femur 2104 that was formed via resection of at least a portion of the distal end 2128 of the femur 2104.

The second set of pin holes, or paddle holes, 2114c, 2114d of the femoral cutting block 2100 can be oriented relative to each other based on a particular design of the implant type, such as, for example, the design of the associated model, brand, and/or manufacturer of knee implant system, that is being, or will be, implanted in the patient. Moreover, the paddle holes 2114c, 2114d of the femoral cutting block 2100 can be oriented relative to each other to correspond to the location and/or orientation at which the distal holes 2126 are, or are to be, in the femur 2104 for the particular implant system that is being, or will be, implanted in the patient. Further, such relative locations of the distal holes 2126 in the femur 2104 can be implant specific in that, for example, the location and/or orientation of the distal holes 2126 in the femur 2104, and associated pins therein, for one particular knee implant system may be different from the location and/or the position of such distal holes 2126 for other knee implant systems.

Thus, for example, the paddle holes 2114c, 2114d of a first femoral cutting block 2100 may have a first configuration, such as, for example, a relative location and/or orientation about the medial and lateral femoral paddles 2110, 2112 of the first femoral block 2100, that corresponds to the relative location and/or orientation at which the distal holes 2126 are to be positioned in the femur 2104 based on the particular design of a first knee implant system, while a different second femoral cutting block 2100 can have paddle holes 2114c, 2114d at second configuration such as, for example, a relative location and/or orientation about the medial and lateral femoral paddles 2110, 2112 of the second femoral block 2100, that corresponds to the particular design of a second, different knee implant system, the first configuration being different from, and not compatible with, the second configuration. In such situations, the differences between, and incompatibility of, the first and second configurations of the paddle holes 2114c, 2114d of the different first and second cutting blocks may, traditionally, preclude the surgeon from being able to properly use the second femoral cutting block 2100 in connection with the implantation of the first knee implant system.

Figure 53:
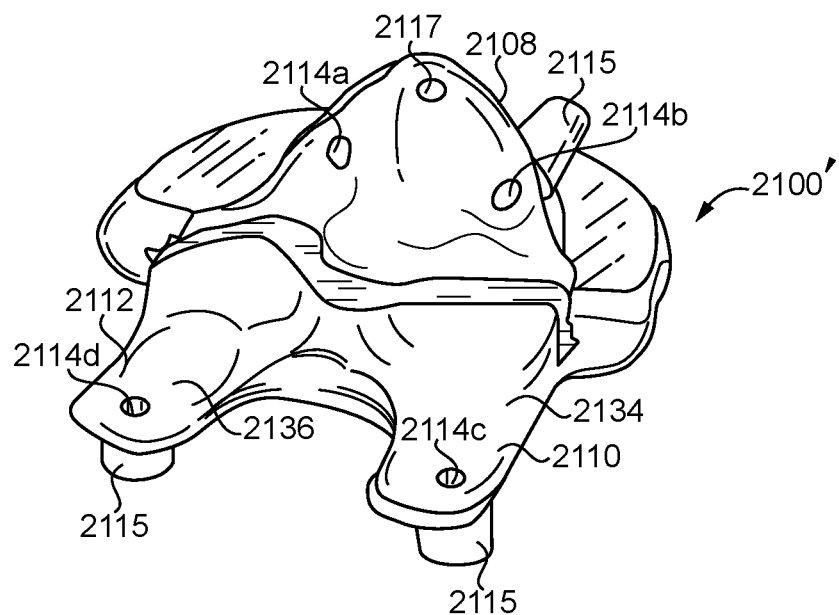
FIG. 53 illustrates a proximal posterior view of another exemplary femoral cutting block.

FIG. 53 illustrates bone facing surfaces of another exemplary femoral cutting block 2100'. As shown, the femoral cutting block 2100' can include an anterior interfacing portion 2132, a medial interfacing portion 2134, a lateral interfacing portion 2136, and an intercondylar interfacing portion 2138. According to at least certain embodiments, the anterior interfacing portion 2132 can be positioned to overlie a portion of the anterior face 2122 of cartilage and bone of, and/or around, the femur 2104. The medial interfacing portion 2134, lateral interfacing portion 2136, and intercondylar interfacing portion 2138 can overlie the medial, lateral and intercondylar notch portions of the condyles, respectively. As shown by FIG. 53, according to at least certain embodiments, the recut holes 2114a, 2114b can extend through the anterior interfacing portion 2132, while the paddle holes 2114c, 2114d can extend through one or both of the medial and lateral interfacing portions 2134, 2136.

Figure 55A:
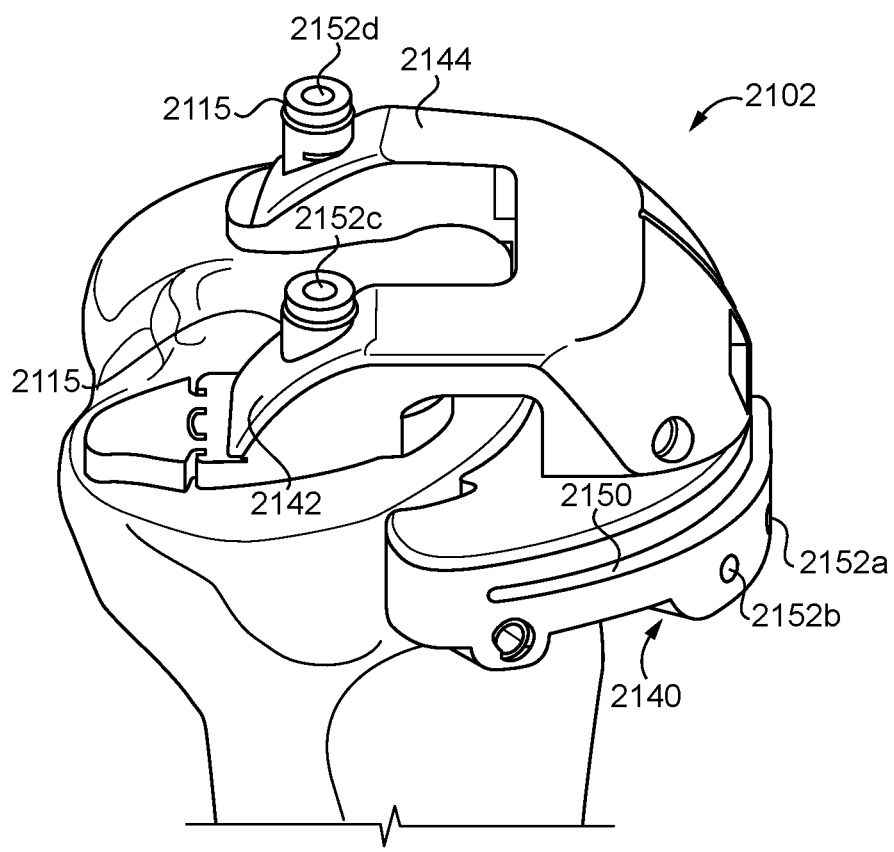
FIGS. 55A and 55B illustrate a proximal lateral view and a proximal anterior perspective view, respectively, of the exemplary tibial cutting block depicted in FIG. 51.
Figure 55B:
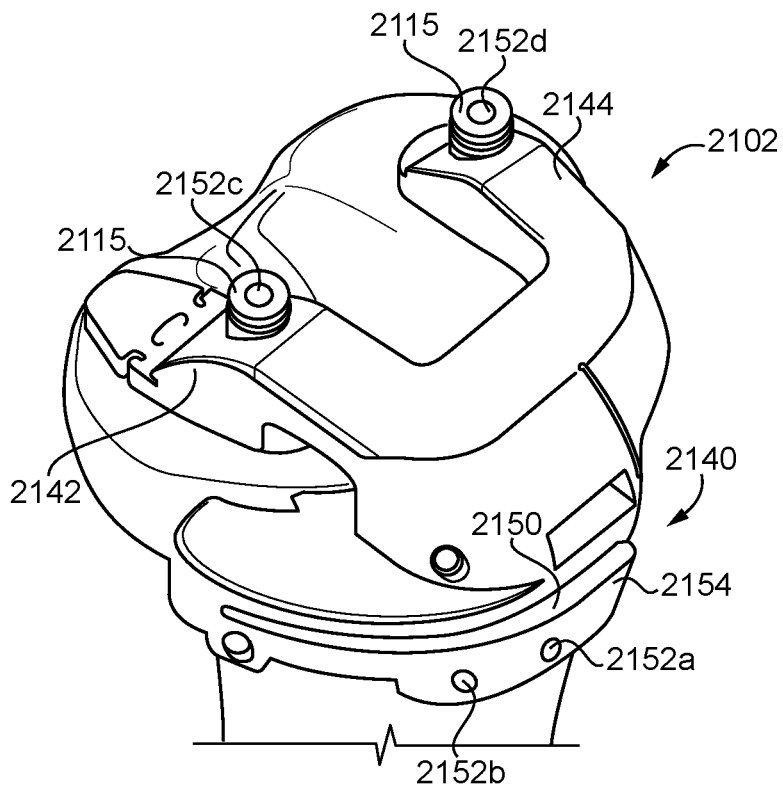

Referencing FIGS. 51, 55A and 55B, the tibial cutting block 2102 can include an anterior tibial portion 2140, a medial tibial paddle 2142, and a lateral tibial paddle 2144. The anterior tibial portion 2140 can be configured to overly a portion of the of the anterior face 2146 of the tibia 2106, while the medial and lateral tibial paddles 2142, 2144 can be configured to overly at least portions of the medial plateau and lateral plateau of the tibia 2106, respectively. Further, although not illustrated, the anterior tibial portion 2140, medial tibial paddle 2142, and lateral tibial paddle 2144 of the tibial cutting block 2102 can include bone interfacing surfaces that are configured to interact with opposing portions of the proximal end 2148 of the tibia 2106 and/or associated cartilage at or around the tibia 2106.

The tibial cutting block 2102 can include a cutting slot 2150 that is that is sized to receive insertion of a cutting blade that can cut or resect the tibia 2106. According to the illustrated embodiment, the cutting slot 2150 is oriented on the medial half of the anterior side of the tibial cutting block 2102. The cutting slot 2150, as well as the cutting slot 2118 of the femoral cutting block 2100, can be formed through the bone interfacing portions of the associated cutting block 2100, 2102, or may be recessed from the bone interfacing surfaces. The thickness of the cutting slots 2118, 2150 can help direct the orientation of the cutting tool, such as, for example, saw blade, as the cutting tool advances through the cutting slot 2118, 2150. Further, the translation of the cutting slot 2118, 2150 relative to the femoral cutting block 2100 and tibial cutting block 2102, respectively, can, according to at least certain cutting blocks 2100, 2102, at least assist in setting a resection depth.

The tibial cutting block 2102 can include a plurality of pin holes 2152a-d. Similar to the pin holes 2114a-d of the femoral cutting block 2100, the pin holes 2152a-d of the tibial cutting block 2102 can be configured to receive pins that are inserted and/or driven into a portion of the tibia 2106. As discussed below, at least some of the pin holes 2152a, 2152b can be used to at least secure the tibial cutting block 2102 to the tibia 2106, and some, but not necessarily all, of the pin holes 2152c, 2152d can also be used in connection with pins and/or associated holes in the tibia 2106 that can assist in aligning the component of the implant system that will be implanted in the patient. Further, at least some of the pins and/or associated pin holes in the tibia 2106 that can be associated with use of the tibial cutting block 2102 can also be used for other preparatory tools during different stages of the implantation procedure.

Figure 56:
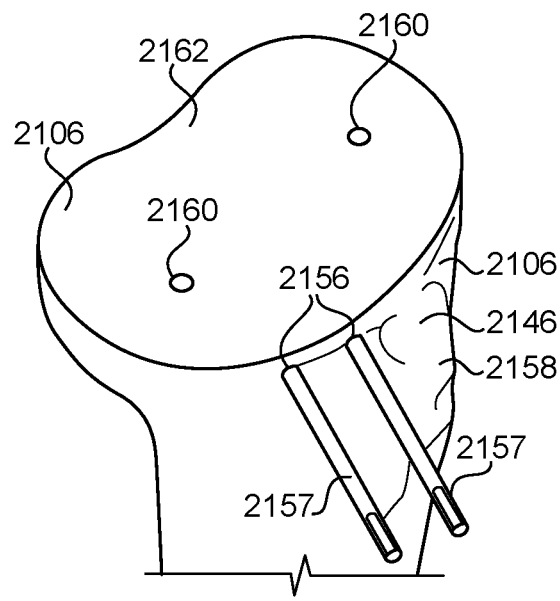
FIG. 56 illustrates a proximal anterior perspective view of a portion of a resected tibia having proximal pin holes and pins extending from recut pin holes.

A first set of one or more of the pin holes 2152a, 2152b of the tibial cutting block 2102, referred to herein as recut holes 2152a, 2152b, can be oriented on an anterior face portion 2154 of the tibial cutting block 2102, including, for example, generally at or in relative proximity to the cutting slot 2150. According to the illustrated embodiment, the recut holes 2152a, 2152b can each be oriented to receive passage of a pin that enters, and is inserted into, the anterior face 2158 of the tibia 2106. FIG. 56 provides an example location in the tibia 2106 at which pins 2157 that can be driven through the recut holes 2152a, 2152b of the exemplary tibial cutting block 2102 can form recut holes 2156 through the anterior face 2158, and into a portion, of the tibia 2106, respectively. While the pins 2157 shown in FIG. 56 are depicted as extending only from the recut holes 2156 in the tibia 2106, similar pins 2157 can be used in connection with the other pin holes 2114a-d, 2152c, 2152d of the femur and tibial cutting blocks 2100, 2102 and corresponding pin holes 2124, 2126, 2160 of the femur 2104 and tibia 2106. Additionally, according to certain embodiments, one or more of the recut holes 2152a, 2152b can have guide bosses 2115 similar to the guide bosses 2115 discussed above with respect to recut holes 2114a, 2114b of the femoral cutting block 2100. Alternatively, or optionally, as depicted in FIGS. 51, 55A and 55B, one or more of the recut holes 2152a, 2152b can be generally flush with the adjacent surface of the anterior face 2158 of the tibia 2106.

A second set of one or more pin holes 2152c, 2152d, referred to herein a paddle holes 2152c, 2152d, can extend through one or more of the medial and lateral tibial paddles 2142, 2144. As shown for example by at least FIGS. 55A and 55B, according to the illustrated embodiment, the medial and lateral tibial paddles 2142, 2144 can each include one of the one or more paddle holes 2152c, 2152d. Further, according to the illustrated embodiment, the paddle holes 2152c, 2152d can be located at the proximal end 2148 of the tibia 2106. According to the illustrated embodiment, the paddle holes 2152c, 2152d can be positioned such that, when the tibial cutting block 2102 is operably positioned on the proximal end 2148 of the tibia 2106, pins that extend through the paddle holes 2152c, 2152d in medial and lateral tibial paddles 2142, 2144 can enter into the proximal end 2148 of the tibia 2106. FIG. 56 provides an example illustration of the location of the proximal holes 2160 formed in the proximal end 2148 of the tibia 2106 that are positioned to receive pins that are inserted into the paddle holes 2152c, 2152d in medial and lateral tibial paddles 2142, 2144 of the illustrated exemplary tibial cutting block 2102. As is apparent, FIG. 56 depicts a portion of the proximal holes 2160 extending through a cut surface 2162 of the tibia 2106 that was formed via resection of at least a portion of the proximal end 2148 of the tibia 2106.

Similar to the above-discussed paddle holes 2114c, 2114d of the femoral cutting block 2100, the second set of pin holes, or paddle holes, 2152c, 2152d in medial and lateral tibial paddles 2142, 2144 of the tibial cutting block 2102 can also be oriented relative to at least each other based on the particular design of a pin hole configuration for the implant type, such as, for example, model, brand and/or manufacturer of the knee implant system that is being, or will be, implanted in the patient. Moreover, the paddle holes 2152c, 2152d of the tibial cutting block 2102 can be oriented relative to each other to correspond to the location and/or orientation at which the proximal holes 2160 are, or are to be at, in the tibia 2106 for the design of the particular implant system that is being, or will be, implanted in the patient. Thus, for example, the paddle holes 2152c, 2152d of a first tibial cutting block 2102 can have a first configuration, such as, for example, a relative location and/or orientation, about the medial and lateral tibial paddles 2142, 2144 that correspond to the relative location and/or orientation at which the proximal holes 2160 are to be positioned in the tibia 2106 for the design of a first knee system, while another, different second tibial cutting block 2102 can have paddle holes 2152c, 2152d having a second configuration that corresponds to the relative location and/or orientation at which the proximal holes 2160 are to be positioned in the tibia 2106 for the design of a second, different knee system, the first configuration being different from, and not compatible with, the second configuration. In such situations, the differences between the first and second configurations of the paddle holes 2152c, 2152d, and associated incompatibility, can again traditionally preclude the surgeon from being able to properly use the second tibial cutting block 2102 in connection with the implantation of the first knee implant system.

Accordingly, certain types of implant systems can be designed so that the location and/or orientation of certain pin holes, and/or the pins that are received therein, are implant specific in that the positions of the holes and/or associated pins in the patient's bone(s) may be part of aligning a component(s) of that particular implant system that will be implanted in the patient. Thus, such implant specific pin holes and associated pins can have relative an orientation(s)

or position(s) that is/are unique to that particular implant system. For example, as previously discussed, with respect to knee implant systems, the relative location and/or orientation of distal holes 2126 that are, or are to be, formed in the distal end 2128 of the femur 2104, and/or the relative location and/or orientation of proximal holes 2160 that are, or are to be, formed in the proximal end of the tibia 2106, can be generally specific to the type of implant device being implanted, such as, for example, the model, brand, and/or manufacturer of the implant system.

Thus, for example, with respect to the above-discussed femoral and tibial cutting blocks 2100, 2102, the associated paddle holes 2114c, 2114d, 2152c, 2152d can have configurations that are compatible with the pin hole configuration for a particular knee implant system, and that pin hole configuration may be different from, as well as incompatible with, a similar type of pin hole configuration or design for other knee implant systems. Accordingly, when the associated femoral and tibial cutting block 2100, 2102 is properly positioned on the femur 2104 or tibia 2106, the paddle holes 2114c, 2114d, 2152c, 2152d can generally align with, and/or be positioned at similar locations and/or orientations as, the actual or intended locations of the corresponding implant specific pin holes, namely the distal and proximal holes 2126, 2160 in the femur 2104 or tibia 2106, respectively, for one knee implant system, but may not be positioned for proper alignment with the distal or proximal holes 2126, 2160 in the femur 2104 or tibia 2106 for other knee implant systems.

Conversely, other, non-implant-specific pin holes, and the associated pins positioned therein, can be used to secure and/or position certain implant preparatory tools used in connection with preparing bone 2104, 2106 to receive an implant, but generally may not be used in connection with the eventual aligning of a component(s) of the implant system that will be implanted in the patient. For example, with respect to at least knee implant systems, recut holes 2124, 2156 in the anterior face 2122, 2146 of the femur 2104 and tibia 2106, respectively, can be used in connection with securing and/or positioning a cutting block, and/or a recut cutting block, to the femur 2104 or tibia 2106, but may not themselves be used in connection with aligning a component of the knee implant system that will be eventually implanted in the patient. Thus, preparatory implant tools, such as, for example, femoral and tibial cutting blocks 2100, 2102, can include both pin holes having configurations that are similar to, or otherwise compatible with, an implant-specific pin hole configuration of the implant system that is being implanted, such as, for example, the above-discussed paddle holes 2114c, 2114d, 2152c, 2152d, as well pin holes that have non-implant-specific pin hole configurations, such as, for example, recut holes 2114c, 2114d, 2152c, 2152d.

According to certain embodiments, preparatory tools designed for particular implant systems can be adapted for use with other implant systems. Moreover, for example, a first preparatory tool, such as, for example, a first cutting block, can be built for use with another implant system, such as, for example, a second implant system, for which the first preparatory tool was not specifically designed. Such building of the first preparatory tool for use with the implantation of the other system can include modifying a portion of that first preparatory tool so that the modified portion of the first preparatory tool conforms to the corresponding design of the other knee implant system, but may not necessarily, or no longer, conforms to the corresponding design of the first implant system.

For example, according to certain embodiments, a first preparatory tool, such as, for example, a cutting block, can be designed to have one or more first pin holes along a first pin hole configuration, the first pin holes and first pin hole configuration being specific to at least a first implant system. However, a surgeon may wish to use that first preparatory tool in connection with a second implant system. Yet, the second implant system may use a second preparatory tool in a manner similar to the intended use of the first preparatory tool that has one or more second pin holes along a second pin hole configuration that is not compatible with the first pin hole configuration of the first preparatory tool. According to certain embodiments, the surgeon can have the option of selecting that first preparatory tool for use with the implantation of the second implant system, and, based on that selection, have one or more features of the first preparatory tool be built to have features and/or a configuration that allows the first preparatory tool be compatible with the second implant system. Moreover, under the current example, the selected first preparatory can be built such that the first preparatory tool includes the second pin holes are arranged in accordance with the second pin hole configuration.

Figure 57A:
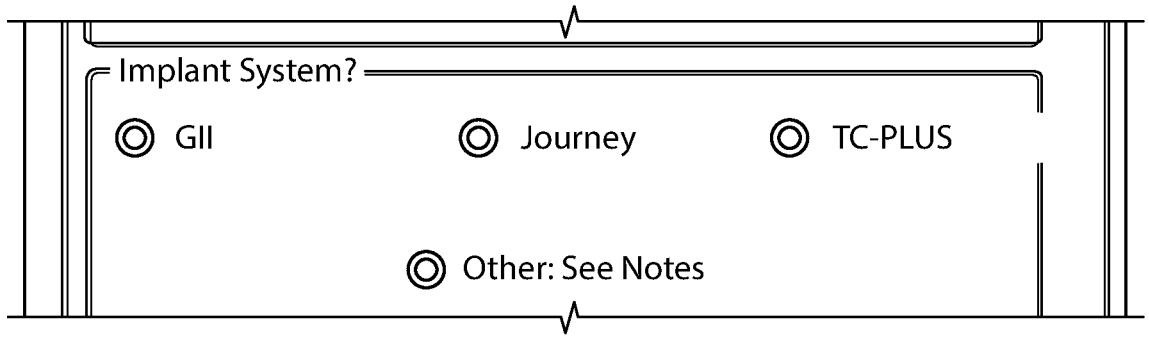
FIGS. 57A and 57B illustrate exemplary representations of snapshots of a portion of a graphical display on a display presenting selectable options pertaining to knee implant systems and various different femoral cutting blocks.
Figure 57B:
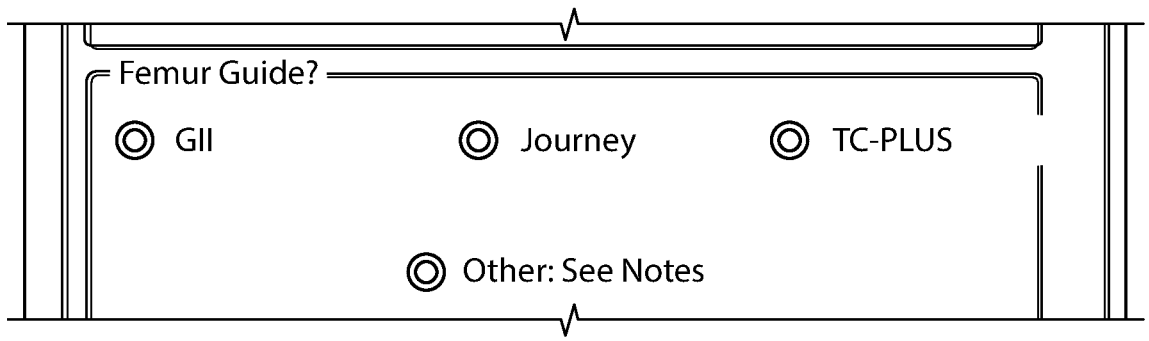

FIGS. 57A and 57B illustrate exemplary representations of snapshots of a portion of a graphical display presenting selectable options pertaining to knee implant systems and various different femoral cutting blocks. Such graphical displays can, for example, be provided from a variety of different sources, including, for example, via an on-line display from a manufacturer, that can be accessed via at least the internet. As shown, in the example provided by FIG. 57A, a user, such as, for example, a surgeon, has the opportunity to indicate a knee system that has been or may be selected, for implantation in a patient. Moreover, in the illustrated example, the user is provided the opportunity to select, or identify, from a plurality of knee implant systems, the particular knee implant system that has been, or may be, selected for implantation in the patient, such as, for example, specifically identify one of "GII", "Journey", and "TC-PLUS", along with the opportunity to select an "Other" option.

According to certain embodiments, after indicating the knee system that has been, or may be, selected, for implantation in the patient, the user can be presented the option of selecting particular preparatory tools for use during the implantation procedure. As shown by FIG. 57B, the preparatory tools available for selection, such as, for example, a femur guide, can include both tools that were designed specifically for the implant system that was selected in connection with FIG. 57A, as well as other alternative preparatory tools that were designed for other, different implant systems. For example, with reference to FIG. 57A, if the user selected the "Journey" knee implant system, then that user may be also presented the option of using at least some of the preparatory tools designed for that selected knee implant system, such as the "Journey" femur guide. However, as shown by FIG. 57B, the user can also be presented the option of selecting for use other, alternative preparatory tools that were not specifically designed for the selected knee implant system, such as, for example, selecting to use the femur guides that were designed for the "GII" or "TC-PLUS" knee implant systems. A determination of which other, alternative preparatory tools will be provided as user selectable options for a particular selected implant system can be based on a variety of different factors, including, for example, the ability to modify the other, alternative preparatory tool for use with selected, different implant system, the manufacturer(s) of the selected implant system and/or the preparatory tool, and/or the availability of the preparatory tool, among other considerations.

As discussed above, to the extent necessary, the selected other, alternative preparatory tool can be built, or otherwise be modified, to be compatible with at least certain aspects of the selected, different implant system. For example, with respect to the above-discussed femoral cutting block 2100, if needed, one or more of the recut holes 2114a, 2114b can each be oriented on the selected other, alternative preparatory tool so as to be at relative locations and/or orientations that is/are compatible with the recut pin hole configuration that is used by the femoral cutting block that was specifically designed for use with the selected knee implant system. Similarly, if needed, the paddle holes 2114c, 2114d can also be positioned and/or oriented at locations that correspond to the locations at which the pin holes are to be positioned at the distal end 2128 of the femur 2104. Thus, by providing such options to the user, a surgeon may be able to select for use, and have built in conformance with, a preparatory tool of the surgeon's choice or preference despite that preparatory tool not being specific to the implant system that the surgeon is implanting. Further, while the above-discussed example is discussed with respect to femur cutting blocks, similar features are also applicable to other preparatory tools for knee implant systems, as well as other types of implant systems, including, but not limited to, hip, shoulder, and wrist implant systems, among others.

According to other embodiments of the subject application, preparatory tools for implant procedures can be identified as being compatible for use different implant systems based on similarities or compatibility of non-implant-specific pin hole configurations. Such a system can provide surgeons with the option to select a particular tool, such as, for example, a cutting block or recut cutting block, that may not be specific to the implant system being implanted, but which has pin holes having a configuration(s) that is/are similar to, or otherwise compatible with, the configuration of the non-implant-specific pin holes of the implant system that is being implanted. Thus, such a system may, for at least certain bone preparatory procedures, provide an indication of preparatory tools that, although not specifically designed for the implant system that is, or is to be, implanted in the patient, are suitable alternatives, such as, for example, capable of being secured to the bone 2104, 2106 using the same pins and/or pin holes 2124, 2156 in the femur 2104 or tibia 2106 as other preparatory tools that are specific to the implant system that is being implanted in the patient. In addition to allowing surgeons to use tools that, although not designed specifically for the system that is being implanted, are compatible with that system, such a system can also enhance the likelihood that a surgeon can use a tool of the surgeon's preference, or for which the surgeon has more familiarity, experience, and/or training. Further, if needed, the selected alternative implant tool can be modified, manufactured, or otherwise provided with other pin holes that correspond to the configuration of at least some implant specific holes of the implant system being implanted.

For example, during at least certain operations, a cutting block, such as, for example, the femoral and/or tibial cutting block 2100, 2102, can be used to resect portions of the distal end 2128 of the femur 2104 and the proximal end 2148 of the tibia 2106. As previously discussed, such a procedure can include inserting pins 2157 into recut holes 2124, 2156, as well as into distal and proximal holes 2126, 2160 in the femur and tibia 2104, 2106, respectively. Such recut holes 2124, 2156 in the femur and tibia 2104, 2106, respectively, can be positioned on the respective bone 2104, 2106 in at a non-implant-specific pin hole configuration, as those pin holes 2124, 2126, as those recut holes 2124, 2156 may not be used to align the subsequently implanted component of the implant system.

In at least certain circumstances, following resection of the femur 2104 and/or tibia 2106, the surgeon may elect to recut one or both of the bones 2104, 2106. For example, during the cutting procedure, the blade in the cutting slot 2118, 2150 may deflect in a direction toward or away from the bone, and/or the cut may not necessarily extend far enough into the bone, such that the surgeon may elect to proceed with a recut of that bone(s) 2104, 2106. In such a situation, according to certain embodiments, rather than being limited to using a recut cutting block that is specific to the implant system that is being implanted, other recut cutting blocks that are designed for other, different implant systems can be selected for use based on those other or alternative recut blocks having a non-implant-specific pin holes that is/are compatible with the configuration of the non-implant-specific recut holes 2124, 2156 formed in the bone 2104, 2106.

For example, in connection with the presently discussed knee implant example, one or more alternative recut cutting blocks that are not specific to the knee implant system being implanted, may be identified based on those alternative recut cutting blocks providing a recut pin hole configuration that is compatible with the configuration of the recut holes 2114a, 2114b, 2152a, 2152b of the femoral and/or tibial cutting block(s) 2100, 2102 and/or the configuration of the recut holes 2124, 2156 that are, or will be, formed in the corresponding bone(s) 2104, 2106.

With reference to the identified alternative recut cutting blocks, a decision can be made, such as, for example, by the surgeon, as to whether to select for use in a recut procedure one of the alternative recut cutting blocks, or to otherwise proceed with a recut cutting block that is specific to the implant system that is being implanted. Such a selection can be based on a variety of different factors, including, but not limited to, the surgeon's familiarity or preference with respect to the available recut cutting blocks and the recut cutting block of the system being implanted. Further, in the event an alternative recut cutting block is selected, in at least certain situations, the option can be available to provide the selected alternative recut cutting block with the implant-specific pin holes. For example, according to the discussed example, the option may be provide to have the selected alternative recut cutting block modified to have the recut cutting block have paddle holes at locations that correspond to location and orientation of the paddle holes 2114c, 2114d, 2152c, 2152d in the femoral and/or tibial cutting block 2100, 2102 used, or that will be used, to make the initial cut in the bone 2104, 2106, and/or are compatible to the relative location(s) of the distal and/or proximal holes 2126, 2160 that are in, or otherwise are to be formed in, the bone 2104, 2106.

While the above example is discussed in terms of selection of an alternative recut tool, a similar process can also be available for other preparatory tools, including, but not limited to, the selection of a femoral and/or tibial cutting blocks 2100, 2102 that may be used for the initial cut(s) of the distal and proximal ends 2128, 2148 of the femur and tibia 2104, 2106, respectively, among other preparatory tools. Additionally, such other preparatory tools are not limited to planner slot cut blocks. For example, according to certain embodiments, the above-discussed processes can include selection of a planning reamer, among other tools, for resurfacing procedures. Additionally, at least some of the pins associated with the above-discussed procedures, such as, for example, recut pin holes 2114c, 2114d, 2152c, 2152d, can also be arranged and/or configured to receive sensors that can, for example, be utilized for computer-aided surgery or ligament balancers, among other uses. Further, while the examples discussed herein are with respect to knee implant systems and tools, embodiments of the subject application are also applicable to other implant devices.

Figure 52:
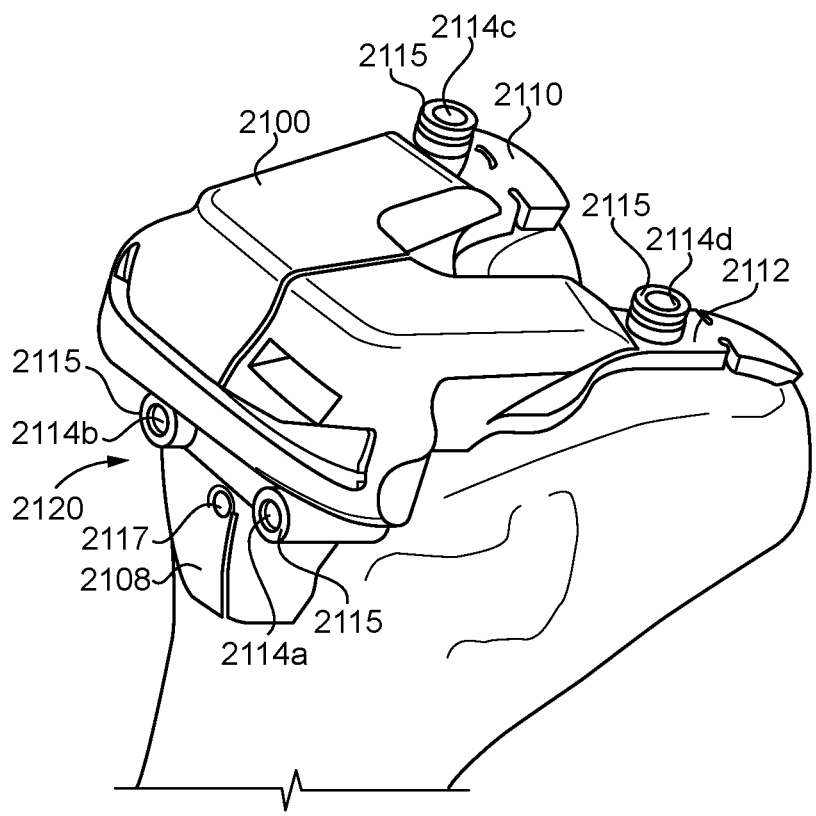
FIG. 52 illustrates a distal anterior view of the exemplary femoral cutting block depicted in FIG. 51.
Figure 58A:
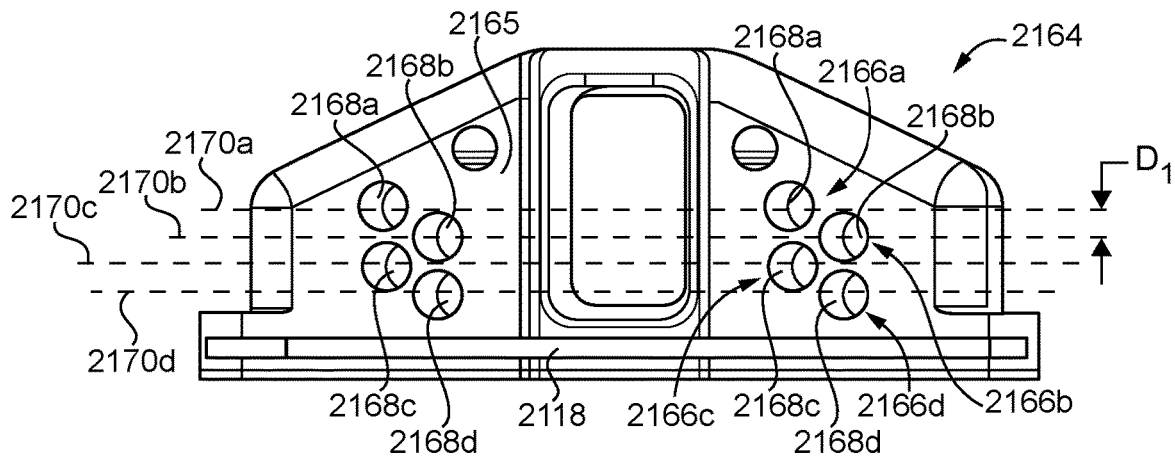
FIGS. 58A and 58B illustrate anterior and distal views, respectively, of an exemplary femoral recut cutting block having a plurality of recut pin hole sets.
Figure 58B:
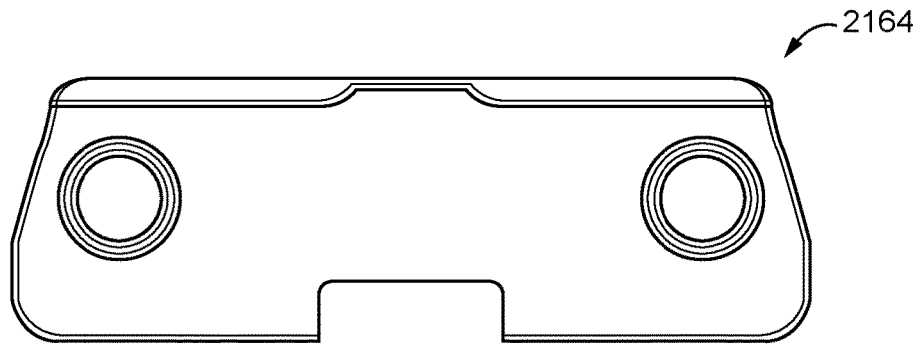

FIGS. 58A and 58B illustrate anterior and distal views, respectively, of an exemplary femoral recut cutting block 2164 that is designed for an implant knee system that is different from the knee implant system for which the femoral cutting block 2100 depicted in FIGS. 51 and 52 is designed. According to the illustrated example, the femoral recut cutting block 2164 has a plurality of sets of non-implant-specific pin holes that are similar to, or compatible with, the non-implant-specific holes of the femoral cutting block 2100. Moreover, in the illustrated example, the femoral recut cutting block 2164 has four recut hole sets 2166a-d, each set having at least two recut holes 2168a-d that extend through an anterior face portion 2165 of the femoral recut cutting block 2164. Further, the recut holes 2168a-d in each recut hole set 2166a-d have a relative arrangement similar to the non-patient-specific pin holes of at least the femoral cutting block 2100 depicted in FIGS. 51 and 52, and more specifically, the recut holes 2114a, 2114b of the illustrated femoral cutting block 2100. Thus, each set of the recut holes 2168a-d in the femoral recut cutting block 2164 can be arranged in a manner that is compatible with the location and orientation of the recut holes 2124 that are, or are to be, formed in the femur 2104, as well as the associated location and/or orientation of the pins 2157 that are (or are to be) inserted therein.

For example, the femoral recut cutting block 2164 depicted in at least FIG. 58A has a first recut hole set 2166a comprising a pair of recut holes 2168a that have a relative location and/or orientation to each other that is similar to the relative location and/or orientation of the recut holes 2114a, 2114b of the femoral cutting block 2100 depicted in FIGS. 51 and 52. Similarly, the illustrated femoral recut cutting block 2164 also includes second, third, and fourth recut sets 2166b-d, each set 2166b-d also comprising a pair of recut holes 2168b-d having a relative location and/or orientation that corresponds to the relative location and/or orientation of the recut holes 2114a, 2114b of the femoral cutting block 2100 depicted in FIGS. 51 and 52. Thus, according to such an embodiment, similar to the recut holes 2114a, 2114b of the femoral cutting block 2100, the recut holes 2168a-d of any of the recut hole set 2166a-d of the depicted femoral recut cutting block 2164 can be generally, and selectively, aligned at the same position relative to the corresponding recut holes 2124 in the femur 2104.

Additionally, in the illustrated example, each recut hole set 2166a-d of the femoral recut cutting block 2164 is generally aligned along an axis 2170a-d, each axis 2170a-d being offset from the axis 2170a-d of the adjacent recut hole set 2166a-d by a linear distance generally along the distal-proximal axis. For example, according to the embodiment depicted in FIG. 58A, the recut holes 2168a of the first recut hole set 2166a are linearly offset from the recut holes 2168b of the second recut set 2166b by a linear distance in the general direction of the distal-proximal axis by a first linear distance (as represented by "$D_1$" in FIG. 57). The linear distance of such an offset between each of the adjacent recut hole sets 2166a-d can generally be the same, or alternatively, can vary. Further, according to certain embodiments, the offset distance between one or more of the recut hole axes 2170a-d can generally correspond to the thickness of resection to the next implant thickness.

Figure 58C:
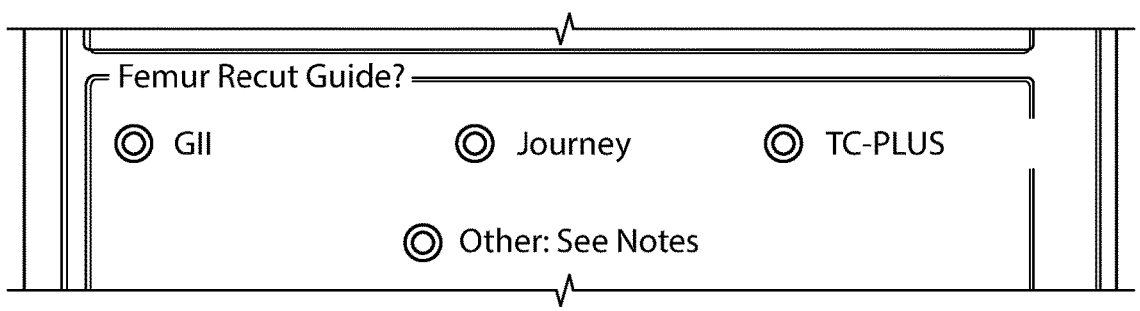
FIG. 58C illustrates an exemplary representation of a snapshot of a portion of a graphical display on a display presenting selectable options pertaining to alternative femoral recut cutting blocks.

Thus, according to the illustrated embodiment, as the non-implant-specific pin holes, in this example, recut holes 2168a-d in each set of recut hole sets 2166a-d, of the femoral recut cutting block 2164 are compatible with at least the recut holes 2114a, 2114b of the femoral cutting block 2100 that, unlike the femoral recut cutting block 2164, was designed for the implant system being implanted, the femoral recut cutting block 2164 can be identified as a suitable alternative femoral recut cutting block. For example, FIG. 58C illustrates an example of a graphical display on a display of a plurality of surgeon selectable alternative femoral recut cutting blocks (viz. "GII", "JOURNEY", and "TC-PLUS") that, despite being designed for use with other knee implant systems, have non-implant-specific pin holes that are compatible with similar non-implant-specific pin holes of the knee system that is being implanted. Thus, each of these alternative femoral recut cutting blocks, which, again, may be associated with knee implant systems that are different from the knee implant system that is being implanted, may be deemed suitable for use with the particular knee implant system that is being implanted, and thereby provide a variety of options of femoral recut cutting blocks, and their associated designs, that could be selected by the surgeon for use during an implantation procedure. Further, to the extent that the selected alternative femoral recut cutting block may need to also include patient specific pin holes, such as, for example, the above-discussed paddle holes 2114c, 2114d, the selected alternative femoral recut cutting block could be adjusted, manufactured, or otherwise provided to also include those implant-specific recut pin holes.

Figure 59A:
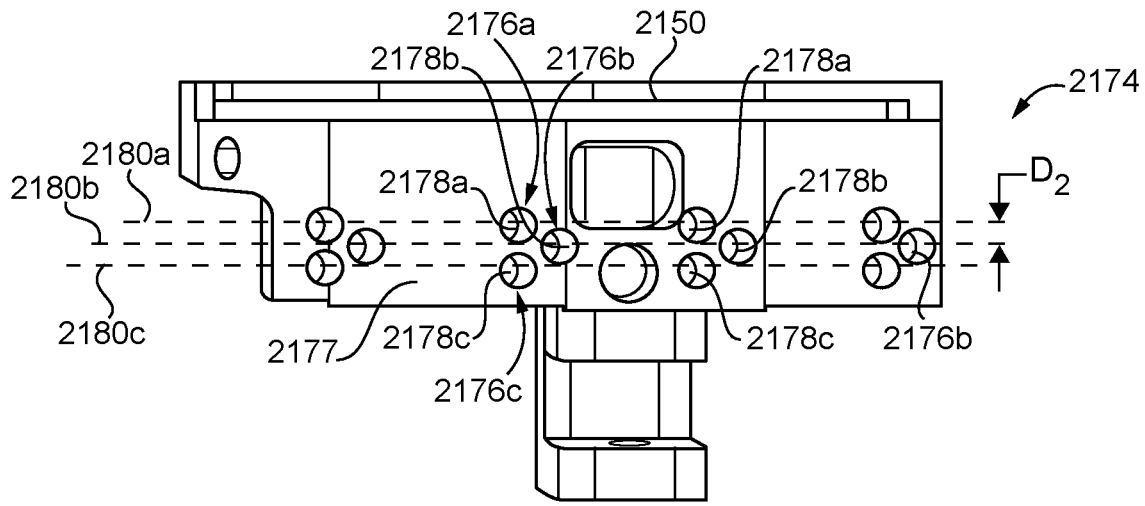
FIGS. 59A and 59B illustrate anterior and proximal views, respectively, of an exemplary tibial recut cutting block having a plurality of recut pin hole sets.
Figure 59B:
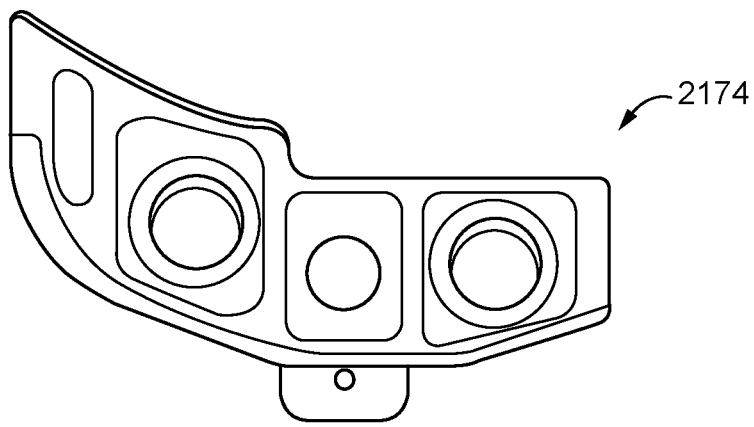
Figure 59C:
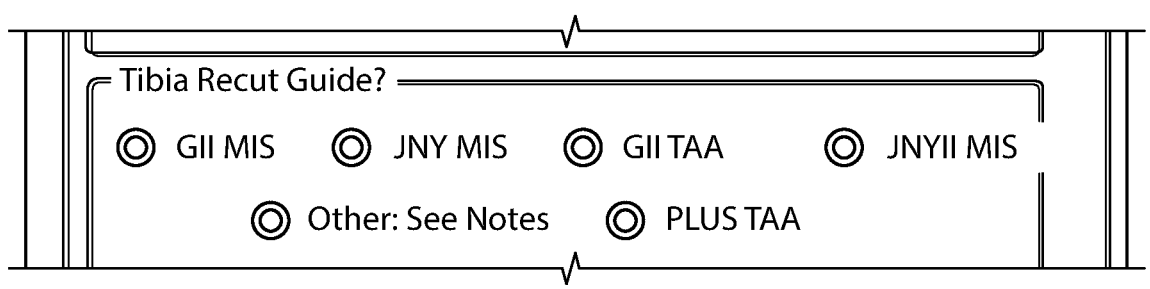
FIG. 59C illustrates an exemplary representation of a snapshot of a portion of a graphical display on a display presenting selectable options pertaining to alternative tibial recut cutting blocks.

FIGS. 59A and 59B illustrate anterior and distal views, respectively, of an exemplary tibial recut cutting block 2174 that is designed for an implant knee system that is different from the knee implant system for which the tibial cutting block 2102 depicted in FIGS. 51, 55A and 55B is designed. Similar to the above-discussed femoral recut cutting block 2164, according to the illustrated example, the tibial recut cutting block 2174 has a plurality of sets of non-implant-specific pin holes having configurations that are each similar to, or compatible with, the corresponding configuration of the non-implant-specific pin holes of the tibial cutting block 2102. Moreover, in the illustrated example, the tibial recut cutting block 2174 has three recut hole sets 2176a-c, each set having at least two recut holes 2178a-c that extend through an anterior face portion 2177 of the tibial recut cutting block 2174. Further, the recut holes 2178a-c in each recut hole set 2176a-c have a relative configuration similar to, or compatible with, the configuration of the non-patient-specific pin holes of at least the tibial cutting block 2102 depicted in FIGS. 51, 55A and 55B, and more specifically, the configuration of the recut holes 2152a, 2152b of the illustrated tibial cutting block 2102. Thus, in the illustrated example, each set of the recut holes 2178a-c in the tibial recut cutting block 2174 is arranged in a manner that is compatible with the configuration, such as the relative location and/or orientation, of the recut holes 2156 that are, or are to be, formed in the femur 2106, as well as the associated location and/or orientation of the pins 2157 that are (or are to be) inserted therein.

For example, the tibial recut cutting block 2174 depicted in at least FIG. 59A has a first recut hole set 2166a comprising a pair of recut holes 2168a that have a configuration relative to each other that is similar to the configuration of the recut holes 2152a, 2152b of the tibial cutting block 2102 depicted in FIGS. 51, 55A and 55B. Similarly, the illustrated tibial recut cutting block 2174 also includes second and third recut sets 2166b, 2166c, each set 2166b, 2166c also comprising a pair of recut holes 2168b, 2168c having a configuration that corresponds to the configuration of the recut holes 2152a, 2152b of the tibial cutting block 2102 depicted in FIGS. 51, 55A and 55B. Thus, according to such an embodiment, similar to the recut holes 2152a, 2152b of the tibial cutting block 2102, the recut holes 2168a-c of any of the recut hole sets 2166a-c of the depicted tibial recut cutting block 2174 can be generally aligned and/or positioned at the same location relative to the corresponding recut holes 2156 in the tibia 2106.

Additionally, in the illustrated example, each recut hole set 2176a-c is generally aligned along an axis 2180a-c, each axis 2180a-c being offset from the axis 2180a-c of the adjacent recut hole set 2176a-c by a linear distance generally along a distal-proximal axis. For example, according to the embodiment depicted in FIG. 59A, the recut holes 2178a of the first recut hole set 2176a are linearly offset from the recut holes 2178b of the second recut set 2176b by a linear distance in the distal-proximal axis by a linear distance (as represented by "$D_2$" in FIG. 59A). The linear distance of such an offset between each of the adjacent recut hole sets 2176a-c can generally be the same, or alternatively, can vary. Further, according to certain embodiments, the offset distance between one or more of the recut hole axes 2180a-c can generally correspond to the thickness of resection to the next implant thickness.

Thus, according to the illustrated embodiment, as the non-implant-specific pin holes, in this example recut holes 2178a-c in each set of recut hole set 2176a-c, of the tibial recut cutting block 2174 are compatible with the recut holes 2152a, 2152b of the tibial cutting block 2102 that, unlike the tibial recut cutting block 2174, was designed for the implant system being implanted, the tibial recut cutting block 2174 can be identified as a suitable or compatible alternative tibial recut cutting block. For example, FIG. 58C illustrates an example of a plurality of alternative tibial recut cutting blocks (viz. "GII MIS", "JNY MIS", "GII TAA", "JNYII MIS", and "PLUS TAA") that, despite being designed for use with other knee implant systems, have non-implant-specific pin holes having a configuration(s) that is/are compatible with similar non-implant-specific pin holes of the knee system that is being implanted. Thus, each of these alternative tibial recut cutting blocks, which, again, may be associated with knee implant systems that are different from the knee implant system that is being implanted, may be deemed suitable for use with the particular knee implant system that is being implanted, and thereby provide a variety of options of tibial recut cutting blocks, and their associated designs, that could be selected for use by the surgeon for implantation. Further, to the extent that the selected alternative tibial recut cutting block may need to also include patient specific pin holes, such as, for example, the above-discussed paddle holes 2152c, 2152d, the selected tibial recut cutting block could be adjusted, manufactured, or otherwise provided to also include those implant-specific recut pin holes.

There is provided a method comprising prompting, by a graphical user interface presented on a display device of a computing system, a surgeon for a plurality of adaptive tibial guide parameters collectively indicative of a physical structure of a surgeon-specific tibial cutting guide and a plurality of adaptive femoral guide parameters collectively indicative of a physical structure of a surgeon-specific femoral cutting guide for a surgical procedure on a patient, receiving, via the graphical user interface of the computing system, surgeon input from the surgeon associated with the plurality of adaptive tibial guide parameters and the plurality of adaptive femoral guide parameters, and transmitting, via a communication circuitry of the computing system, the received surgeon input to an instrumentation manufacturing system for manufacturing of at least one of the surgeon-specific tibial cutting guide and the surgeon-specific femoral cutting guide.

In some embodiments, the method may further comprise fabricating the surgeon-specific tibial cutting guide using fabrication machinery of the instrumentation manufacturing system.

In some embodiments, the method may further comprise fabricating the surgeon-specific femoral cutting guide using fabrication machinery of the instrumentation manufacturing system.

In some embodiments, the method may further comprise validating the surgeon input to confirm that the plurality of adaptive tibial guide parameters and the plurality of adaptive femoral guide parameters desired by the surgeon are consistent with an anatomy of the patient.

In some embodiments, prompting the surgeon for the plurality of adaptive tibial guide parameters and the plurality of adaptive femoral guide parameters may comprise separately prompting the surgeon for the plurality of adaptive tibial guide parameters and prompting the surgeon for the plurality of adaptive femoral guide parameters.

In some embodiments, prompting the surgeon for the plurality of adaptive tibial guide parameters and the plurality of adaptive femoral guide parameters may comprise prompting the surgeon to select from a distal cut first surgical sequence or a tibial cut first surgical sequence.

In some embodiments, prompting the surgeon for the plurality of adaptive tibial guide parameters and the plurality of adaptive femoral guide parameters may comprise prompting the surgeon to select from a surgeon-specific tibial cutting guide having at least one contact extension to a tibial paddle relative to a standard surgical cutting guide or a surgeon-specific tibial cutting guide without the at least one contact extension.

In some embodiments, the at least one contact extension may be separable from a remainder of the tibial paddle.

In some embodiments, prompting the surgeon for the plurality of adaptive tibial guide parameters and the plurality of adaptive femoral guide parameters may comprise prompting the surgeon to select a thickness of a cutting blade of a cutting instrument to be used with the surgeon-specific tibial cutting guide.

In some embodiments, prompting the surgeon for the plurality of adaptive tibial guide parameters and the plurality of adaptive femoral guide parameters may comprise prompting the surgeon to select from a surgeon-specific tibial cutting guide that is designed for use with a surgical technique in which an alignment rod is aligned parallel to a mechanical axis of the patient's tibia to gauge alignment or a surgeon-specific tibial cutting guide that is designed for use with a surgical technique in which the alignment rod is aligned perpendicular to a cutting slot of the surgeon-specific tibial cutting guide.

In some embodiments, prompting the surgeon for the plurality of adaptive tibial guide parameters and the plurality of adaptive femoral guide parameters may comprise prompting the surgeon to select from a surgeon-specific tibial cutting guide having a least one rimmed pinhole or a surgeon-specific tibial cutting guide without the at least one rimmed pinhole.

In some embodiments, prompting the surgeon for the plurality of adaptive tibial guide parameters and the plurality of adaptive femoral guide parameters may comprise prompting the surgeon to select from a surgeon-specific tibial cutting guide having at least one bicruciate ligament sparing feature or a surgeon-specific tibial cutting guide without the at least one bicruciate ligament sparing feature.

In some embodiments, prompting the surgeon for the plurality of adaptive tibial guide parameters and the plurality of adaptive femoral guide parameters may comprise prompting the surgeon to select at least one preferred standard surgical recut guide.

In some embodiments, prompting the surgeon for the plurality of adaptive tibial guide parameters and the plurality of adaptive femoral guide parameters may comprise prompting the surgeon to select from a surgeon-specific tibial cutting guide having at least one tibial paddle that extends distal to a cut plane of a cutting instrument to contact a proximal surface of the patient's tibia or a surgeon-specific tibial cutting guide with no tibial paddle that extends distal to the cut plane.

In some embodiments, prompting the surgeon for the plurality of adaptive tibial guide parameters and the plurality of adaptive femoral guide parameters may comprise prompting the surgeon to select from a surgeon-specific femoral cutting guide having a least one rimmed pinhole or a surgeon-specific femoral cutting guide without the at least one rimmed pinhole.

There is also provided a system, comprising a computing device having a communication circuitry, at least one input/output device, a processor, and a memory, wherein the memory comprises a plurality of instructions stored thereon that, in response to execution by the processor, causes the computing device to prompt, via a graphical user interface presented on the input/output device, a surgeon for a plurality of adaptive tibial guide parameters collectively indicative of a physical structure of a surgeon-specific tibial cutting guide and a plurality of adaptive femoral guide parameters collectively indicative of a physical structure of a surgeon-specific femoral cutting guide for a surgical procedure on a patient, receive, via the input/output device, surgeon input from the surgeon associated with the plurality of adaptive tibial guide parameters and the plurality of adaptive femoral guide parameters, and transmit, via the communication circuitry, the received surgeon input to an instrumentation manufacturing system for manufacturing of at least one of the surgeon-specific tibial cutting guide and the surgeon-specific femoral cutting guide.

In some embodiments, the system may further comprise the instrumentation manufacturing system configured to receive the surgeon input, and fabrication machinery that fabricates at least one of the surgeon-specific tibial cutting guide or the surgeon-specific femoral cutting guide.

In some embodiments, the instrumentation manufacturing system may comprise a server configured to receive the surgeon input and transmit instructions to the fabrication machinery for fabrication of the at least one of the surgeon-specific tibial cutting guide or the surgeon-specific femoral cutting guide based on the surgeon input.

There is also provided one or more machine-readable storage media comprising a plurality of instructions stored thereon that, in response to execution by a computing device, causes the computing device to prompt a surgeon for a plurality of adaptive tibial guide parameters collectively indicative of a physical structure of a surgeon-specific tibial cutting guide and a plurality of adaptive femoral guide parameters collectively indicative of a physical structure of a surgeon-specific femoral cutting guide for a surgical procedure on a patient, receive surgeon input from the surgeon associated with the plurality of adaptive tibial guide parameters and the plurality of adaptive femoral guide parameters, and transmit the received surgeon input to an instrumentation manufacturing system for manufacturing of at least one of the surgeon-specific tibial cutting guide and the surgeon-specific femoral cutting guide.

There is a provided herein a method that includes obtaining, using an imaging device, one or more bone images of a bone, and modeling, using at least the one or more bone images, a virtual visualization of the bone. The method can also include analyzing, virtually, one or more bone cuts at one or more locations along the virtual visualization of the bone, and selecting, based at least in part on the analysis of the one or more bone cuts, a bone cut location for cutting the bone. Additionally, a bone cutting block, such as, for example, an adaptive guide, can be built using at least information from the selected bone cut location.

According to some embodiments, the analysis of the one or more bone cuts can comprise evaluating at least one of a size and a shape of the bone at the one or more bone cut locations. Further, the method can also include determining a location of an eminence indicator for the bone cutting block. Additionally, according to certain embodiments, the method can further include analyzing, virtually, one or more insertion locations of one or more ligaments along the bone. Further, the one or more insertion locations can include insertion locations along a tibial eminence of the bone. The method can also include analyzing compromises between at least one of the size and shape of the bone at the one or more bone cut locations and one or more characteristics of the one or more ligaments at the one or more bone cut locations. Additionally, the method can further include performing, virtually, at least a portion of an implant procedure using at least the virtual visualization of the bone and a virtual representation of a tool or component of an implant system.

There is also provided herein is an apparatus that includes a medial tibial paddle that is configured to overly at least a portion of a medial plateau of a bone, and a lateral tibial paddle that is configured to overly at least portions of a lateral plateau of the bone. The apparatus can also include an eminence indicator that is positioned within between the medial and lateral tibial paddles. The eminence indicator can have a plurality of walls that are positioned to identify a plurality of eminence corners for an eminence cut of the bone.

According to some embodiments, the eminence indicator can comprise a medial wall and a lateral wall, the medial wall and the lateral wall being positioned to define a width of a tibial eminence of the bone that is to be retained by the eminence cut. Further, the eminence indicator can include a first arm and a second arm. At least a first wall portion of both the first and second arms can be positioned to define an ending location of the tibial eminence of the bone that is to be retained by the eminence cut. Additionally, the medial wall can be approximately parallel to the lateral wall, while the medial wall and the lateral wall can be approximately perpendicular to the first wall portion of both the first and second arms.

Further, according to some embodiments, an inner sidewall of the medial tibial paddle can be positioned at a location that corresponds to an internal-external rotation of a tibial eminence of the bone. Additionally, the apparatus can further define a cutting slot that extends through at least a portion of the apparatus, and which is sized to guide a displacement of a cutting blade. The apparatus can also include a datum block that is positioned distally of the cutting slot, the datum block having one or more datum pin holes and is configured to establish a plane parallel to a plane of the cutting slot.

Additionally, according to some embodiments, at least one of the medial tibial paddle and the lateral tibial paddle includes a removable paddle extension. Further, at least one of the medial tibial paddle and the lateral tibial paddle can have a pin hole and a guide boss, the guide boss having a boss body, a neck portion, and a removable capture portion. The neck portion can couple the boss body to the removable capture portion, and can have a smaller wall cross-sectional thickness than the boss body and the removable capture portion.

There is also provided an apparatus that includes a paddle section having at least two paddles, the at least two paddles configured to overlay at least an end portion of a bone. The paddle section can also include an eminence indicator that is positioned between the at least two paddles, the eminence indicator having a plurality of walls positioned to identify a plurality of eminence corners for an eminence cut of the bone. The apparatus can also include an alignment section positioned distally of the paddle section, at least a portion of the alignment section defining a cutting slot sized to receive a cutting blade. Additionally, the apparatus can include a datum block that is positioned distally of the alignment section, the datum block having one or more datum pin holes and is configured to establish a plane parallel to a plane of the cutting slot.

According to some embodiments, the alignment section further includes an orientation stylus pin hole positioned to align with a hole in the bone that receives a pin for an orientation stylus. Further, according to some embodiments, at least one of the at least two paddles includes a removable paddle extension.

Additionally, according to some embodiments, at least one of the at least two paddles includes a pin hole and a guide boss, the guide boss having a boss body and a removable capture portion, the guide boss having a boss body, a neck portion, and a removable capture portion. The neck portion can couple the boss body to the removable capture portion, and can have a smaller wall cross-sectional thickness than the boss body and the removable capture portion.

There is provided a method that includes identifying, for selection, a plurality of different implant systems for implantation into a patient, and identifying, for use with the selected implant system, a plurality of preparatory tools, one of more of the identified plurality of implant tools not being specific to the selected implant system.

According to certain embodiments, the method can further include at least one of selecting one of the plurality of different implantation systems, and selecting one of the one or more identified plurality of implant tools that is not specific to the selected implant system. Additionally, according to certain embodiments, the method can also include building the selected one of the plurality of implant tools, and modifying at least one feature of the selected one of the plurality of implant tools to conform to a similar feature of the selected implant system. Further, according to certain embodiments, the plurality of different implantation systems can include a plurality of different models, brands, and/or manufacturers of knee implant systems, and wherein the preparatory tools are cutting blocks that are specific to one or more of the knee implant systems.

There is also provided a method that includes identifying a first non-implant-specific pin hole configuration of a first implant system and identifying a second non-implant-specific pin hole configuration of a second implant system, the first implant system being different from the second implant system. Further, a compatibility of the first non-implant-specific pin hole configuration with the second non-implant-specific pin hole configuration can be determined. If the first and second non-implant-specific pin hole configurations are determined to be compatible, then the method can further include providing a preparatory tool having one or more pin holes having the second non-implant-specific pin hole configuration for implantation of the first implant system.

According to some embodiments, the preparatory tool can comprise, for example, a cutting block, and the first implant system and the second implant system can be each knee implant systems. Further, the first non-implant-specific pin hole configuration and the second non-implant-specific pin hole configuration can both comprise at least one recut hole configuration. Additionally, the cutting block can be a recut cutting block. Further, the difference between the first implant system and the second implant system can comprise a difference in at least one of the following: model, brand, and manufacturer.

Additionally, according to some embodiments, the first implant system can include a preparatory tool having one or more pin holes having the first non-implant-specific pin hole configuration, and the preparatory tool of the first implant system can have a different configuration than the preparatory tool of the second implant system.

There is also provided a method that includes selecting, based on a compatibility with a non-implant-specific pin hole configuration of a first implant system, a cutting block of a second implant system, the second implant system being a different type of implant system than the first implant system. Further, using at least in part pin holes having the non-implant-specific pin hole configuration, a cutting block of the first implant system can be secured to a bone at a first bone location. The method can also include securing, using at least in part pin holes having the non-implant-specific pin hole configuration, the cutting block of the second implant system to the bone generally at the first bone location.

Additionally, according to some embodiments. the non-implant-specific pin hole configuration of the first implant system can be a recut pin hole configuration, and the second cutting block can be a recut cutting block. Further, the recut cutting block can comprise a plurality of sets of recut pin holes, each of the plurality of sets of recut pin holes having the non-implant-specific pin hole configuration. Additionally, the cutting block of the first system and the recut cutting block of the second system can have different sizes. Additionally, the step of selecting the cutting block of the second implant system can include the step of displaying, on a display and for selection, at least the second cutting block. Further, the difference in type can comprise a difference in at least one of the following: model, brand, and manufacturer.

Additionally, there is also provided a method that includes identifying a non-implant-specific pin hole configuration of a first implant system, the non-implant-specific pin hole configuration configured to receive one or more pins that assist in operably securing at least one preparatory tool of the first implant system having the non-implant-specific pin hole configuration at a first bone location of a bone. Further, one or more other implant systems having a non-implantspecific pin hole configuration compatible with the non-implant-specific pin hole configuration of the first implant system can also be identified, the non-implant-specific pin hole configuration of the one or more other implant systems being configured to receive one or more pins that assist in operably securing at least one preparatory tool of the one or more other implant systems at the first bone location. Further, the at least one preparatory tool of the one or more implant systems can have a different configuration than the at least one preparatory tool of the first implant system. The method can also include displaying, on a display and for selection, the at least one preparatory tool of the identified one or more implant systems having the non-implant-specific pin hole configuration.

Additionally, according to certain embodiments, the method can also include selecting, from the displayed at least one preparatory tool, a preparatory tool of the identified one or more implant systems, and securing the selected preparatory tool of the one or more implant systems at the first bone location during implantation of the first implant system.

Further, according to certain embodiments, the first implant system can be a first knee implant system, and the one or more other implant systems can be one or more other knee systems that are either a different model or brand than the first knee implant system. Additionally, the non-implant-specific pin holes of the first implant system can comprise a plurality of recut holes of a cutting block, and wherein the one or more non-implant-specific pin holes of the one or more other implant systems can comprise a plurality of recut holes of one or more recut cutting blocks. The cutting block can be at least one of a femoral cutting block and a tibial cutting block, and the one or more recut cutting blocks can be at least one of a femoral recut cutting block and a tibial recut cutting block. Additionally, the at least one preparatory tool of the one or more other implant systems can include at least one preparatory tool having a plurality of non-implant-specific pin hole configurations, each of the plurality of non-implant-specific pin hole configurations being compatible with the non-implant-specific pin hole configuration of the first implant system.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore, it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A method, comprising:
   prompting, by a graphical user interface presented on a display device of a computing system, a surgeon for a plurality of adaptive tibial guide parameters collectively indicative of a physical structure of a surgeon-specific tibial cutting guide and a plurality of adaptive femoral guide parameters collectively indicative of a physical structure of a surgeon-specific femoral cutting guide for a surgical procedure on a patient;
   receiving, via the graphical user interface of the computing system, surgeon input from the surgeon associated with the plurality of adaptive tibial guide parameters and the plurality of adaptive femoral guide parameters; and
   transmitting, via a communication circuitry of the computing system, the received surgeon input to an instrumentation manufacturing system for manufacturing of at least one of the surgeon-specific tibial cutting guide and the surgeon-specific femoral cutting guide;
   wherein prompting the surgeon for the plurality of adaptive tibial guide parameters and the plurality of adaptive femoral guide parameters comprises prompting the surgeon to select from a distal femur cut first surgical technique or a tibial cut first surgical technique.

2. The method of claim 1, further comprising fabricating the surgeon-specific tibial cutting guide using fabrication machinery of the instrumentation manufacturing system.

3. The method of claim 1, further comprising fabricating the surgeon-specific femoral cutting guide using fabrication machinery of the instrumentation manufacturing system.

4. The method of claim 1, further comprising validating the surgeon input to confirm that the plurality of adaptive tibial guide parameters and the plurality of adaptive femoral guide parameters desired by the surgeon are consistent with an anatomy of the patient.

5. The method of claim 1, wherein prompting the surgeon for the plurality of adaptive tibial guide parameters and the plurality of adaptive femoral guide parameters comprises separately prompting the surgeon for the plurality of adaptive tibial guide parameters and prompting the surgeon for the plurality of adaptive femoral guide parameters.

6. The method of claim 1, wherein prompting the surgeon for the plurality of adaptive tibial guide parameters and the plurality of adaptive femoral guide parameters comprises prompting the surgeon to select from a surgeon-specific tibial cutting guide including a tibial paddle having at least one contact extension or a surgeon-specific tibial cutting guide without the at least one contact extension.

7. The method of claim 6, wherein the at least one contact extension is separable from a remainder of the tibial paddle.

8. The method of claim 6, wherein prompting the surgeon for the plurality of adaptive tibial guide parameters and the plurality of adaptive femoral guide parameters comprises prompting the surgeon to select a thickness of a cutting blade of a cutting instrument to be used with the surgeon-specific tibial cutting guide.

9. The method of claim 8, wherein prompting the surgeon for the plurality of adaptive tibial guide parameters and the plurality of adaptive femoral guide parameters comprises prompting the surgeon to select from a surgeon-specific tibial cutting guide that is designed for use with a surgical technique in which an alignment rod is aligned parallel to a mechanical axis of the patient's tibia to gauge alignment or a surgeon-specific tibial cutting guide that is designed for use with a surgical technique in which the alignment rod is aligned perpendicular to a cutting slot of the surgeon-specific tibial cutting guide.

10. The method of claim 8, wherein prompting the surgeon for the plurality of adaptive tibial guide parameters and the plurality of adaptive femoral guide parameters comprises prompting the surgeon to select from a surgeon-specific tibial cutting guide having a least one rimmed pinhole or a surgeon-specific tibial cutting guide without the at least one rimmed pinhole.

11. The method of claim 8, wherein prompting the surgeon for the plurality of adaptive tibial guide parameters and the plurality of adaptive femoral guide parameters comprises prompting the surgeon to select from a surgeon-specific tibial cutting guide having at least one bicruciate ligament sparing feature or a surgeon-specific tibial cutting guide without the at least one bicruciate ligament sparing feature.

12. The method of claim 8, wherein prompting the surgeon for the plurality of adaptive tibial guide parameters and the plurality of adaptive femoral guide parameters comprises prompting the surgeon to select at least one preferred standard surgical recut guide.

13. The method of claim 8, wherein prompting the surgeon for the plurality of adaptive tibial guide parameters and the plurality of adaptive femoral guide parameters comprises prompting the surgeon to select from a surgeon-specific tibial cutting guide having at least one tibial paddle that extends distal to a cut plane of a cutting instrument to contact a proximal surface of the patient's tibia or a surgeon-specific tibial cutting guide with no tibial paddle that extends distal to the cut plane.

14. The method of claim 1, wherein prompting the surgeon for the plurality of adaptive tibial guide parameters and the plurality of adaptive femoral guide parameters comprises prompting the surgeon to select from a surgeon-specific femoral cutting guide having a least one rimmed pinhole or a surgeon-specific femoral cutting guide without the at least one rimmed pinhole.

\* \* \* \* \*